United States Patent
Tall et al.

(10) Patent No.: US 9,687,486 B2
(45) Date of Patent: Jun. 27, 2017

(54) METHODS OF TREATING ATHEROSCLEROSIS OR MYELOPROLIFERATIVE NEOPLASMS BY ADMINISTERING A LYN KINASE ACTIVATOR

(71) Applicants: Alan R. Tall, New York, NY (US); Nan Wang, Flushing, NY (US)

(72) Inventors: Alan R. Tall, New York, NY (US); Nan Wang, Flushing, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 14/650,685

(22) PCT Filed: Dec. 20, 2013

(86) PCT No.: PCT/US2013/077026
§ 371 (c)(1),
(2) Date: Jun. 9, 2015

(87) PCT Pub. No.: WO2014/100636
PCT Pub. Date: Jun. 26, 2014

(65) Prior Publication Data
US 2015/0366867 A1    Dec. 24, 2015

Related U.S. Application Data

(60) Provisional application No. 61/740,320, filed on Dec. 20, 2012.

(51) Int. Cl.
A61K 31/513    (2006.01)
A61K 45/06    (2006.01)

(52) U.S. Cl.
CPC ............ *A61K 31/513* (2013.01); *A61K 45/06* (2013.01)

(58) Field of Classification Search
CPC ..................................................... A61K 31/513
(Continued)

(56) References Cited

U.S. PATENT DOCUMENTS 7,776,870 B2 *   8/2010   Reaume ............... A61K 31/495
                                                              514/269
8,343,985 B2 *   1/2013   Reaume ............... A61K 31/495
                                                              514/269
(Continued)

FOREIGN PATENT DOCUMENTS

WO    WO 2006/001954 A2    1/2006
WO    WO 2014/100636 A2    6/2014

OTHER PUBLICATIONS

Tall, Alan. "ABC transporters regulate hematopoietic stem and progenitor cell proliferation, leukocytosis, thrombocytosis and atherosclerosis," Sep. 24, 2012 (Sep. 24, 2012), Abstract. p. 19.
(Continued)

*Primary Examiner* — Kamal Saeed
*Assistant Examiner* — Janet L Coppins
(74) *Attorney, Agent, or Firm* — John P. White; Cooper & Dunham LLP

(57) ABSTRACT

This invention provides a method of treating a subject suffering from atherosclerosis or a myeloproliferative neoplasm which comprises administering to the subject an amount of a Lyn kinase activator effective to activate Lyn kinase so as to thereby treat the subject.

15 Claims, 57 Drawing Sheets

(58) Field of Classification Search
USPC .................................................. 514/269, 274
See application file for complete search history.

(56) References Cited

U.S. PATENT DOCUMENTS

| | | |
|---|---|---|
| 2005/0203029 A1 | 9/2005 | Schubert et al. |
| 2007/0093516 A1 | 4/2007 | Reaume et al. |
| 2012/0220527 A1 | 8/2012 | Simari et al. |

OTHER PUBLICATIONS

Auger et al. "c-Cbl negatively regulates platelet activation by glycoprotein VI," Journal of Thrombosis and Haemostasis, Nov. 1, 2003 (Nov. 1, 2003), vol. 1, pp. 2419-2426. Entire document.

Murphy et al. "Cholesterol efflux in megakaryocyte progenitors suppresses platelet production and thrombocytosis," Nature Medicine, Apr. 14, 2014 (Apr. 14, 2014), vol. 19, No. %, pp. 586-596. Entire document.

International Search Report, mailed Sep. 15, 2014 in connection with PCT International Application No. PCT/US2014/033659, filed Apr. 10, 2014.

Written Opinion of the International Searching Authority, mailed Sep. 15, 2014 in connection with PCT International Application No. PCT/US2014/033659, filed Apr. 10, 2014.

Italiano, J. T. (2008). Megakaryocyte and platelet biology: Getting your FAKs straight. *blood,* 111(2) , 482-483.

Notification of Transmittal of the International Search Report and the Written Opinion of the International Searching Authority, or the Declaration, including an International Search Report and Written Opinion of the International Searching Authority, mailed Jun. 10, 2014 in connection with PCT International Application No. PCT/US2013/077026, filed Dec. 20, 2013.

Office Action issued Aug. 25, 2016 in connection with U.S. Appl. No. 14/783,789.

\* cited by examiner

Figures 1D-F.
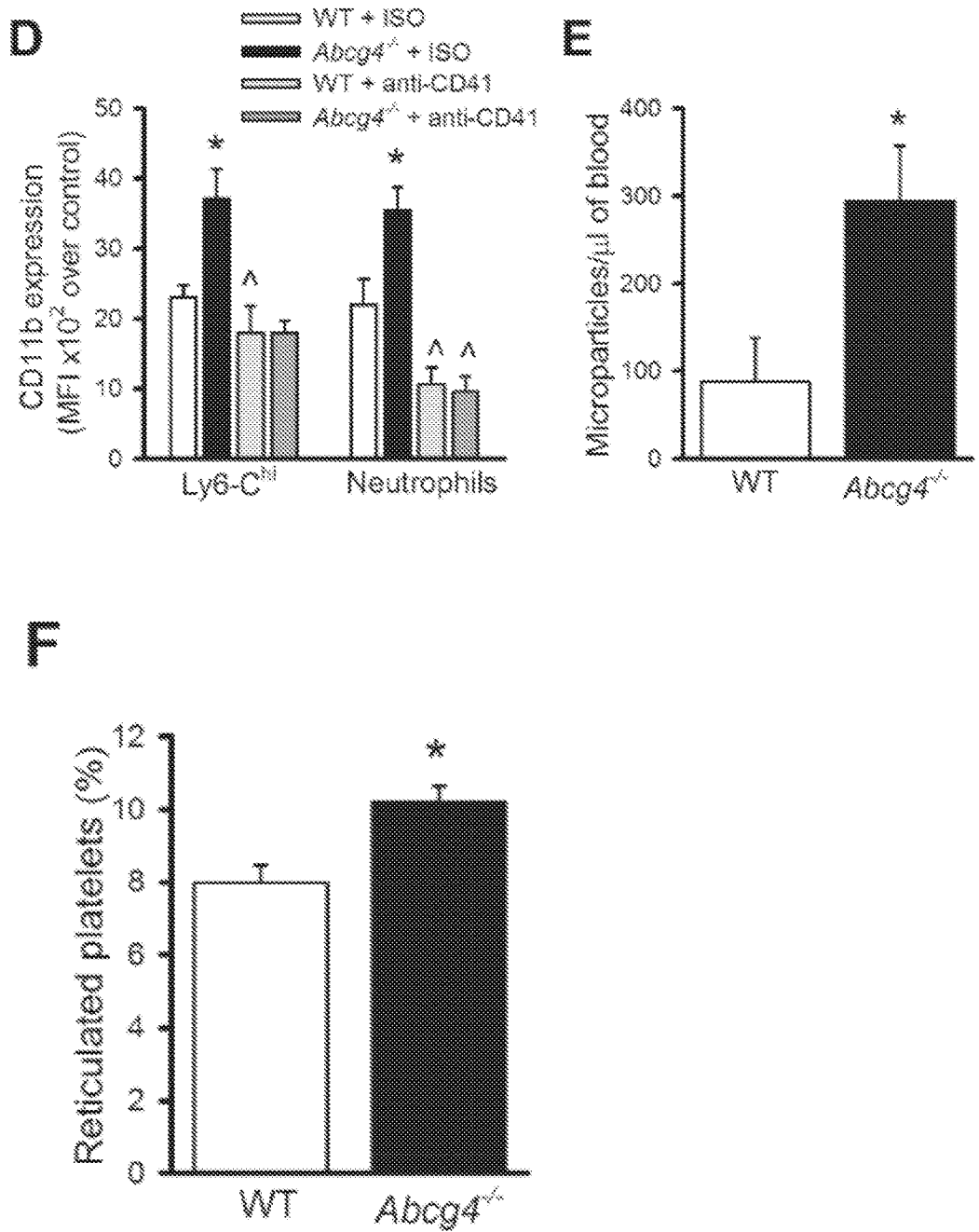

Figure 1G.
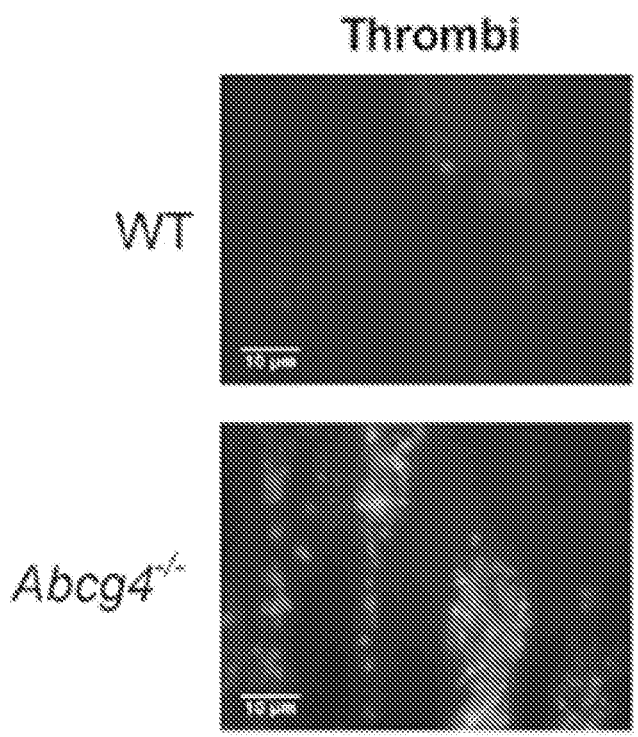
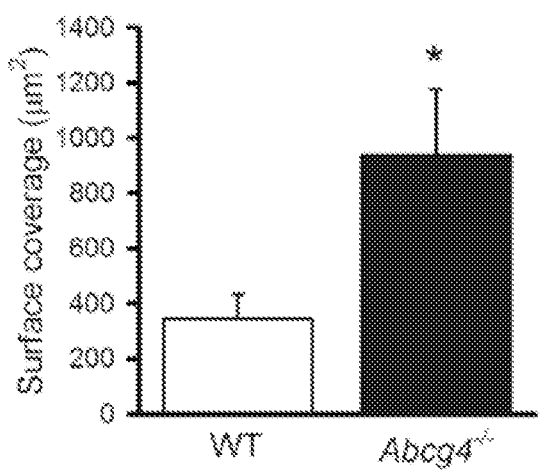

Figures 2A-B.
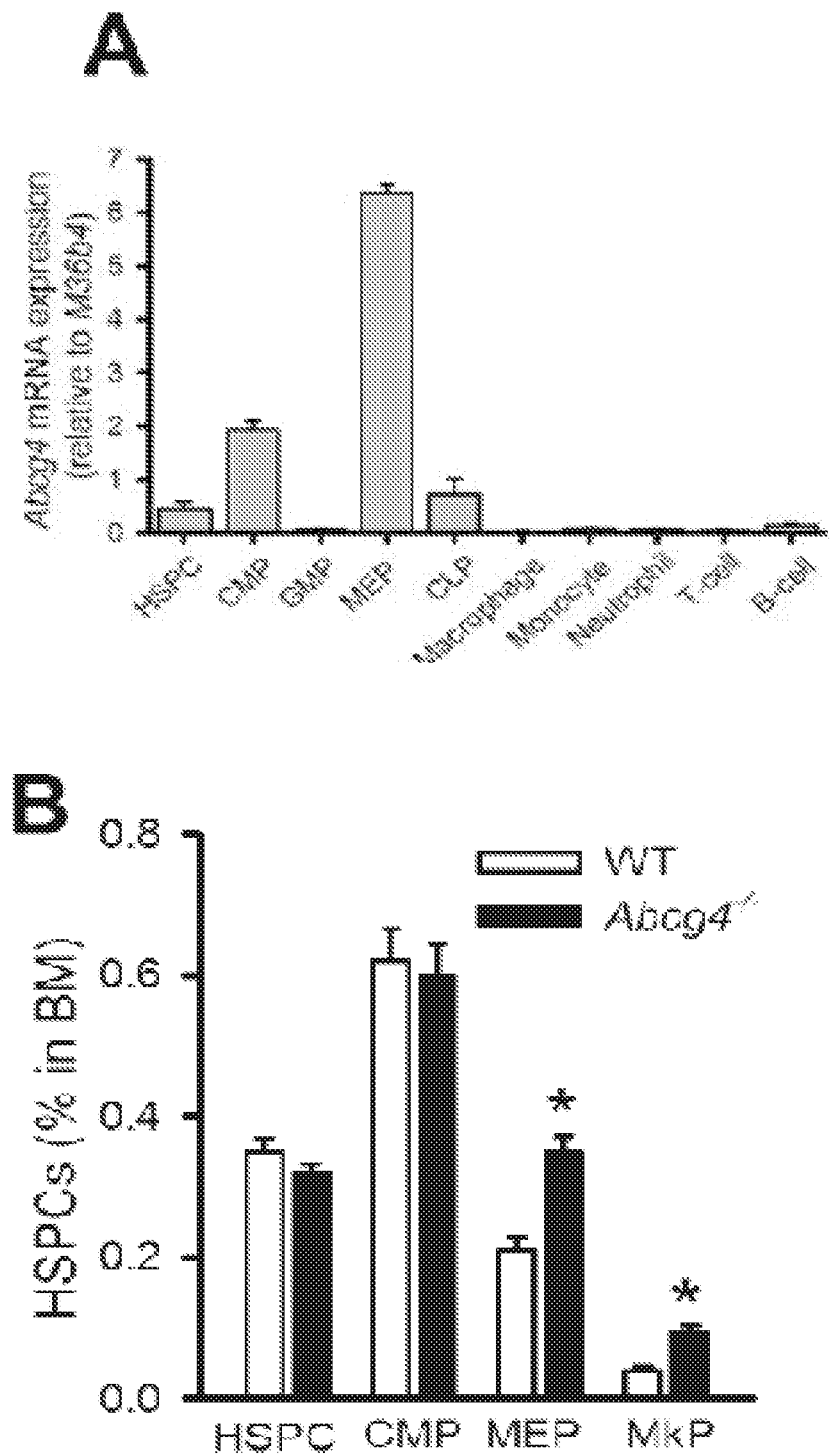

Figures 2G-I.
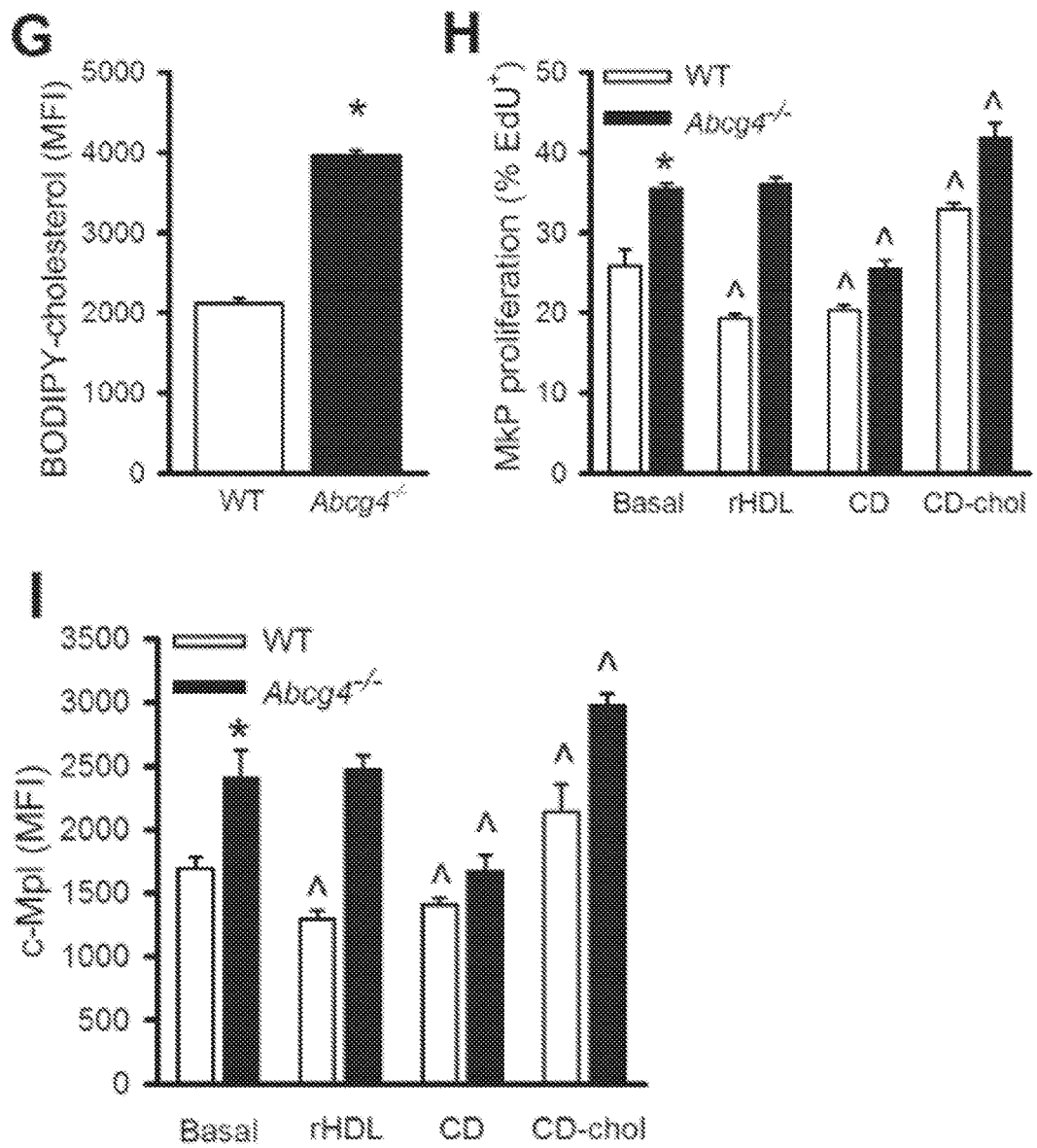

Figures 3A-B.
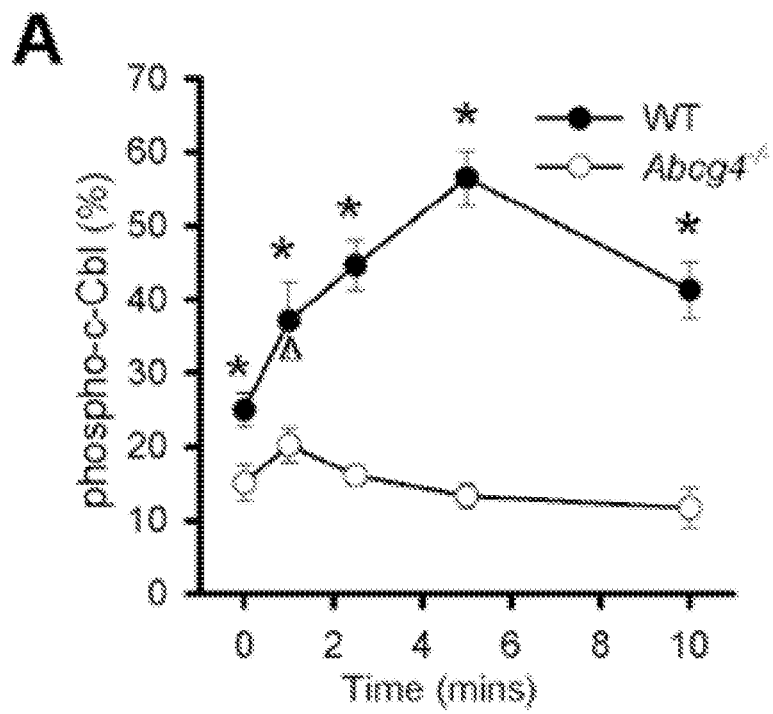
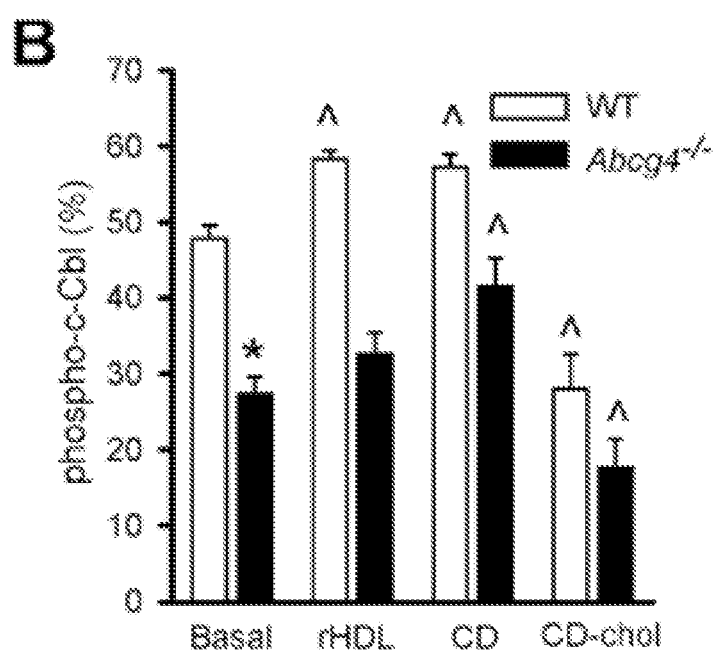

Figures 3C-D.
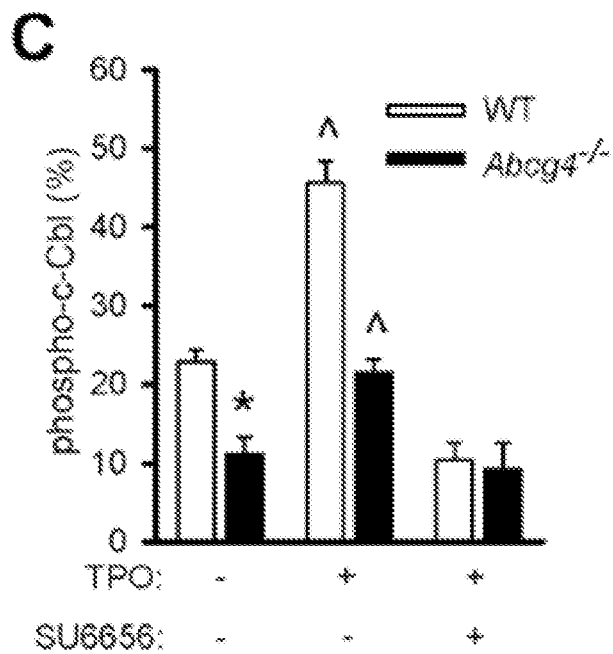
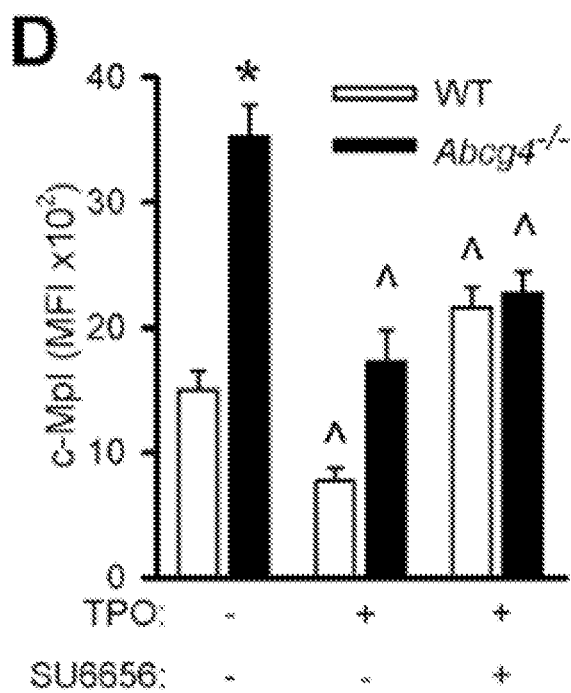

Figures 3E-F.
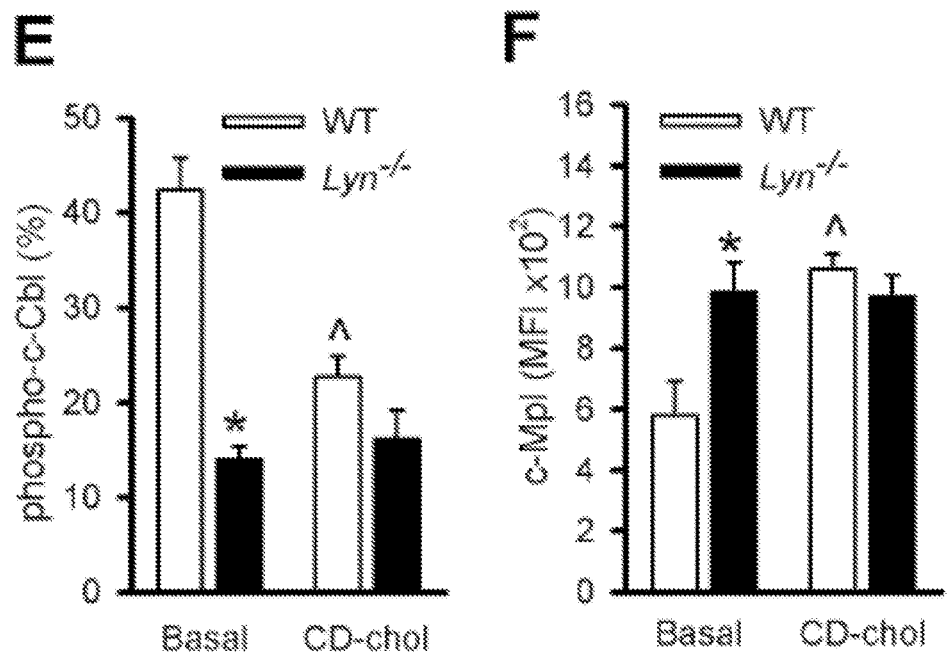

Figures 3G-H.
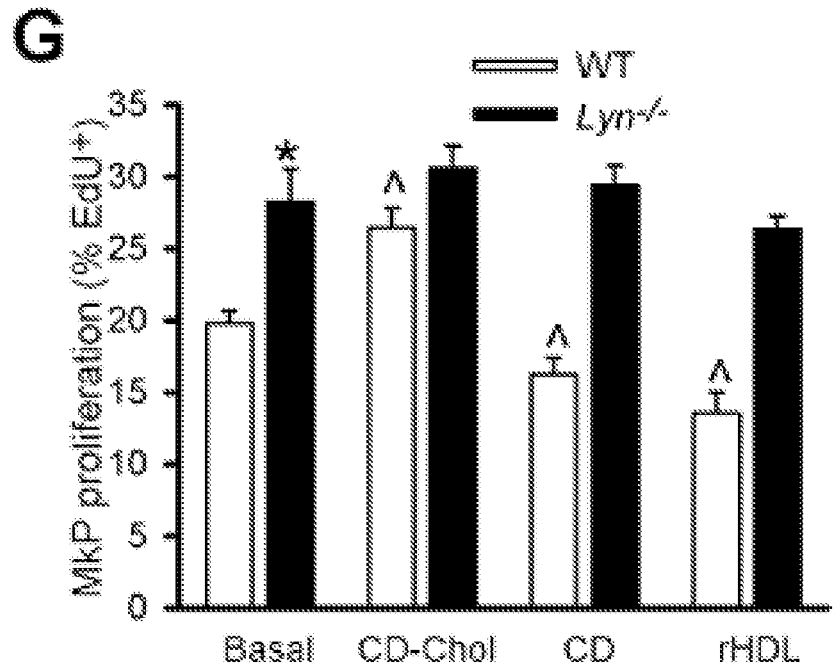
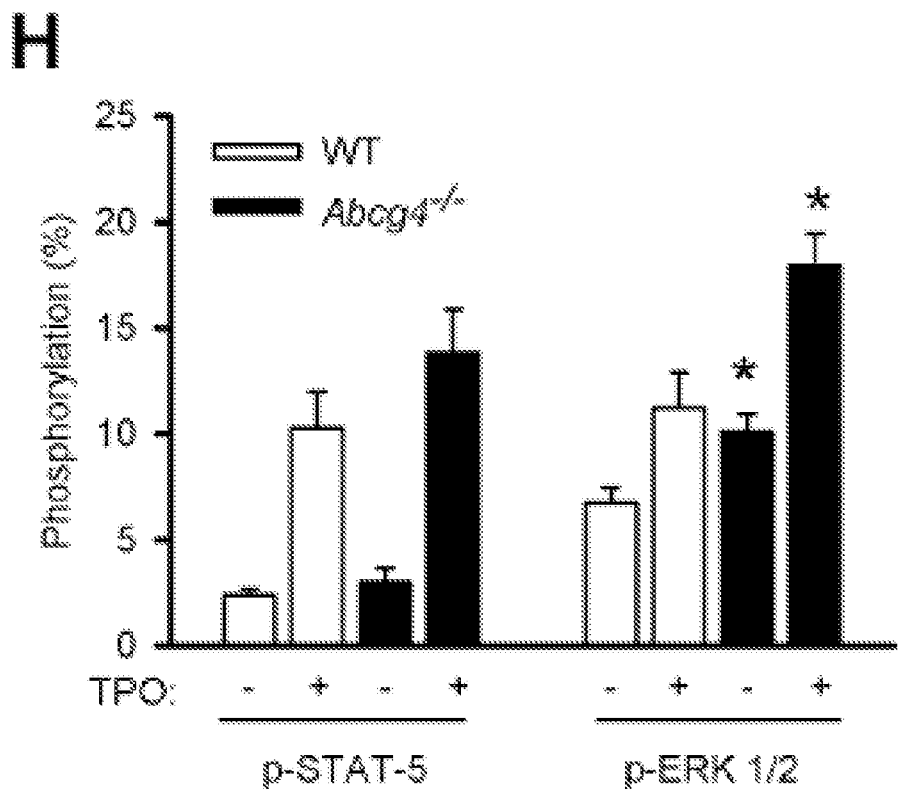

Figures 4A-B.
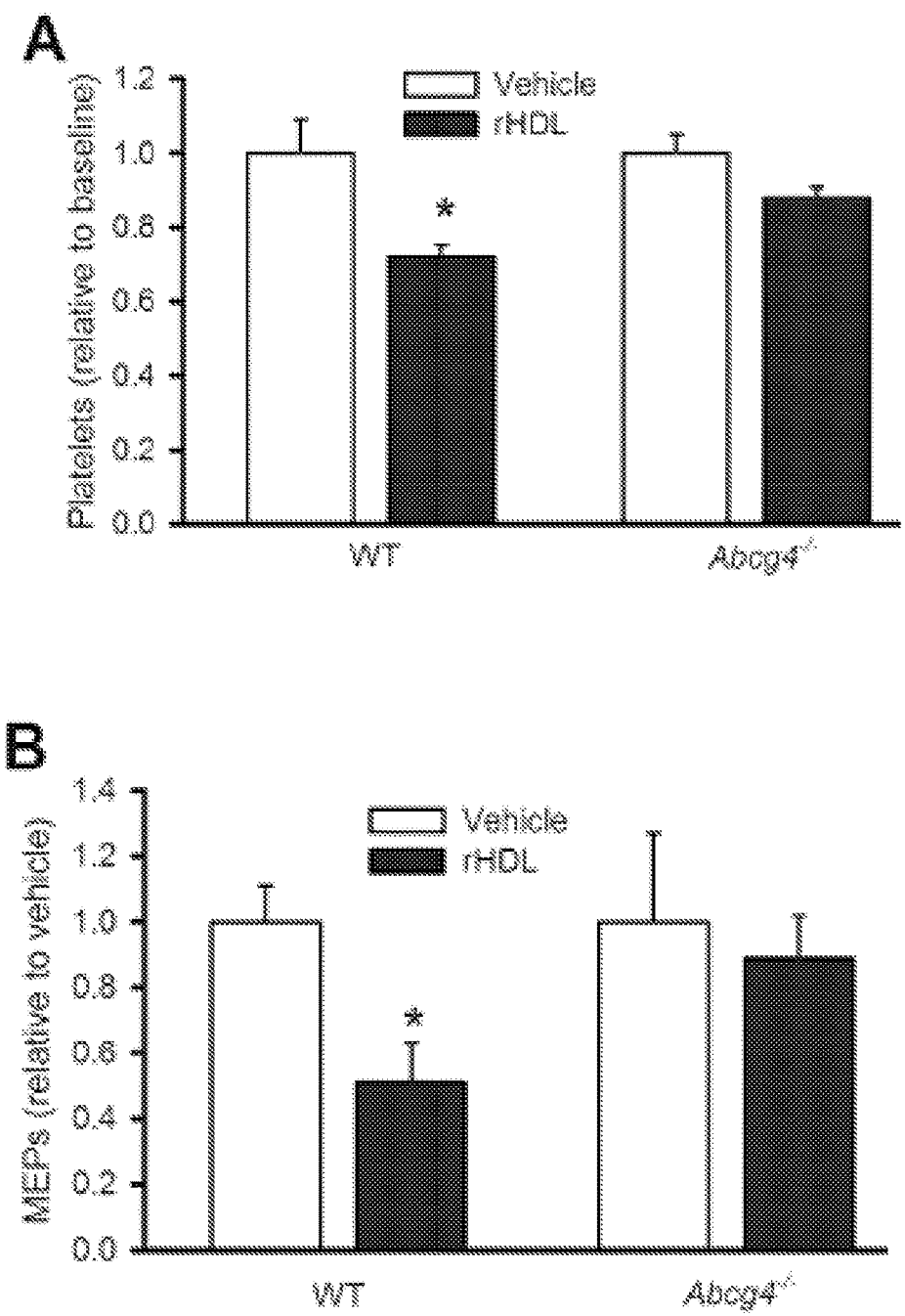

Figure 5A.
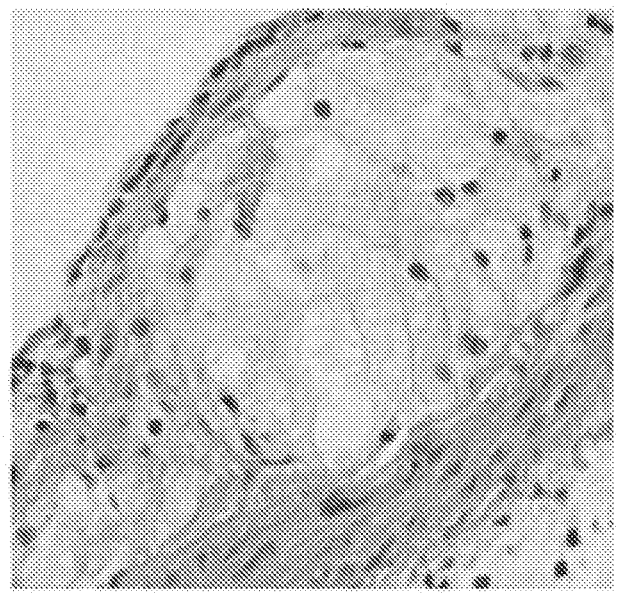
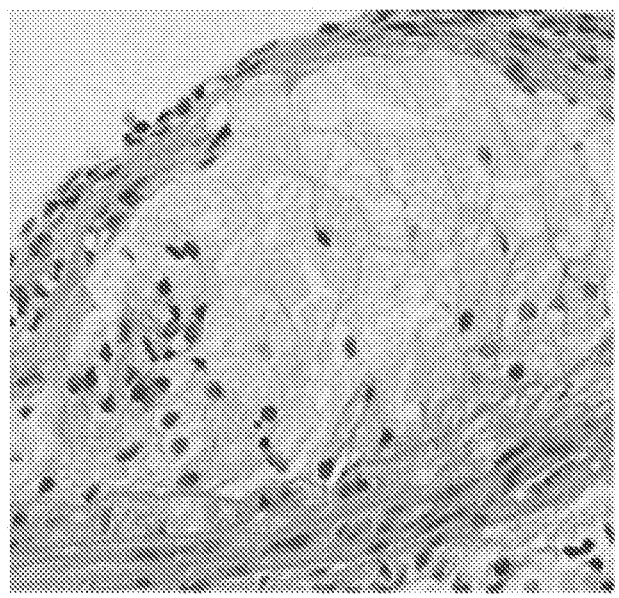

Figures 5B-C.
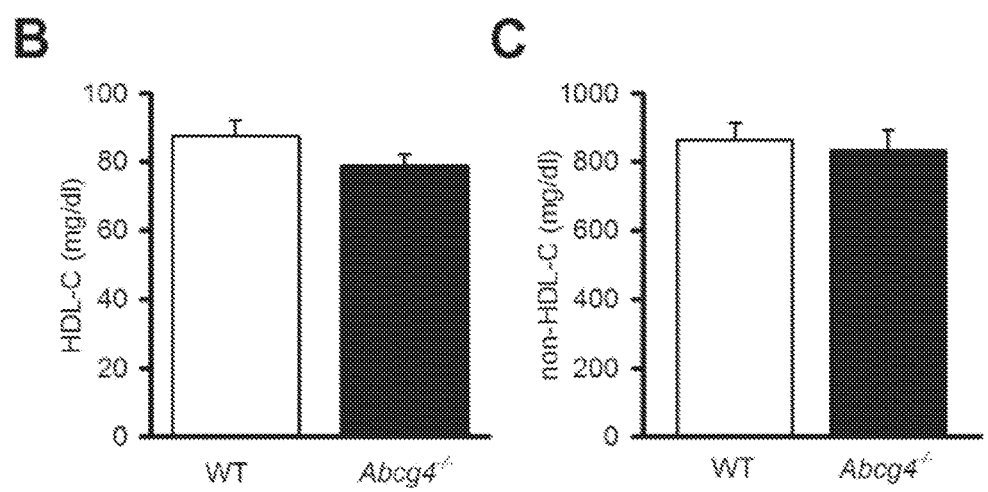

Figures 5D-G.
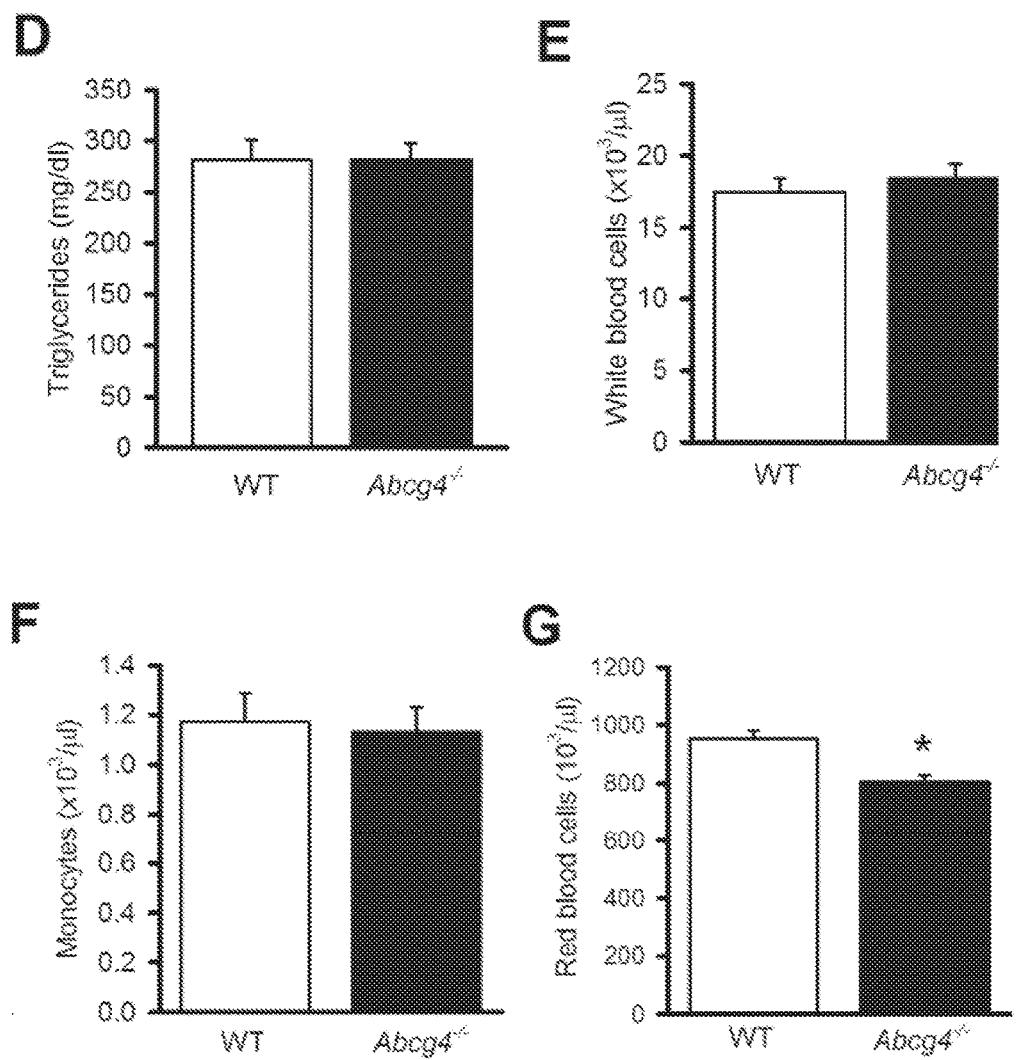

Figures 5H-I.
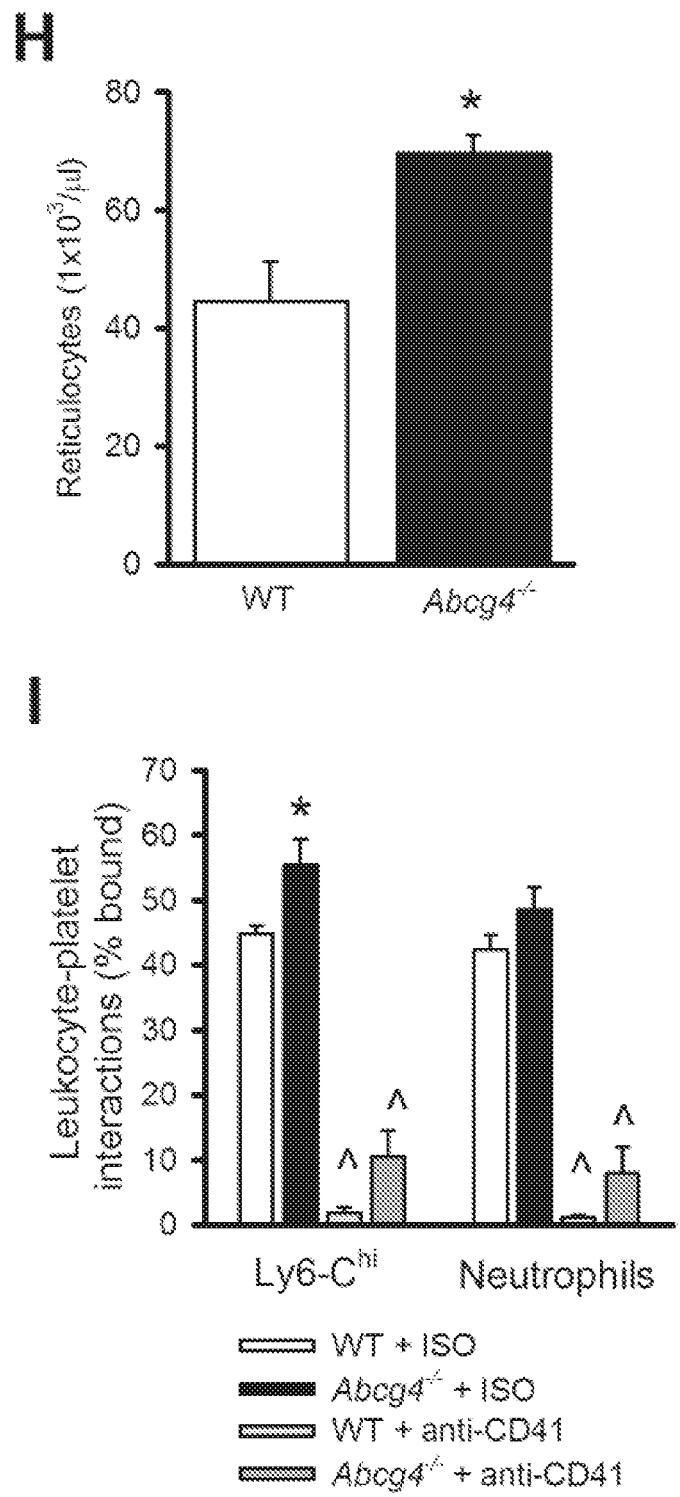

Figures 6A-B.
A
BM: LacZ
WT
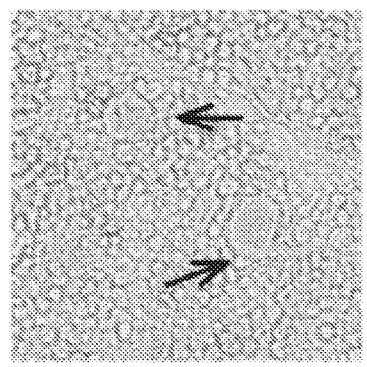
Abcg4⁻/⁻
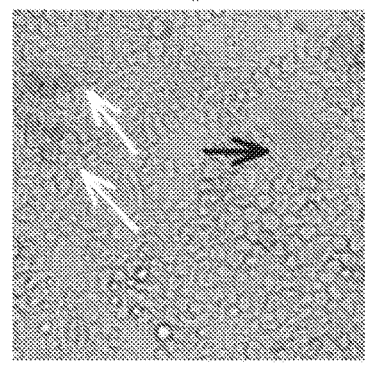
B
WT
Chow diet
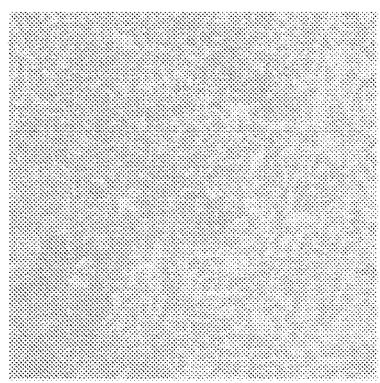
Abcg4⁻/⁻
Chow diet
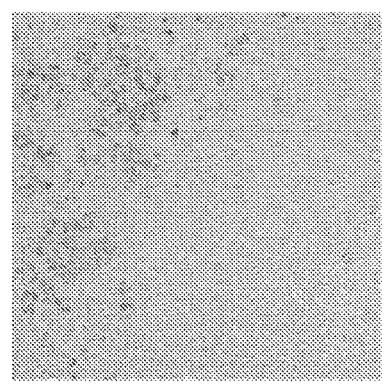
Spleen LacZ Figures 7A-B.
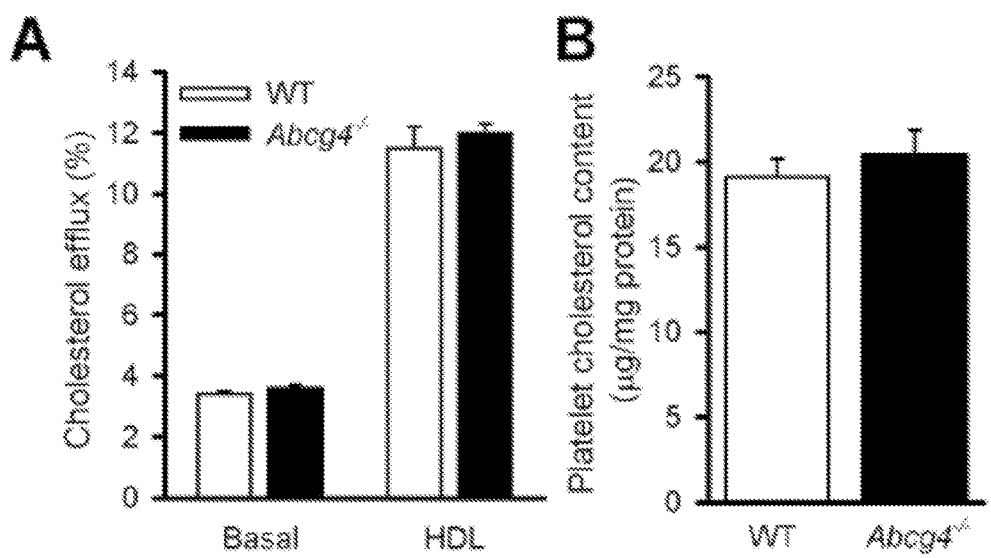

Figures 8A-B.
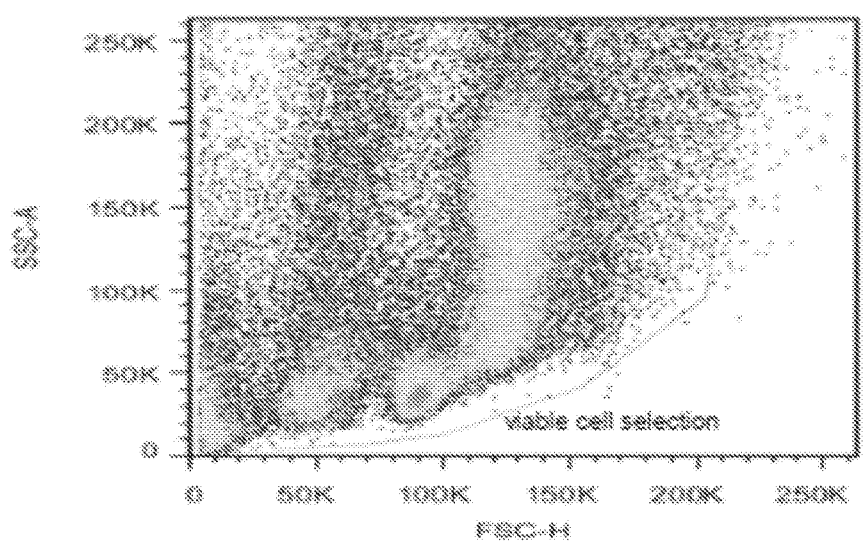
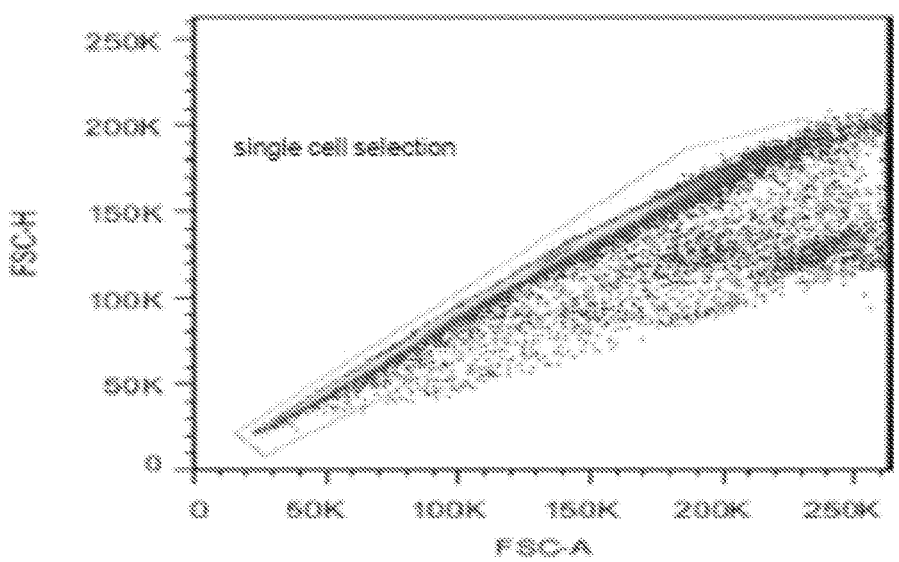

Figures 8C-D.
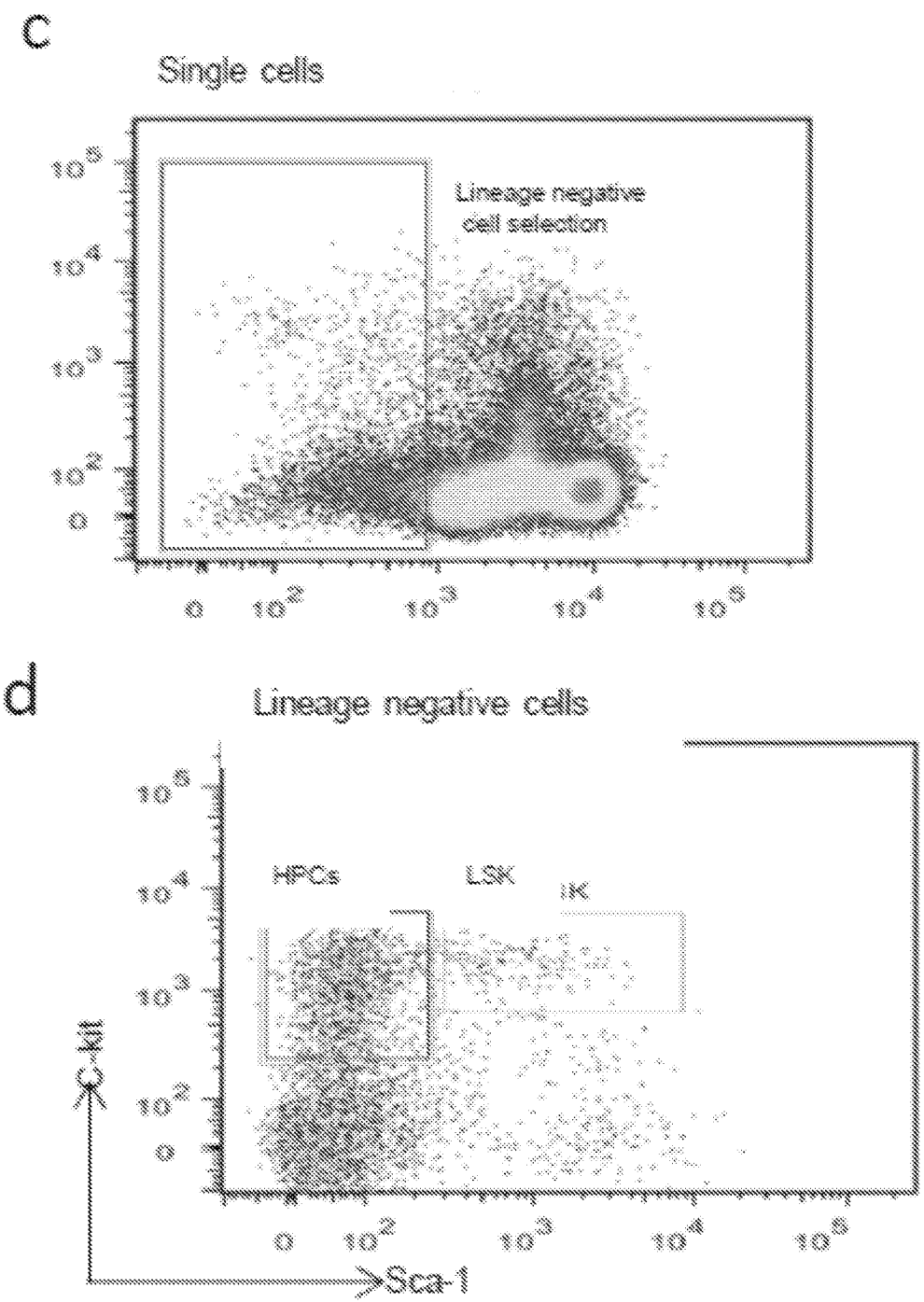

Figures 8E-F.
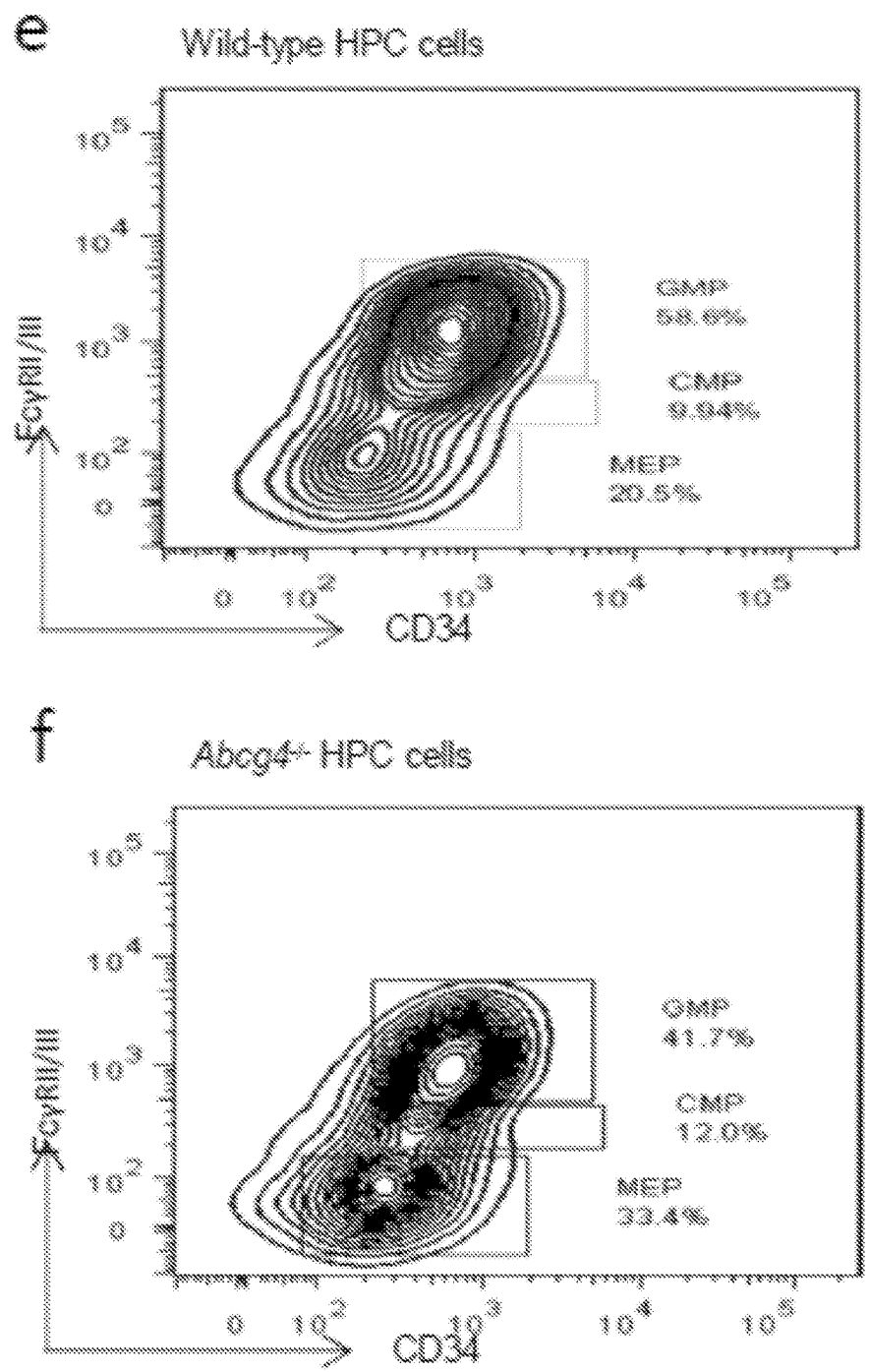

Figures 9A-B.
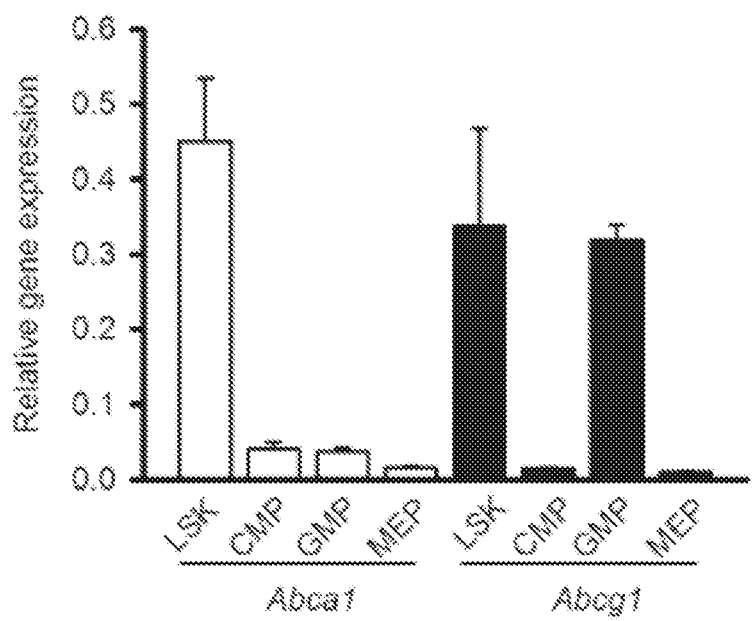
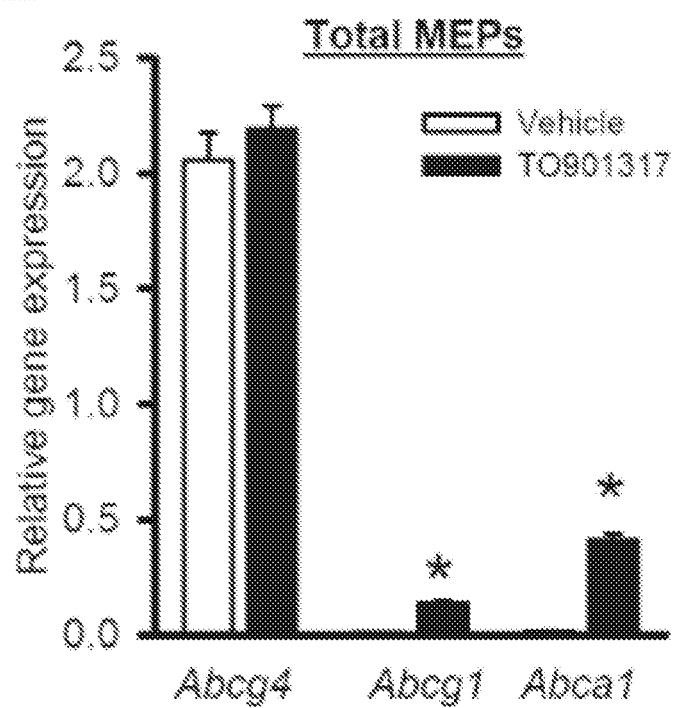

Figure 10A.
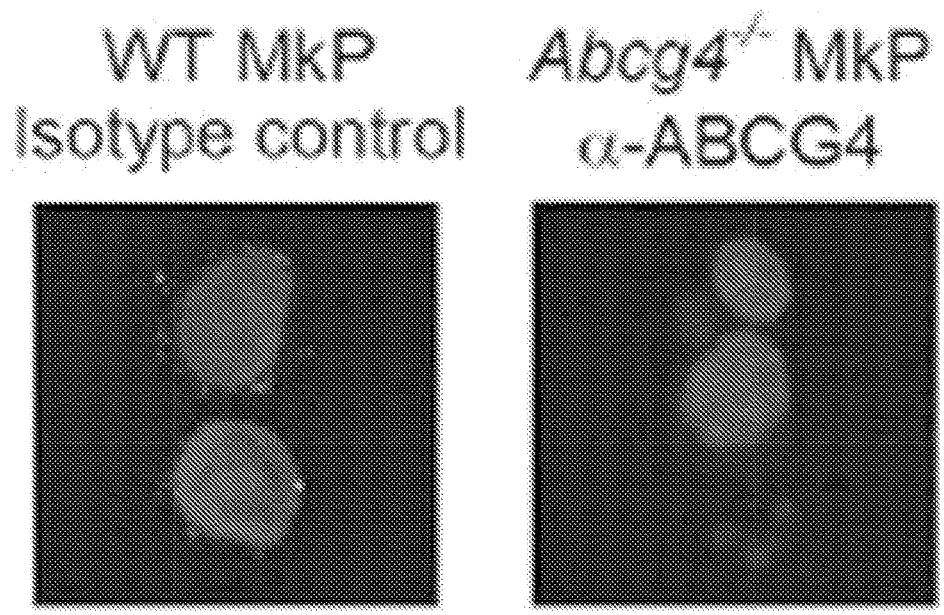
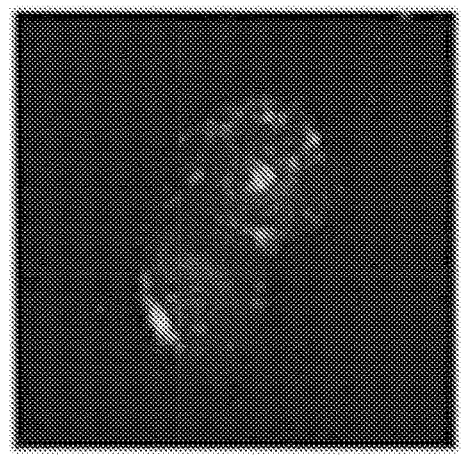

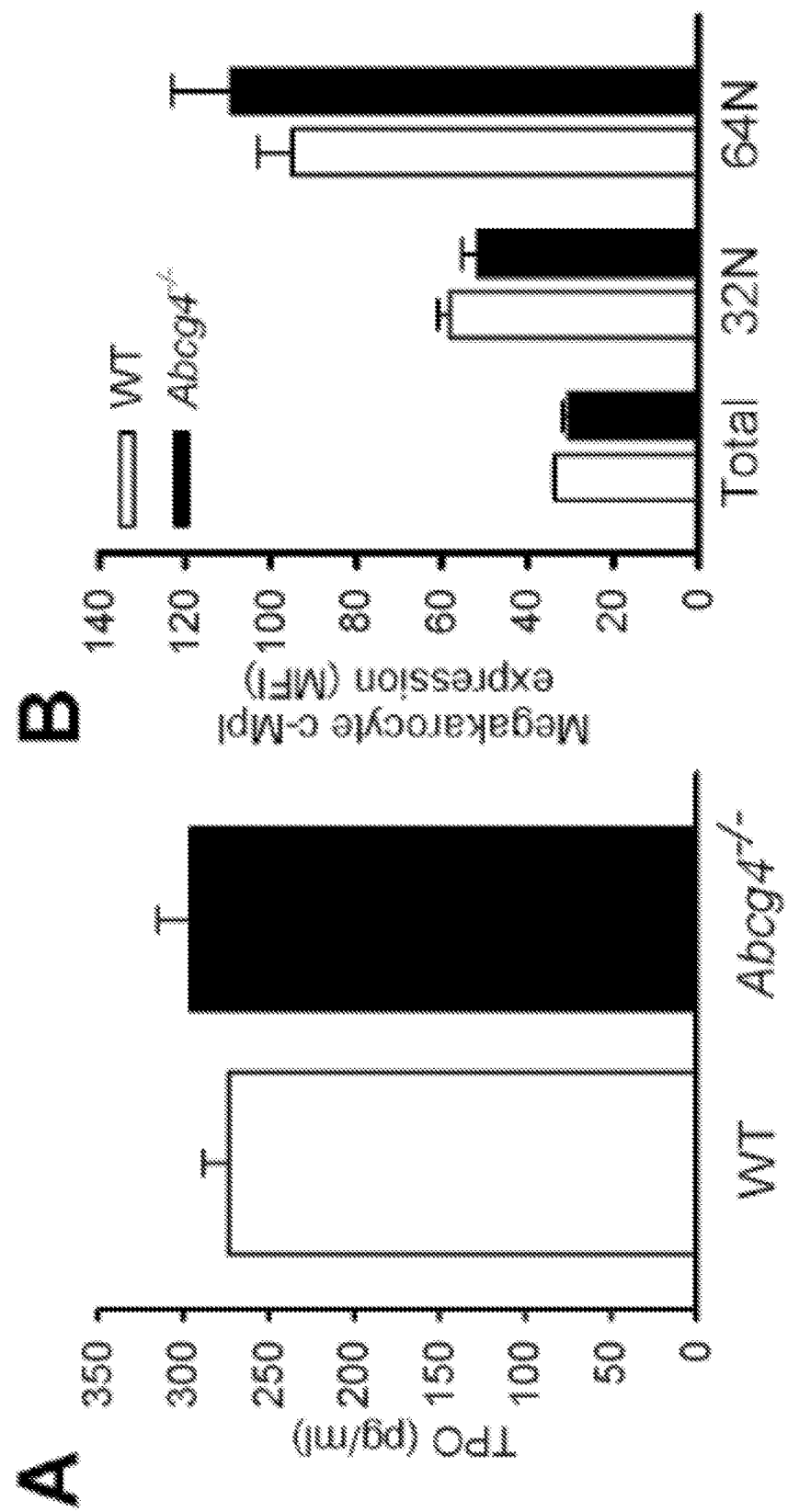
Figures 11A-B.

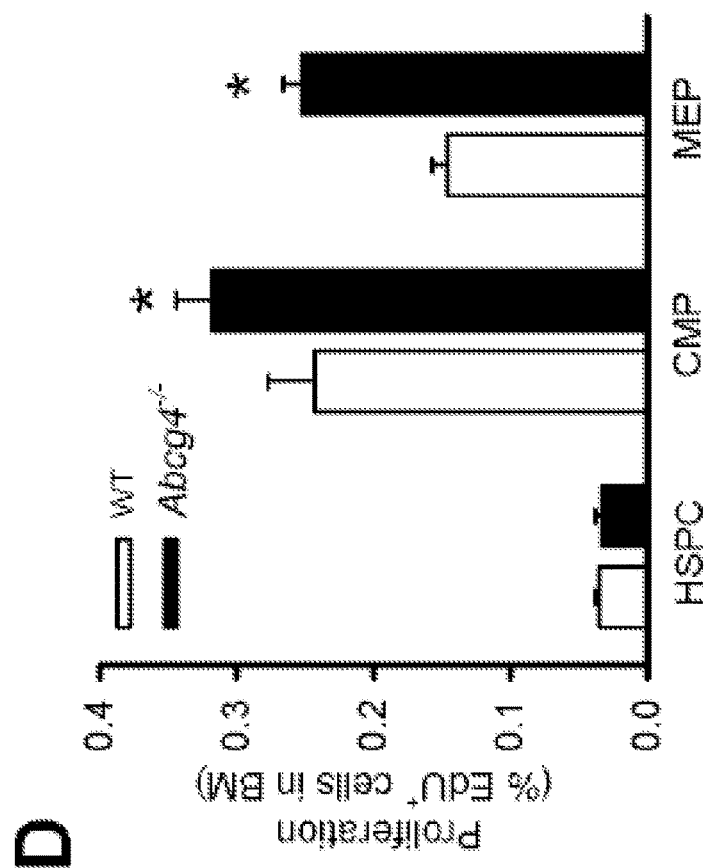
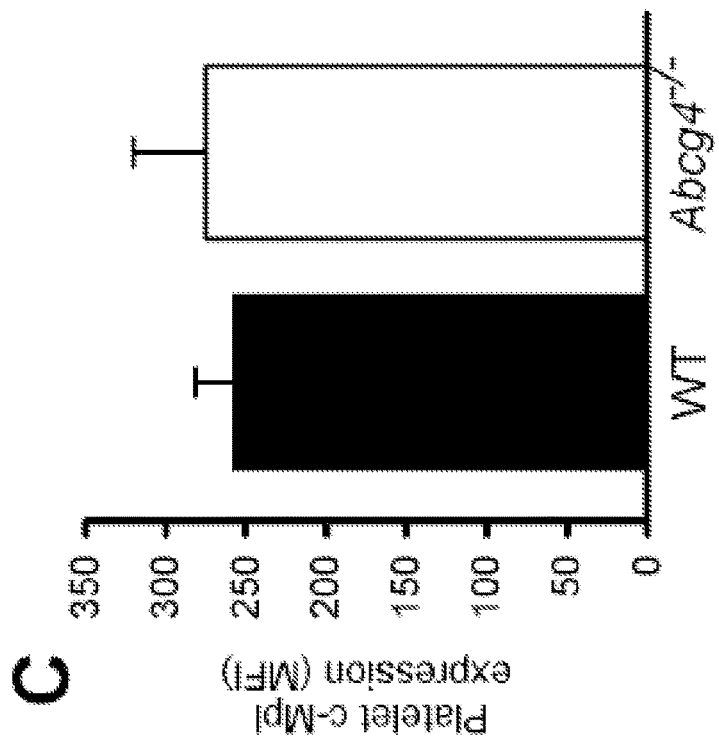
Figures 11C-D.

Figures 13A-B.
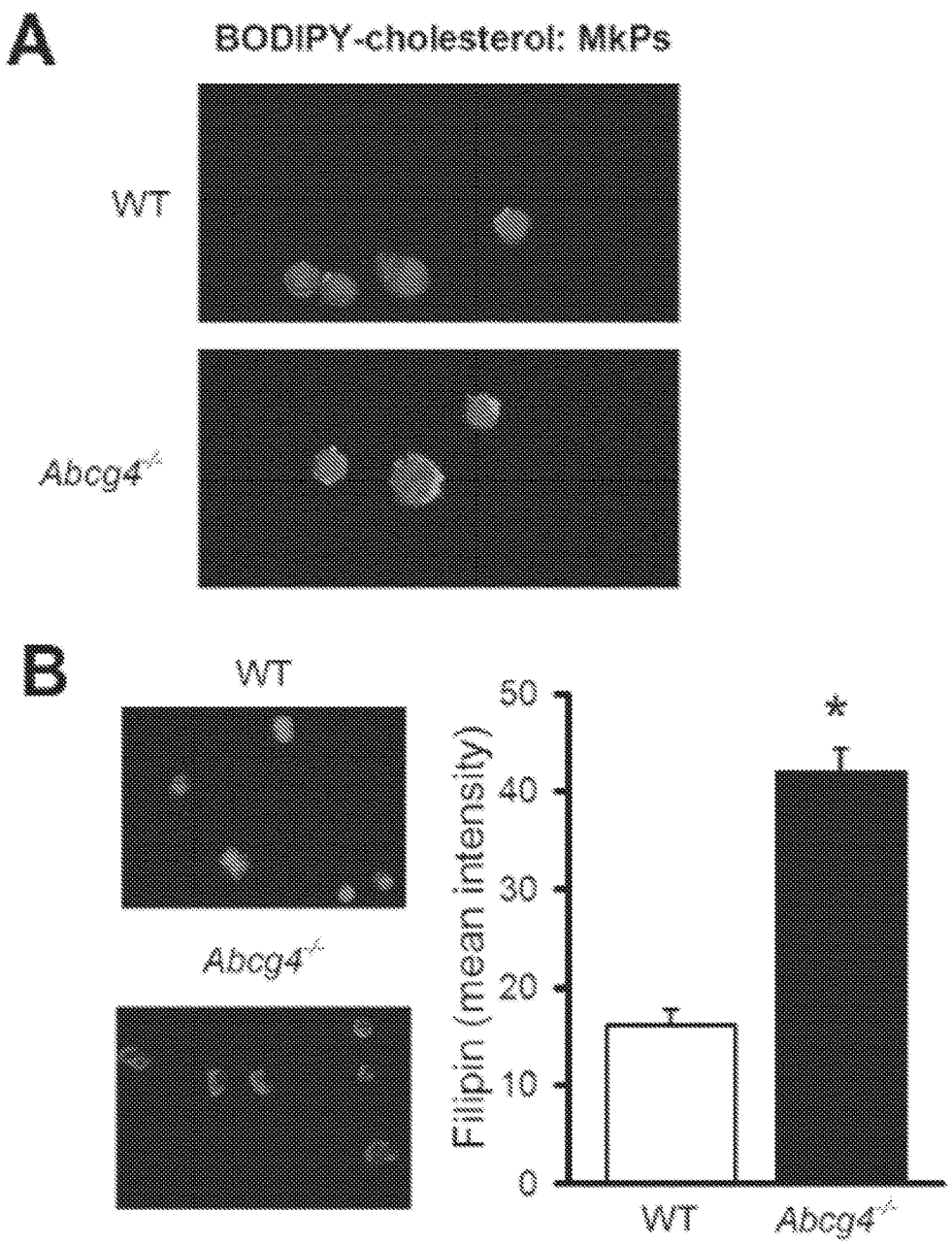

Figures 13C-E.
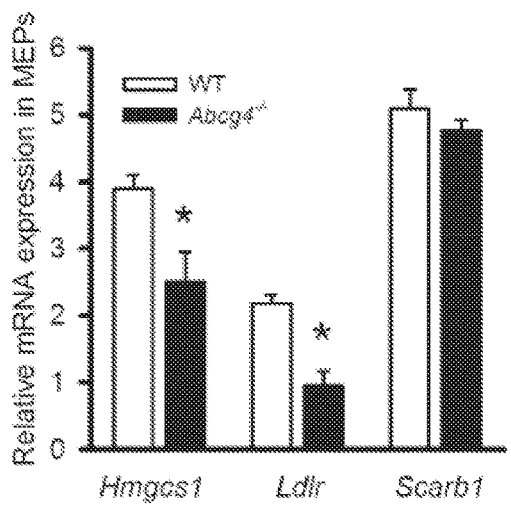
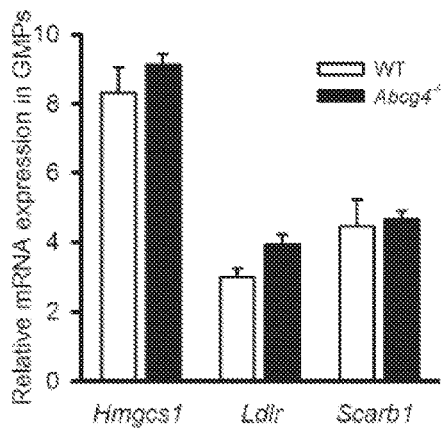
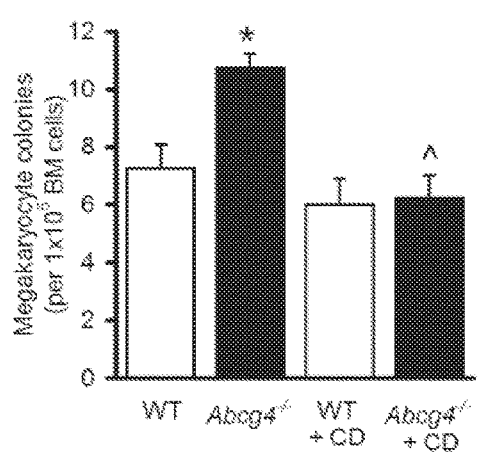

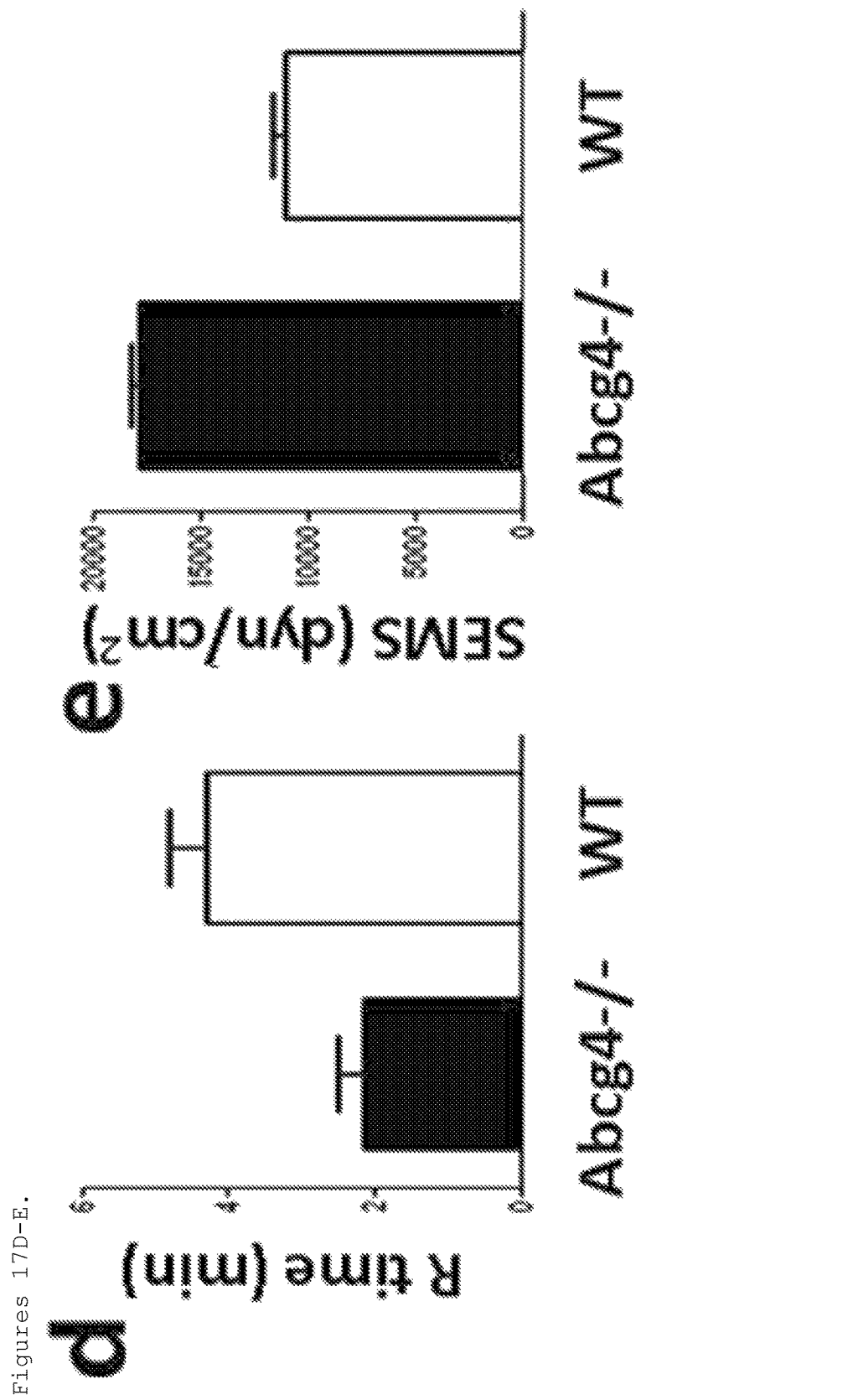
Figures 17D-E.

Figures 18A-B.
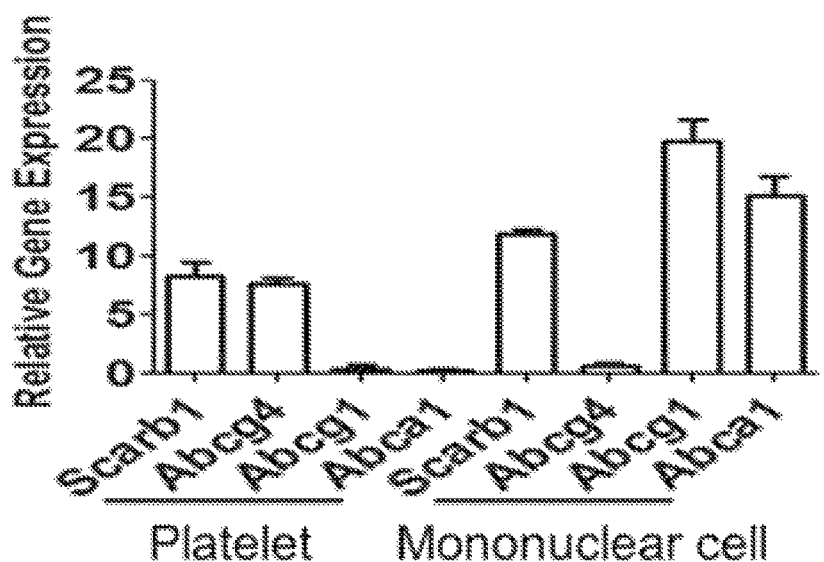
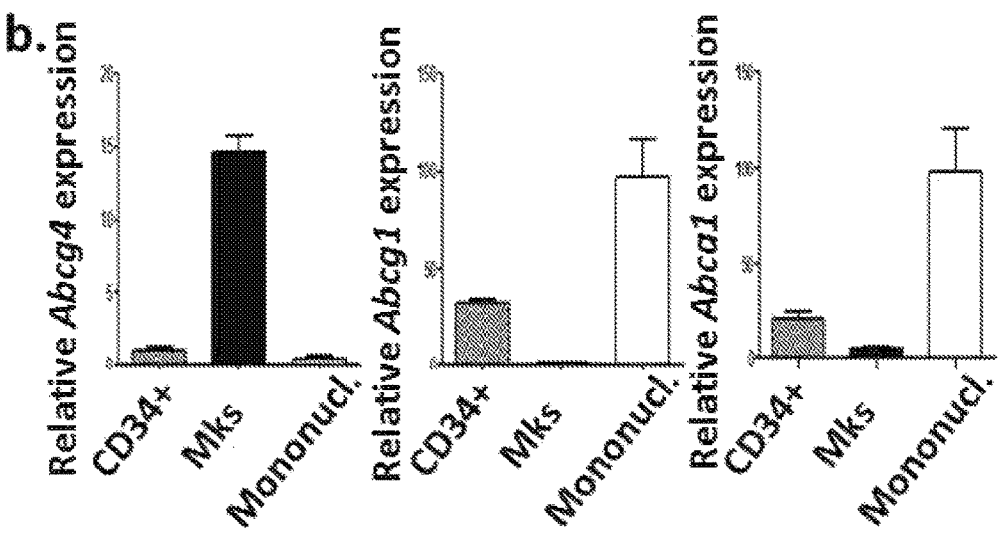

Figures 21A-C.
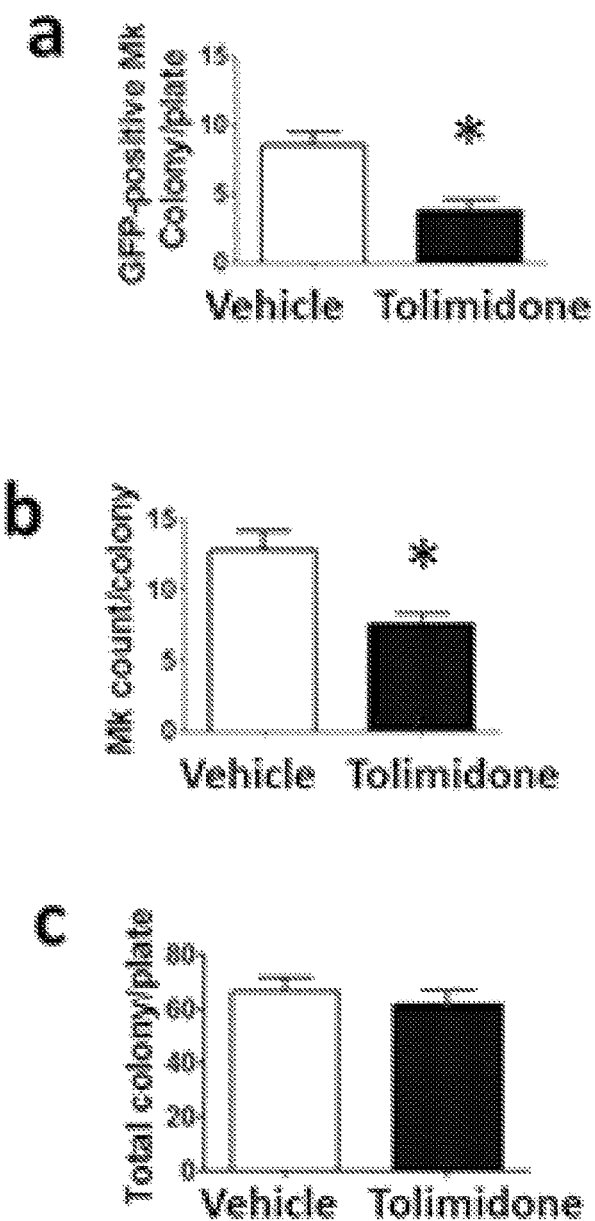

Figures 22A-B.
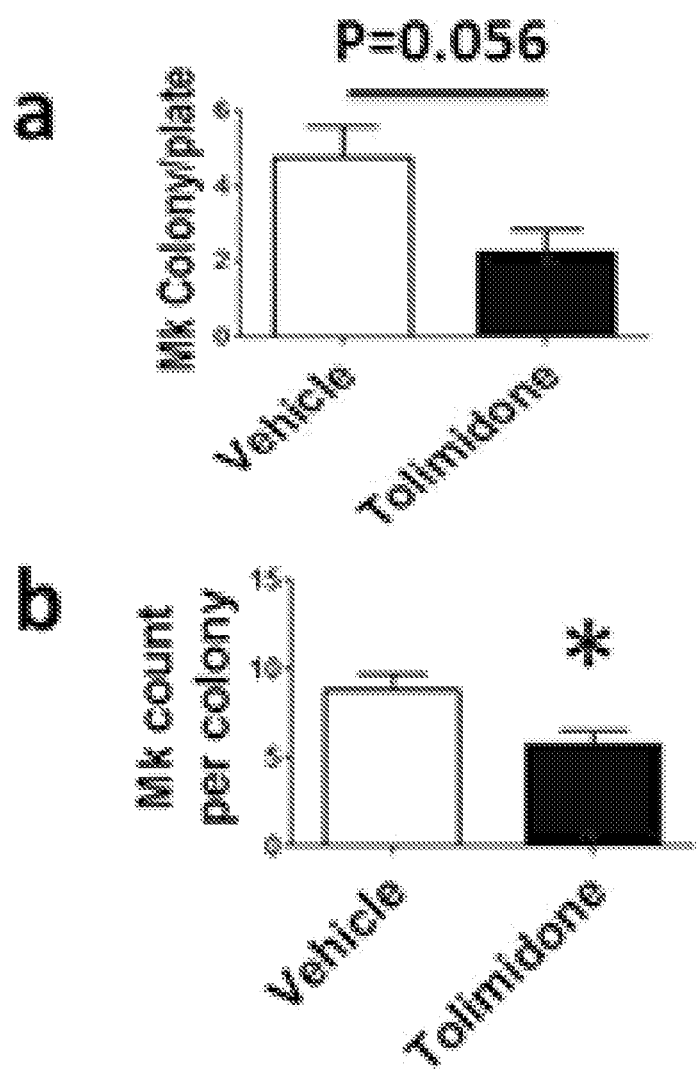

METHODS OF TREATING ATHEROSCLEROSIS OR MYELOPROLIFERATIVE NEOPLASMS BY ADMINISTERING A LYN KINASE ACTIVATOR

This application is a §371 national stage of PCT International Application No. PCT/US2013/077026, filed Dec. 20, 2013, claiming the benefit of U.S. Provisional Application No. 61/740,320, filed Dec. 20, 2013, the contents of each of which are hereby incorporated by reference in their entirety.

The invention was made with government support under Grant number HL102395 awarded by the National Institutes of Health. The government has certain rights in the invention.

Throughout this application, certain publications are referenced in parentheses. Full citations for these publications may be found immediately preceding the claims. The disclosures of these publications in their entireties are hereby incorporated by reference into this application in order to describe more fully the state of the art to which this invention relates.

BACKGROUND OF THE INVENTION

Platelets are involved in all phases of atherogenesis. Platelets interact with arterial endothelial cells, depositing growth factors and chemokines (Koenen, R. R. et al. 2009). Activated platelets or platelet-derived microparticles also activate neutrophils and monocytes and increase the expression of adhesion molecules in these cells (Mause, S. F. et al. 2003; Barry, O. P. et al. 1998). These effects lead to the recruitment of neutrophils and monocyte/macrophages and promote atherosclerotic plaque growth (Koenen, R. R. et al. 2009; Huo, Y. et al. 2003). Platelets also initiate the formation of thrombi on ruptured or eroded atherosclerotic plaques, causing the occlusion of coronary or cerebral arteries and the clinical complications of atherosclerosis (Finn, A. V. et al. 2010). A striking example occurs in myeloproliferative neoplasms (MPN) such as essential thrombocytosis (ET) and primary myelofibrosis (MF), in which increased platelet production is associated with prominent athero-thrombosis (Tefferi, A. et al. 2011). While statins and antiplatelet therapies have revolutionized the treatment of atherosclerotic cardiovascular disease (ACD), substantial residual risk still remains (Kearney, P. M. et al. 2008). Currently, thrombocytosis in ET and MF is treated with low dose aspirin (Michiels, J. J. et al. 2006; Michiels, J. J. 2006), and high risk ET patients are treated with genotoxic agents such as hydroxyurea (Tefferi, A. 2000; Cortelazzo, S. et al. 1995). There remains a need for novel therapies for these MPN patients given their poor overall outcome and limited therapeutic options.

Extensive epidemiological data show an inverse relationship between HDL levels and coronary heart disease (Castelli, W. P. et al. 1977; Gordon, T. et al. 1977). There is convincing evidence indicating a protective role of HDL against atherogenesis in animal models (Tall, A. R. et al. 2008; Duffy, D. et al. 2009). However, the development of new therapies that increase plasma HDL levels has proven challenging. The failure of torcetrapib and dalcetrapib, inhibitors of cholesteryl ester transfer protein that increase HDL levels, and of niacin in clinical trials highlights this (Barter, P. J. et al. 2007; Kastelein, J. J. et al. 2007; Investigators, A. H. et al. 2011). This has fueled interest in better understanding the underlying mechanism responsible for the anti-atherogenic properties of HDL in vivo. In contrast to niacin and CETP inhibitors that raise HDL by reducing catabolism, infusion of cholesterol-poor reconstituted HDL (rHDL) remains a promising approach to reducing coronary atherosclerosis (Michiels, J. J. 2006).

A major hypothesis to explain the protective role of HDL is that it promotes cholesterol efflux from cells in atheroma and reverse cholesterol transport (RCT) (Glomset, J. A. 1980). Importantly, the capacity of HDL-rich plasma to promote macrophage cholesterol efflux may be a strong inverse predictor of coronary disease status, even after adjustment for the HDL cholesterol or apolipoprotein A-I level (Khera, A. V. et al. 2011), supporting increased cholesterol efflux from lesional cells as a mechanism acting against atherosclerosis. Recent studies indicate a key role of ABCA1 and ABCG1 in promoting cellular cholesterol efflux from lesional macrophage foam cells to HDL in the initial step of RCT (Tall, A. R. et al. 2008; Yvan-Charvet, L. et al. 2009). These transporters are also highly expressed in hematopoietic stem and progenitor cells (HSPCs), and in mice lacking ABCA1 and ABCG1, hyper-proliferation of HSPCs leads to monocytosis, neutrophilia and accelerated atherosclerosis (Yvan-Charvet, L. et al. 2010). ABCG4 is highly homologous to ABCG1 (Annilo, T. et al. 2001) and, when overexpressed, promotes cholesterol efflux to HDL in cultured cells (Wang, N. et al. 2004). In contrast to ABCA1 or ABCG1, ABCG4 is not expressed in macrophages and ABCG4 deficiency has no effect on macrophage cholesterol efflux (Wang, N. et al. 2006). Interestingly, ABCG4 is also expressed in hematopoietic tissues such as bone marrow (BM) and fetal liver (Wang, N. et al. 2008; Bojanic, D. D. et al. 2010), but the specific cell population where ABCG4 is expressed and its functions have not been investigated.

In humans, hypercholesterolemia sensitizes platelets to a variety of activating agonists and increases their thrombogenic potential (Carvalho, A. C. e tal. 1974; Davi, G. et al. 1997; Betteridge, D. J. et al. 1994). Increased platelet activation also increases the risk of atherosclerosis (Huo, Y. et al. 2003). Activated platelets release an arsenal of potent inflammatory and mitogenic factors such as platelet factor 4, RANTES, IL-1β. Activated plate (Kaplan, K. L. et al. 1979; Brandt, E. et al. 2000), all with well-documented roles in the initiation or development of atherosclerosis (Koenen, R. R. et al. 2009; Huo, Y. et al. 2003; Sachais, B. S. et al. 2007; Kirii, H. et al. 2003; Lievens, D. et al. 2010). Activated platelets also release vesicular microparticles (Flaumenhaft, R. et al. 2010). These platelet-derived microparticles may contribute to atherosclerosis by activating leukocytes and endothelial cells and facilitating recruitment of leukocytes to lesions (Mause, S. F. et al. 2005; Barry, O. P. et al. 1998). However, the molecular basis for the increased platelet activity associated with hypercholesterolemia is poorly understood. Enrichment of platelets with cholesterol in vitro or in vivo increased platelet reactivity (Shattil, S. J. et al. 1975; Ma, Y. et al. 2010), while cholesterol-poor phospholipid/apoA-1 complexes (rHDL) attenuated platelet activation by promoting cholesterol efflux (Calkin, A. C. et al. 2009). Hypercholesterolemia could also alter platelet reactivity by modulating platelet development and turnover. There is evidence indicating that hypercholesterolemia increases platelet production in human and animal models (Mazoyer, E. et al. 1988; Harker, L. A. et al. 1979; Wessels, P. et al. 1987; Corash, L. et al. 1981), and increased platelet production has been linked to increased numbers of large, RNA-rich and more reactive platelets called reticulated platelets (Karpatkin, S. & Garg, S. K. 1974; Weintraub, A. H. et al. 1974). Hypercholesterolemia could modulate platelet production at early lineage developmental stages involving BM megakaryocyte progenitors (MkP) or megakaryocytes (Mk) (Pathansali, R. et al. 2001; Gomes, A. L. et al. 2010; Dupont, H. et al. 1987; Schick, B. P. et al. 1985) but the relevance to atherosclerosis or atherothrombosis is unknown. Aberrant platelet reactivity as a result of altered platelet production is also suggested by the increased number of hyper-reactive platelets in ET and MF patients (Randi, M. L. et al. 2010; Michiels, J. J. & Berneman, Z. et al. 2006), a finding associated with increased reticulated platelets in these patients as well (Bellucci, S. et al. 2006).

Platelets are produced by Mk in the BM and spleen, and Mks are derived from MkPs while megakaryocyte/erythrocyte progenitor cells (MEPs) give rise to MkPs (Nakorn, T. N. et al. 2003). Thrombopoietin (TPO) is the most important growth factor regulating Mk/platelet lineage development in vivo (Kaushanky, K. et al. 2008). c-MPL is the TPO receptor mediating its signaling (Aushanky, K. et al. 1994). c-MPL-mediated signaling is tightly regulated and recent studies indicate that TPO binding to c-MPL not only initiates cell proliferation but also activates a negative feedback loop involving tyrosine phosphorylation and activation of c-Cbl, an E3 ligase, leading to c-Cbl-mediated ubiquitinylation and degradation of the receptor and limiting c-MPL signaling (Saur, S. J. et al. 2010).

A major breakthrough in studies of MPNs was the identification of mutations of c-MPL and Janus kinase 2 (JAK2), a down-stream signaling kinase, as frequent causes of MPNs (Pikman, Y. et al. 2006; James, C. et al. 2005). The most common form of c-MPL mutations in MPNs occurs on W515, typically replaced by L, K or R amino acid residues (Tefferi, A. 2010). The mutations occur in HSPCs or hematopoietic progenitor cells, resulting in constitutive activation of the receptor or kinase, growth factor independent cell proliferation and a marked increase in the number of terminally differentiated progeny blood cells such as leukocytes, platelets or red blood cells (Tefferi, A. 2010; Jamieson, C. H. et al. 2006).

Tolimidone has been proposed and tested as a treatment of type 2 diabetes (Saporito, M. S. et al. 2012; Ochman, A. R. et al. 2012). The anti-diabetic activity of Tolimidone has been attributed to increasing insulin receptor sensitivity to insulin, probably by promoting phosphorylation of IRS-1.

SUMMARY OF THE INVENTION

The present invention provides a method of treating a subject suffering from atherosclerosis which comprises administering to the subject an amount of a Lyn kinase activator effective to activate Lyn kinase so as to thereby treat the subject.

The present invention provides a method of preventing a disease associated with atherosclerosis in a subject which comprises administering to the subject an amount of a Lyn kinase activator effective to activate Lyn kinase thereby preventing the disease.

The present invention provides a method of treating a subject suffering from a myeloproliferative neoplasm which comprises administering to the subject an amount of a Lyn kinase activator effective to activate Lyn kinase so as to thereby treat the subject.

The present invention provides a method of treating a subject suffering from atherosclerosis or preventing a disease associated with atherosclerosis in a subject which comprises administering to the subject an amount of a compound having the structure:

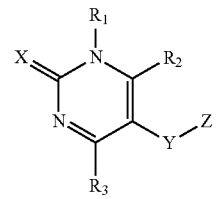

wherein
X is O, S or NH;
Y is O, S, $CH_2$ or NH;
Z is aryl or heteroaryl;
$R_1$ is —H or alkyl;
Each of $R_2$ and $R_3$ is independently —H, —$CF_3$, —CN, —$NO_2$, —$OR_4$, $CO_2R_4$, —$CO_2R_4$, —$NHR_4$, —$NR_4R_4$, alkyl, cycloalkyl, heterocycloalkyl, alkenyl, alkynyl, aryl, alkylaryl, heteroaryl, or halogen, and wherein each $R_4$ is independently —H, alkyl, cycloalkyl, heterocycloalkyl, alkenyl, alkynyl, aryl, alkylaryl, or heteroaryl,
or a pharmaceutically acceptable salt or ester thereof, in an amount effective to activate Lyn kinase.

The present invention provides a method of treating a subject suffering from a myeloproliferative neoplasm which comprises administering to the subject an effective amount of a composition comprising a compound having the structure:

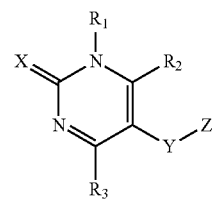

wherein
X is O, S or NH;
Y is O, S, $CH_2$ or NH;
Z is aryl or heteroaryl;
$R_1$ is —H or alkyl;
Each of $R_2$ and $R_3$ is independently —H, —$CF_3$, —CN, —$NO_2$, —$OR_4$, $CO_2R_4$, —$CO_2R_4$, —$NHR_4$, —$NR_4R_4$, alkyl, cycloalkyl, heterocycloalkyl, alkenyl, alkynyl, aryl, alkylaryl, heteroaryl, or halogen, and
wherein each $R_4$ is independently —H, alkyl, cycloalkyl, heterocycloalkyl, alkenyl, alkynyl, aryl, alkylaryl, or heteroaryl,
or a pharmaceutically acceptable salt or ester thereof, in an amount effective to activate Lyn kinase.

BRIEF DESCRIPTION OF THE FIGURES

FIG. 3. Shown are results all from WT, Abcg4$^{-/-}$ or Lyn$^{-/-}$ MkPs (n=4). (A) Quantification of tyrosine-phosphorylated c-CBL in response to TPO. (B) Tyrosine-phosphorylated c-CBL levels 5 min after TPO treatment and with or without pretreatment with CD (3 mM), CD-chol (3 mM CD) for 30 min or rHDL (20 μg apoA-I/ml) for 2 hours. (C) Tyrosine-phosphorylated c-CBL with or without 5 min TPO treatment or SU6656 pretreatment (10 μg/ml for 2 h). (D) Cell surface c-MPL with or without TPO or SU6656 treatment for 2 h. (E) Tyrosine-phosphorylated c-CBL (5 min in response to TPO). (F) cell surface c-MPL (2 h TPO treatment) with or without pretreatment with CD-chol (3 mM CD) for 30 min. (G) 16 h EdU incorporation in the presence of TPO and with or without CD (3 mM), CD-Chol (3 mM CD) pretreatment for 30 min or rHDL (20 μg/ml) for 16 h. (H) p-STAT-5 and p-ERK1/2 levels with or without TPO for 10 minutes. TPO was 30 ng/ml for all the assays shown. Error bars are S.E.M. *P<0.05 WT vs Abcg4$^{-/-}$ TPO and ^P<0.05 for treatment effect.

FIG. 5. Irradiated Ldlr$^{-/-}$ mice (n=12/group) were transplanted with donor BM cells from WT or Abcg4$^{-/-}$ mice and fed a WTD diet for 12 weeks. (A) Representative of H&E-stained of the proximal aortas (original magnification 40×). (B) HDL, (C) non-HDL cholesterol and (D) triglyceride levels. (E) Peripheral white blood cell, (F) monocyte, (G) red blood cell (H) and reticulocyte counts. (I) Platelet counts in WTD-fed Ldlr$^{-/-}$ recipient mice 5 days after vehicle or rHDL (100 mg apoA-I/kg BW) infusion (n=5). Error bars are S.E.M. *P<0.05 WT versus Abcg4$^{-/-}$ and ^P<0.05 for treatment effect.

FIG. 7. Platelets from WT and Abcg4$^{-/-}$ mice fed the chow diet were isolated and used to determine (A) percentage cholesterol efflux and (B) cholesterol content.

FIG. 8. Flow cytometry analysis of BM LSK, GMP, CMP and MEP populations.

FIG. 11. (A) Plasma TPO levels from the WTD-fed female WT or Abcg4$^{-/-}$ BMT Ldlr$^{-/-}$ mice (n=10) were determined by ELISA. Cell surface c-MPL levels from (B) BM megakaryocyte or (C) platelets of the WTD-fed female WT or Abcg4$^{-/-}$ BMT Ldlr–/– mice (n=3) were determined by flow cytometry. (D) Cell proliferation assessed by EdU incorporation for 16 h into BM cell populations from Chow-fed mice (n=5). Error bars are S.E.M. *P<0.05.

FIG. 13. (A) Fluorescence confocal microscopy of WT or Abcg4$^{-/-}$ MkPs treated with CD/Bodipy-cholesterol (0.03 mM CD) for 30 min and (B) confocal microscopy and quantification of fillipin stained WT or Abcg4$^{-/-}$ MkPs. Gene expression was determined by q-PCR in (C) MEPs or (D) GMPs from the WT or Abcg4$^{-/-}$ BM Ldlr$^{-/-}$ recipient mice (n=5) fed WTD for 12 weeks. Error bars are S.D (n=10). *P<0.05. (E) MK-CFU assays using total BM cells from WT or Abcg4$^{-/-}$ mice with or without pretreatment with CD (3 mM) for 30 minutes. Error bars are S.E.M. *P<0.05.

DETAILED DESCRIPTION OF THE INVENTION

Figure 1A:
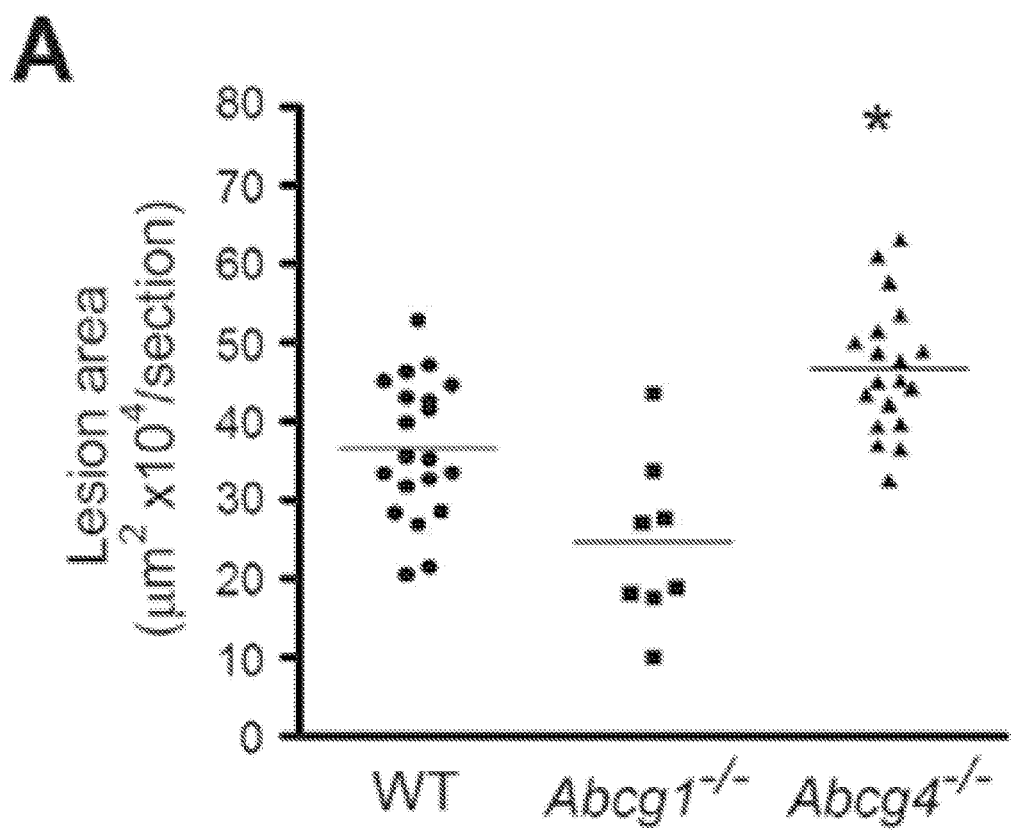
FIG. 1. $Ldlr^{-/-}$ mice were transplanted with donor BM cells from WT, $Abcg4^{-/-}$, $Abcg1^{-/-}$ or $Abca1^{-/-}Abcg1^{-/-}$ mice and fed a WTD diet for 12 weeks. (A) Quantification of proximal aortic root lesion area (individual and mean) by morphometric analysis of H&E-stained sections. (B) Representative of LacZ stained proximal aortas from mice receiving $Abca1^{-/-}Abcg1^{-/-}$ or $Abcg4^{-/-}$ BM. Original magnification 40×. (C) Platelet counts from mice receiving WT or $Abcg4^{-/-}$ BM. Error bars are S.E.M (n=12). Shown is the representative of four studies with similar results. (D) Cell surface CD11b levels of platelet-associated Ly6C$^{hi}$ and neutrophils in WTD-fed Ldlr$^{-/-}$ mice transplanted with WT or Abcg4$^{-/-}$ BM cells. (E) Plasma platelet-derived microparticle and (F) percentage reticulated platelets levels in WTD-fed Ldlr$^{-/-}$ recipient mice. (G) Platelet adhesion and aggregation to collagen under shear flow with blood from WTD-fed Ldlr$^{-/-}$ recipient mice. (H) FeCl$_3$ induced carotid artery thrombosis in vivo in WTD-fed Ldlr$^{-/-}$ recipient mice. *P<0.05 between genotypes. ^P<0.05 between the basal and treatment.

The present invention provides a method of treating a subject suffering from atherosclerosis which comprises administering to the subject an amount of a Lyn kinase activator effective to activate Lyn kinase so as to thereby treat the subject.

The present invention provides a method of preventing a disease associated with atherosclerosis in a subject which comprises administering to the subject an amount of a Lyn kinase activator effective to activate Lyn kinase thereby preventing the disease.

In some embodiments, the method wherein the disease associated with atherosclerosis is atherothrombosis, coronary heart disease, deep venous thrombosis, carotid artery disease, angina pectoris, peripheral arterial disease, chronic kidney disease, acute coronary syndrome, vascular stenosis, myocardial infarction, aneurysm, or stroke.

In some embodiments, the method wherein the atherosclerosis is caused by aberrant megakaryopoiesis, increased platelet production, increased platelet count, or increased platelet activation.

In some embodiments, the method wherein the amount of the Lyn kinase activator reduces platelet production in the subject.

In some embodiments, the method wherein the amount of the Lyn kinase activator reduces platelet count in the subject.

In some embodiments, the method wherein the amount of the Lyn kinase activator reduces platelet activation in the subject.

In some embodiments, the method wherein the amount of the Lyn kinase activator reduces megakaryopoiesis in the subject.

In some embodiments, the method wherein the amount of the Lyn kinase activator reduces c-MPL(W515L)-induced megakaryopoiesis in the subject.

In some embodiments, the method wherein the amount of the Lyn kinase activator reduces JACK2(V671F)-induced megakaryopoiesis in the subject.

In some embodiments, the method wherein the amount of the Lyn kinase activator suppresses the proliferation of megakaryocyte progenitor cells in the subject.

In some embodiments, the method wherein the subject also suffers from hypercholesterolemia.

The present invention provides a method of treating a subject suffering from a myeloproliferative neoplasm which comprises administering to the subject an amount of a Lyn kinase activator effective to activate Lyn kinase so as to thereby treat the subject.

In some embodiments, the method wherein wherein the myeloproliferative neoplasm is essential thrombocytosis (ET) or primary myelofibrosis (MF).

In some embodiments, the method wherein the subject's chromosomes comprise a JAK2 mutation.

In some embodiments, the method further comprising administering a JAK2 inhibitor to the subject.

In some embodiments, the method wherein the Lyn kinase activator is a compound having the structure:

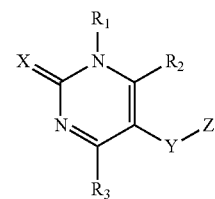

wherein
X is O, S or NH;
Y is O, S, CH$_2$ or NH;
Z is aryl or heteroaryl;
R$_1$ is —H or alkyl;
Each of R$_2$ and R$_3$ is independently —H, —CF$_3$, —CN, —NO$_2$, —OR$_4$, CO$_2$R$_4$, —CO$_2$R$_4$, —NHR$_4$, —NR$_4$R$_4$, alkyl, cycloalkyl, heterocycloalkyl, alkenyl, alkynyl, aryl, alkylaryl, heteroaryl, or halogen, and wherein each R$_4$ is independently —H, alkyl, cycloalkyl, heterocycloalkyl, alkenyl, alkynyl, aryl, alkylaryl, or heteroaryl, or a pharmaceutically acceptable salt or ester thereof.

In some embodiments, the method wherein Z is phenyl, pyridine, or pyrimidine, unsubstituted or substituted, or a pharmaceutically acceptable salt o ester thereof.

In some embodiments, the method wherein Z is a compound having the structure:

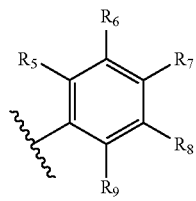

wherein each of R$_5$, R$_6$, R$_7$, R$_8$ and R$_9$ is independently —H, —CF$_3$, —CN, —NO$_2$, —OR$_{10}$, CO$_2$R$_{10}$, —CO$_2$R$_{10}$, —NHR$_{10}$, —NR$_{10}$R$_{10}$, alkyl, cycloalkyl, heterocycloalkyl, alkenyl, alkynyl, aryl, alkylaryl, heteroaryl, or halogen, and wherein each R$_{10}$ is independently —H, alkyl, cycloalkyl, heterocycloalkyl, alkenyl, alkynyl, aryl, alkylaryl, or heteroaryl, or a pharmaceutically acceptable salt or ester thereof.

In some embodiments, the method wherein Z is a compound having the structure:

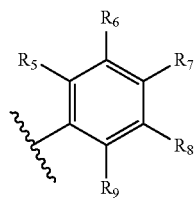

wherein each of R$_5$, R$_6$, R$_7$, R$_8$ and R$_9$ is —H, —CH$_3$, —Cl, —F, —OH, —CF$_3$, or —NH$_2$, or a pharmaceutically acceptable salt or ester thereof.

In some embodiments, the method wherein Z is

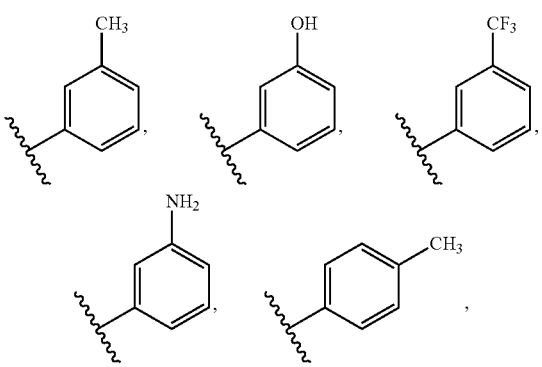

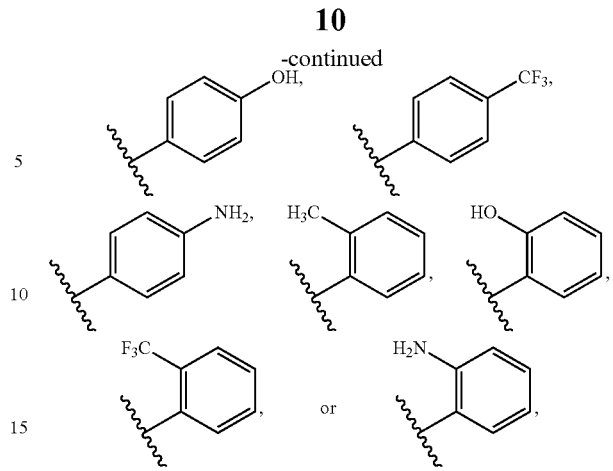

or a pharmaceutically acceptable salt or ester thereof.

In some embodiments, the method wherein each of X and Y is O, or a pharmaceutically acceptable salt or ester thereof.

In some embodiments, the method wherein each of R$_1$, R$_2$ and R$_3$ is —H, or a pharmaceutically acceptable salt or ester thereof.

In some embodiments, the method wherein the Lyn kinase activator is a compound having the structure:

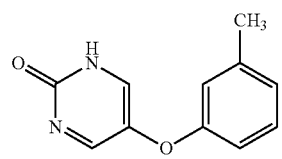

or a pharmaceutically acceptable salt or ester thereof.

In some embodiments, the method wherein the Lyn kinase activator is a compound having the structure:

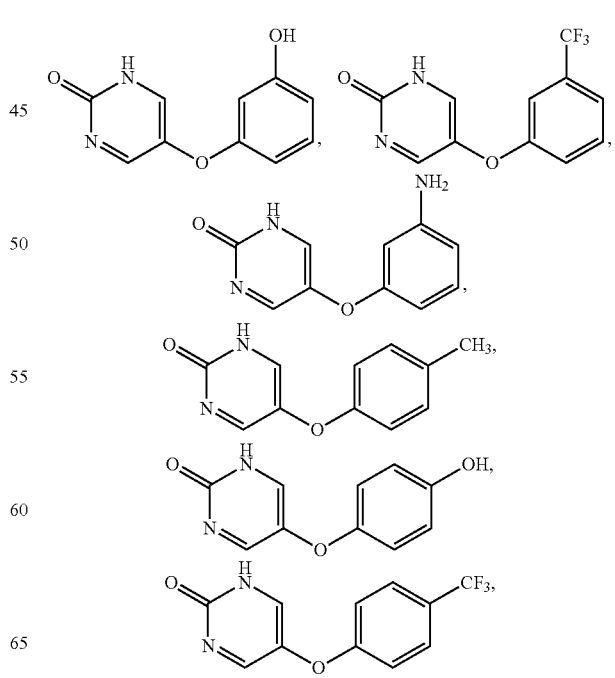

-continued

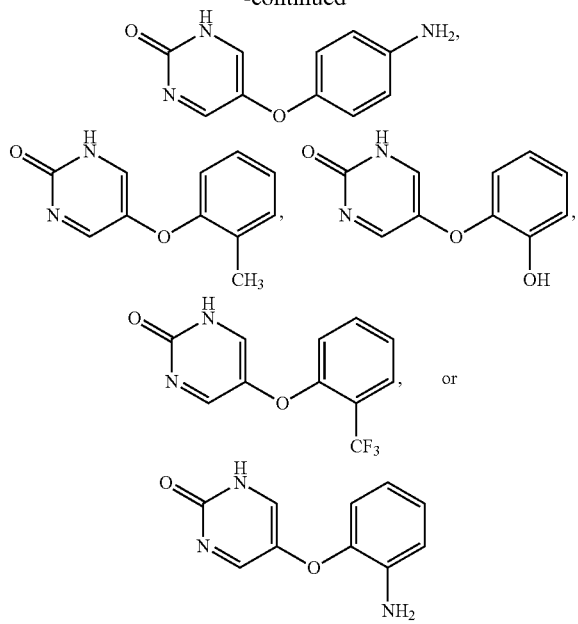

or a pharmaceutically acceptable salt or ester thereof.

The present invention provides a method of treating a subject suffering from atherosclerosis or preventing a disease associated with atherosclerosis in a subject which comprises administering to the subject an amount of a a compound having the structure:

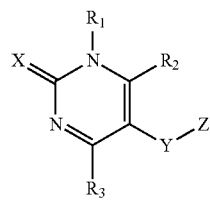

wherein
X is O, S or NH;
Y is O, S, $CH_2$ or NH;
Z is aryl or heteroaryl;
$R_1$ is —H or alkyl;
Each of $R_2$ and $R_3$ is independently —H, —$CF_3$, —CN, —$NO_2$, —$OR_4$, $CO_2R_4$, —$CO_2R_4$, —$NR_4R_4$, alkyl, cycloalkyl, heterocycloalkyl, alkenyl, alkynyl, aryl, alkylaryl, heteroaryl, or halogen, and
wherein each $R_4$ is independently —H, alkyl, cycloalkyl, heterocycloalkyl, alkenyl, alkynyl, aryl, alkylaryl, or heteroaryl,
or a pharmaceutically acceptable salt or ester thereof, in an amount effective to activate Lyn kinase.

In some embodiments, the method wherein the disease associated with atherosclerosis is atherothrombosis, coronary heart disease, deep venous thrombosis, carotid artery disease, angina pectoris, peripheral arterial disease, chronic kidney disease, acute coronary syndrome, vascular stenosis, myocardial infarction, aneurysm or stroke.

The present invention provides a method of treating a subject suffering from a myeloproliferative neoplasm which comprises administering to the subject an effective amount of a composition comprising a compound having the structure:

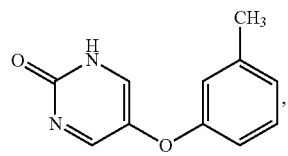

wherein
X is O, S or NH;
Y is O, S, $CH_2$ or NH;
Z is aryl or heteroaryl;
$R_1$ is —H or alkyl;
Each of $R_2$ and $R_3$ is independently —H, —$CF_3$, —CN, —$NO_2$, —$OR_4$, $CO_2R_4$, —$CO_2R_4$, —$NHR_4$, —$NR_4R_4$, alkyl, cycloalkyl, heterocycloalkyl, alkenyl, alkynyl, aryl, alkylaryl, heteroaryl, or halogen, and
wherein each $R_4$ is independently —H, alkyl, cycloalkyl, heterocycloalkyl, alkenyl, alkynyl, aryl, alkylaryl, or heteroaryl,
or a pharmaceutically acceptable salt or ester thereof, in an amount effective to activate Lyn kinase.

In some embodiments, the method wherein the compound has the structure:

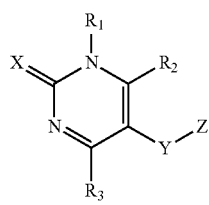

or a pharmaceutically acceptable salt or ester thereof.

In some embodiments, a Lyn kinase activator for use in treating a subject suffering from atherosclerosis which comprises administering to the subject an amount of a Lyn kinase activator effective to activate Lyn kinase so as to thereby treat the subject.

In some embodiments, a Lyn kinase activator for use in preventing a disease associated with atherosclerosis in a subject which comprises administering to the subject an amount of a Lyn kinase activator effective to activate Lyn kinase thereby preventing the disease.

In some embodiments, a Lyn kinase activator for use in treating a subject suffering from a myeloproliferative neoplasm which comprises administering to the subject an amount of a Lyn kinase activator effective to activate Lyn kinase so as to thereby treat the subject.

In one embodiment, the JAK2 inhibitor is Lestaurtinib, Tofacitinib, Ruxolitinib, Pacritinib, CYT387, Baricitinib, or TG101348 (SAR302503).

In one embodiment, the subject is a mammal. In another embodiment, the mammal is human.

As used herein, "atherosclerosis" refers to cardiovascular disease characterized by the deposition of arterial plaques on the innermost layer of the walls of arteries resulting in the narrowing and hardening of the arteries. The arterial plaque is an accumulation of macrophage cells or debris, and contains lipids (cholesterol and fatty acids), calcium and a variable amount of fibrous connective tissue.

Diseases associated with atherosclerosis include, but are not limited to, atherothrombosis, coronary heart disease, deep venous thrombosis, carotid artery disease, angina pectoris, peripheral arterial disease, chronic kidney disease, acute coronary syndrome, vascular stenosis, myocardial infarction, aneurysm or stroke.

As used herein, "myeloproliferative neoplasm" refers to a disease, i.e., blood cancer, characterized by the overproduction of any combination of white blood cells, red blood cells or platelets.

Myeloproliferative neoplasms include, but are not limited to essential thrombocytosis (ET) or primary myelofibrosis (MF)

Except where otherwise specified, when the structure of a compound of the method of the present invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, NY, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^{1}H$, $^{2}H$, or $^{3}H$. Furthermore, any compounds containing $^{2}H$ or $^{3}H$ may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

The term "substitution", "substituted" and "substituent" refers to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and halogens (i.e., F, Cl, Br, and I); alkyl groups, such as methyl, ethyl, n-propyl, isopropryl, n-butyl, tert-butyl, and trifluoromethyl; hydroxyl; alkoxy groups, such as methoxy, ethoxy, n-propoxy, and isopropoxy; aryloxy groups, such as phenoxy; arylalkyloxy, such as benzyloxy (phenylmethoxy) and p-trifluoromethylbenzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

In the compounds used in the method of the present invention, the substituents may be substituted or unsubstituted, unless specifically defined otherwise.

In the compounds used in the method of the present invention, alkyl, cycloalkyl, heterocycloalkyl, alkenyl, alkynyl, aryl, alkylaryl, and heteroaryl groups can be further substituted by replacing one or more hydrogen atoms with alternative non-hydrogen groups. These include, but are not limited to, halo, hydroxy, mercapto, amino, carboxy, cyano and carbamoyl.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

In choosing the compounds used in the method of the present invention, one of ordinary skill in the art will recognize that the various substituents, i.e. $R_1$, $R_2$, etc. are to be chosen in conformity with well-known principles of chemical structure connectivity.

As used herein, "alkyl" includes both branched and straight-chain saturated aliphatic hydrocarbon groups having the specified number of carbon atoms and may be unsubstituted or substituted. Thus, $C_1$-$C_n$ as in "$C_1$-$C_n$ alkyl" is defined to include groups having 1, 2, . . . , n–1 or n carbons in a linear or branched arrangement. For example, $C_1$-$C_6$, as in "$C_1$-$C_6$ alkyl" is defined to include groups having 1, 2, 3, 4, 5, or 6 carbons in a linear or branched arrangement, and specifically includes methyl, ethyl, n-propyl, isopropyl, n-butyl, t-butyl, pentyl, and hexyl. Unless otherwise specified contains one to ten carbons. Alkyl groups can be unsubstituted or substituted with one or more substituents, including but not limited to halogen, alkoxy, alkylthio, trifluoromethyl, difluoromethyl, methoxy, and hydroxyl.

As used herein, "alkenyl" refers to a non-aromatic hydrocarbon radical, straight or branched, containing at least 1 carbon to carbon double bond, and up to the maximum possible number of non-aromatic carbon-carbon double bonds may be present, and may be unsubstituted or substituted. For example, "$C_2$-$C_6$ alkenyl" means an alkenyl radical having 2, 3, 4, 5, or 6 carbon atoms, and up to 1, 2, 3, 4, or 5 carbon-carbon double bonds respectively. Alkenyl groups include ethenyl, propenyl, butenyl and cyclohexenyl.

As used herein, "heteroalkyl" includes both branched and straight-chain saturated aliphatic hydrocarbon groups having at least 1 heteroatom within the chain or branch.

As used herein, "cycloalkyl" includes cyclic rings of alkanes of three to eight total carbon atoms, or any number within this range (i.e., cyclopropyl, cyclobutyl, cyclopentyl, cyclohexyl, cycloheptyl or cyclooctyl).

As used herein, "heterocycloalkyl" is intended to mean a 5- to 10-membered nonaromatic ring containing from 1 to 4 heteroatoms selected from the group consisting of O, N and S, and includes bicyclic groups. "Heterocyclyl" therefore includes, but is not limited to the following: imidazolyl, piperazinyl, piperidinyl, pyrrolidinyl, morpholinyl, thiomorpholinyl, tetrahydropyranyl, dihydropiperidinyl, tetrahydrothiophenyl and the like. If the heterocycle contains nitrogen, it is understood that the corresponding N-oxides thereof are also encompassed by this definition.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include but are not limited to: phenyl, p-toluenyl (4-methylphenyl), naphthyl, tetrahydro-naphthyl, indanyl, phenanthryl, anthryl or acenaphthyl. In cases where the aryl substituent is bicyclic and one ring is non-aromatic, it is understood that attachment is via the aromatic ring.

The term "alkylaryl" refers to alkyl groups as described above wherein one or more bonds to hydrogen contained therein are replaced by a bond to an aryl group as described above. It is understood that an "alkylaryl" group is connected to a core molecule through a bond from the alkyl group and that the aryl group acts as a substituent on the alkyl group. Examples of arylalkyl moieties include, but are not limited to, benzyl (phenylmethyl), p-trifluoromethylbenzyl (4-trifluoromethylphenylmethyl), 1-phenylethyl, 2-phenylethyl, 3-phenylpropyl, 2-phenylpropyl and the like.

The term "heteroaryl" as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include but are not limited to phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "phenyl" is intended to mean an aromatic six membered ring containing six carbons, and any substituted derivative thereof.

The term "pyridine" is intended to mean a heteroaryl having a six-membered ring containing 5 carbon atoms and 1 nitrogen atom, and any substituted derivative thereof.

The term "pyrimidine" is intended to mean a heteroaryl having a six-membered ring containing 4 carbon atoms and 2 nitrogen atoms, and any substituted derivative thereof.

The compounds used in the method of the present invention may be prepared by techniques well know in organic synthesis and familiar to a practitioner ordinarily skilled in the art. However, these may not be the only means by which to synthesize or obtain the desired compounds.

The compounds used in the method of the present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) 5$^{th}$ Edition (1996), March's Advanced Organic Chemistry: Reactions, Mechanisms, and Structure, Michael B. Smith, Jerry March, (Wiley-Interscience) 5$^{th}$ Edition (2007), and references therein, which are incorporated by reference herein. However, these may not be the only means by which to synthesize or obtain the desired compounds.

The compounds used in the method of the present invention may be purchased from a chemical supplier, including Sigma-Aldrich, St. Louis, Mo., USA. However, this may not be the only means by which to synthesize or obtain the desired compounds.

The Tolimidone (also known as MLR 1023) used in the method of the present invention may be purchased from Sigma-Aldrich, St. Louis, Mo., USA (MLR 1023: Catalog No. SML0371) or Activate Scientific, Germany (Catalog No. AS9568).

The various R groups attached to the aromatic rings of the compounds disclosed herein may be added to the rings by standard procedures, for example those set forth in Advanced Organic Chemistry: Part B: Reaction and Synthesis, Francis Carey and Richard Sundberg, (Springer) 5th ed. Edition. (2007), the content of which is hereby incorporated by reference.

Another aspect of the invention comprises a compound used in the method of the present invention as a pharmaceutical composition.

As used herein, the term "pharmaceutically active agent" means any substance or compound suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department Of Health And Human Services, 30$^{th}$ edition, 2010), which are hereby incorporated by reference. Pharmaceutically active agents which have pendant carboxylic acid groups may be modified in accordance with the present invention using standard esterification reactions and methods readily available and known to those having ordinary skill in the art of chemical synthesis. Where a pharmaceutically active agent does not possess a carboxylic acid group, the ordinarily skilled artisan will be able to design and incorporate a carboxylic acid group into the pharmaceutically active agent where esterification may subsequently be carried out so long as the modification does not interfere with the pharmaceutically active agent's biological activity or effect.

The compounds used in the method of the present invention may be in a salt form. As used herein, a "salt" is a salt of the instant compounds which has been modified by making acid or base salts of the compounds. In the case of compounds used to treat an infection or disease caused by a pathogen, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

As used herein, "treating" encompasses, e.g., inducing inhibition, regression, or stasis of a disease or disorder, or lessening, suppressing, inhibiting, reducing the severity of, eliminating or substantially eliminating, or ameliorating a symptom of the disease or disorder.

The compounds used in the method of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise a single compound or mixtures thereof with additional antibacterial agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or onto a site of infection, all using dosage forms well known to those of ordinary skill in the pharmaceutical arts.

The compounds used in the method of the present invention can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present invention may also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropyl-methacrylamide-phenol, polyhydroxyethylasparta-midephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials to make them compatible with the type of injection or delivery system chosen.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Abbreviations

ABC, ABC-binding cassette transporter; ACD, Atherosclerotic cardiovascular disease; BM, Bone marrow; BMT, bone marrow transplantation; CMP, Common myeloid progenitor cell; ET, Essential thrombocytosis; Gata1-HRD, Gata1-hematopoietic regulatory domain; GMP, Granulocyte/monocyte progenitor cell; HDL, High density lipoprotein; HSPCs, Hematopoietic stem and progenitor cell; ITP, Immune thrombocytopenia; JAK2, Janus kinase 2; Ldlr, Low density lipoprotein receptor; LSK, Lineage-negative (Lin−), Sca-1+, c-Kit+ cell; MEP, Megakaryocyte/erythrocyte progenitor cell, MF, Primary myelofibrosis; Mk, Megakaryocyte; MkP, Megakaryocyte progenitor cells; c-MPL, Thrombopoietin receptor; MPN, Myeloproliferative neoplasms; PF4, Platelet factor 4; PS, phosphatidylserine; rHDL, Cholesterol-poor apoA-I/phospholipid complex; q-PCR, Quantitative real-time RT-PCR; SKF, Src family kinase; SR-BI, Scavenger receptor class B member 1; TEG, Thrombelastography; TPO, Thrombopoietin; WTD, High fat hifh cholesterol diet; WT, Wild type.

Materials and Methods

Mice and Treatments $Abcg4^{-/-}$, Abcg1 $Abca1^{-/-}$, and $Abcg1^{-/-}$ mice were created as described (Wang, N. et al. 2006; Yvan-Charvet, L. et al. 2010) and used in this study.

Abcg4$^{-/-}$ mice have been backcrossed onto C57BL6/J mice for more than 10 generations. WT (C57BL/6J) and Ldlr$^{-/-}$ (B6.12957-Ldlrtm1Her) were obtained from The Jackson Laboratory (Bar Harbor, Me.). For BM transplantation studies, BM from WT, Abcg4$^{-/-}$, Abcg1$^{-/-}$ Abca1$^{-/-}$, or Abcg1$^{-/-}$ mice was transplanted into WT or Ldlr$^{-/-}$ recipient mice as described. For atherosclerosis studies, the BM transplanted recipient mice were fed a Western diet (TD88137; Harlan Teklad) for the indicated period of time. BM specific retroviral expression of murine MPL(W515L) was established as described (Koppikar, P. et al. 2010), using WT C57BL6/J mice as the recipient and WT C57BL6/J or Abcg4$^{-/-}$ mice as the BM donor. Where indicated, vehicle (saline), rHDL, or TPO (R&D Systems) was injected at the indicted dose into the mice via the tail vein. The rHDL (CSL-111) was provided by CSL Behring AG, Bern, Switzerland; CSL-111 is comprised of human apoA-I and phosphatidylcholine from soy bean in a ratio of 1:150.

Femur and tibia of Lyn$^{-/-}$ mice used to prepare Lyn$^{-/-}$ BM cells were kindly provided by Dr. Anthony L. DeFranco of University of California, San Francisco. The mice were created as described (Chan, V. W. et al. 1997) and backcrossed at least 15 generations onto C57BL/6 background.

Histochemistry

Tissues and proximal aortas were serially paraffin sectioned and stained with H&E for morphological analysis as described[2]. Aortic lesion size of each animal was calculated as the mean of lesion areas in 5 sections from the same mouse. Bone samples were decalcified with EDTA solution prior to cryosectioning. Von Willibrand Factor antibody (Dako, Catalog #A0082) was used to stain MKs. Lac-Z staining of frozen sections of mouse bone, spleen or proximal aorta was carried out using β-Galactosidase Staining Kit (Cell Signaling Technology, Danvers, Mass.).

Complete Blood Count (CBC)

CBCs were quantified using whole blood collected from the tail bleeding. FORCYTE Veterinary Hematology Analyzer (Oxford Science, Inc.) was used for the analysis.

Plasma and Cellular Lipids

Plasma lipoprotein cholesterol and triglyceride levels were determined by colorimetric enzymatic assays, using the assay kits from Wako Diagnostics (Japan). Platelets were isolated from platelets-rich plasma, which was prepared from a low-speed spin of EDTA-treated mouse plasma, and platelet cholesterol content was measured by gas chromatography following lipid extraction.

Cholesterol Efflux

For platelet cholesterol efflux, platelets were isolated from platelet-rich plasma by centrifugation at ~3500 rpm for 10 minutes in an Eppendorf centrifuge. The platelet-rich plasma was prepared from a low-speed spin of EDTA-treated mouse plasma. The isolated platelets were resuspended in DMEM cell culture media plus 0.2% bovine serum albumin. Cyclodexrin/cholesterol complexes containing [$^3$H]cholesterol was added to the final concentration of ~3 mM CD, and ~1 µCi [$^3$H]cholesterol/ml and the mixture was incubated at 37° C. for 30 minutes. The labeled platelets were then washed three times with the same medium by brief spin and resuspension. HDL was then added to initiate the cholesterol efflux and allowed to proceed for the time period as indicated. Cholesterol efflux was determined as percentage efflux (count of supernatant/total count×100%).

To determine cholesterol efflux from MkPs to HDL, we labeled total BM cells by incubation with 0.03 mM methyl-α-cyclodextrin/BODIPY-cholesterol (molar ratio CD:cholesterol: BODIPY-cholesterol 40:0.8:0.2; Avanti Polar Lipids—Alabama, USA) in IMDM media plus 0.2% BSA at 37° C., 5% $CO_2$ for 30 minutes. The cells were washed three times with fresh IMDM media by brief spin and resuspension. CD or rHDL was then added to the cell suspension at the indicated concentration to initiate the efflux for the indicated period of time. The efflux was stopped by a brief spin and removal of the acceptors. The samples treated without CD or rHDL were used as the baseline for efflux. To assess BODIPY-cholesterol content in MkPs, the cell suspension was stained with a cocktail of lineage markers (Sca1, CD127, CD45R, CD19, CD11b, CD3e, TER-119, CD2, CD8, CD4, and Ly-6C/G; all APC; eBioscience) and progenitor cell markers, ckit, CD16/CD32 (FcγRII/III), CD34, CD41. MkPs were identified as lineage$^-$, ckit$^+$, CD16/CD32$^{lo}$, CD34$^{lo}$ and CD41$^+$ and the mean fluorescence intensity (MFI) of BODIPY-cholesterol from MkPs was measured by flow cytometry (LSRII, BD Biosciences) to assess BODIPY-cholesterol content in MkPs or cholesterol efflux (1-remaining MFI/baseline MFI×100%).

Flow Cytometry Based Proliferation Studies

Blood leukocytes and BM HSPCs were stained and analyzed or sorted as described (Murphy, A. J. et al. 2011). Briefly, BM cells from the mouse femurs and tibias were stained with a cocktail of antibodies to lineage committed cells (CD45R, CD19, CD11b, CD3e, TER-119, CD2, CD8, CD4, Ly-6C/G: All FITC, eBioscience), antibodies to Sca1 (Pacific Blue) and ckit (APC Cy7) to identify HSPC populations and LSK (lin−, Sac1+ and ckit+) cells, and antibodies to CD16/CD32 (FcγRII/III), CD34 to separate CMP (lin−, Sca1−, ckit+, CD34int, FcγRII/IIIint), GMP (lin−, Sca1−, ckit+, CD34int, FcγRII/IIIhi), MEP (lin−, Sca1−, ckit+, CD34lo, FcγRII/IIIlo). For DNA content analysis (G2M phase), BM cells were fixed, and stained with DAPI (Invitrogen) prior to flow cytometry analysis. To determine in vivo cell proliferation, EdU (Invitrogen) was injected into mice via the tail vein 24 hours prior to being sacrificed. Cells were immunostained as described above in preparation for flow cytometry. Cells were then fixed and permeabilized using 0.01% saponin (w/v; Fluka) and 1% FCS (v/v) in IC fixation buffer (eBiosciences) for 30 minutes. Cells were then washed and stained with Alexa Fluor-conjugated azides using the Click-iT system (Invitrogen). Proliferation was quantified as percentage of EdU$^+$ cells by flow cytometry.

Quantitative Real Time RT-PCR (q-PCR)

RNA extraction, cDNA synthesis, and q-PCR of HSPCs were performed as described[5]. The quality of RNA samples was determined using Agilent 2100 Bioanalyzer and RNA 6000 LabChip. The primer sequences used for q-PCR are shown in Table 1.

TABLE 1

Primer sequences used for q-PCR analysis

| Gene | Forward primer | Reverse primer |
|---|---|---|
| Abca1 | CAGCTTCCATCCTCC TTGTC | CCACATCCACAACTG TCTGG |
| Abcg1 | GTACCATGACATCG CTGGTG | AGCCGTAGATGGACA GGATG |
| Abcg4 | CGTGCTCACCTTTCC CTTAG | CGATGCTGCAGTACA CCACT |
| Hmgcs1 | GCCGTGAACTGGGTC GAA | GCATATATAGCAATG TCTCCTGCAA |
| Ldlr | GAGGAACTGGCGGCT GAA | GTGCTGGATGGGGAG GTCT |

TABLE 1-continued

Primer sequences used for q-PCR analysis

| Gene | Forward primer | Reverse primer |
|---|---|---|
| Scarb1 | TCCCCATGAACTGTT CTGTGAA | GTTTGCCCGATGCCC TTGA |
| β-actin | AGCCATGTACGTAGC CATCC | GTGGTGGTGAAGCTG TAGCC |
| 36B4 | CCTGAAGTGCTCGAC ATCAC | CCACAGACAATGCCA GGAC |

Megakaryocyte Colony Forming Unit Assay

Primary BM HSPC cells obtained by FACS were plated in methylcellulose-based media (5000 cells/assay) containing TPO (50 ng/mL), IL-6 (20 ng/mL), and IL-3 (10 ng/mL) and incubated for 8 days according to manufacturer's protocol (Megacult-C, Stemcell Technologies). Cultures were fixed and the MK colonies visualized by staining for acethylcholinesterase activity. Nuclei were counterstained with Harris' hematoxylin. Colonies containing more than 3 megakaryocytes were scored as CFU-Mk.

Anti-ABCG4 Antibody

The rabbit anti-ABCG4 antibody was custom made by Pacific Immunology (CA, USA) against a synthetic ABCG4 peptide (KKVENHITEAQRFSHLPKR). The mono-specific anti-peptide antibodies were purified using a peptide-affinity column. The specificity of the antibody for ABCG4 protein was assessed by immunofluorescence microscopy which showed specific immunofluorescence signals in HEK293 cells expressing ABCG4 but not HEK293 cells transfected with mock vectors (not shown).

Rabbit polyclonal anti-c-MPL antibody was kindly provided by Dr. Wei Tong of University of Pennsylvania and the specificity of the antibody against cell surface c-MPL in flow cytometry has been reported previously (Tong, W. et al. 2007; Bersenev, A. et al. 2008).

Neutrophil and Monocyte-platelet Aggregates

Blood was collected via the tail vein into EDTA lined tubes on ice to prevent coagulation and leukocyte activation. RBCs were lysed and the washed cells were then stained with CD45, CD115, Gr1 (Ly6-C/G), CD11b and CD41 for 30 mins on ice. The cells were carefully washed, resuspended in FACS buffer and run on the LSRII to detect leukocyte platelet interactions and leukocyte activation. Viable cells were selected based on forward and side scatter characteristics and then $CD45^+$ leukocytes were selected. $Ly6-C^{hi}$ monocyte platelet aggregates were identified as $CD115^+Gr1^{hi}$ ($Ly6-C^{hi}$) $CD41^+$. Neutrophils platelet aggregates were identified as $CD115^-Gr1^+$ ($Ly6-G^+$) $CD41^+$. Platelet dependent activation of $Ly6-C^{hi}$ monocytes and neutrophils was measured as CD11b MFI after subtracting the expression of CD11b on $Ly6-C^{hi}$ or neutrophils, which were not interacting with platelets.

Platelet Derived Microparticles

Blood was collected via the tail vein into EDTA lined tubes on ice and plasma was obtained via centrifugation. Equal amounts of plasma (20 µL) from each sample was diluted with HEPES binding buffer (80 µL) and then incubated with annexin V and anti-CD41. Equal amounts of 1 µm beads (Invitrogen) were added to the sample, which was then run on an LSR-II. Platelet derived microparticles were detected as particles less than 1 µm in size that stained positive for CD41 and annexin V. A stopping gate was placed over the beads, to ensure accurate counting in each sample. Data was converted to number of microparticles per 1 µL of whole blood.

Platelet Preparation

Whole blood was collected from the inferior vena cava in ACD (10%, vol/vol) from WT or $Abcg4^{-/-}$ mice under anesthesia. Platelet-rich plasma (PRP) from each individual mouse was obtained from whole blood by centrifugation at 300 g for 7 minutes at room temperature. Washed platelets were prepared from PRP by centrifuged at 1,000 g in the presence of prostacyclin (0.1 µg/ml) for 10 min. After two washing steps, platelets were resuspended in modified Tyrodes-HEPES buffer (137 mM NaCl, 0.3 mM $Na_2HPO_4$, 2 mM KCl, 12 mM $NaHCO_3$, 5 mM HEPES, 5 mM glucose, 1 mM CaCl2, pH 7.3) containing 0.35% bovine serum albumin.

$FeCl_3$ Induced Carotid Artery Thrombosis

Mice were anesthetized and a cervical incision was made to expose the common carotid artery. A miniature Doppler flow probe (TS420 transit-time perivascular flowmeter, Transonic Systems Inc.) was placed on the carotid artery to monitor blood flow. The injury to the artery was induced by a piece of Whatman paper (2×2 mm) saturated with 5% $FeCl_3$. The time to the cessation of the blood flow was recorded as occlusion time.

Ex vivo Flow Chamber Assay

Heparin (5 U/ml) anticoagulated whole blood was incubated with 1 µM of fluorescent dye DiOC6 (Sigma, St. Louis. Mo, USA) for 10 minutes at 37° C. Then, the fluorescently labeled whole blood was perfused over the collagen coated glass cover surface (microcapillary glass tube coated with 100 µm/mL Horm collagen (Nycomed) overnight) at a controlled shear rate (1800 $s^{-1}$) using a syringe pump for 3 minutes. Adherent platelets and aggregates in the chamber were washed and examined under inverted fluorescent microscope and pictures of adhered platelets were recorded for analysis. Surface coverage was calculated using ImageJ.

c-MPL Expression

Detection of c-MPL from in vivo and in vitro experiments was performed as follows. After harvesting BM progenitor cells, RBCs were lysed and the cells were then resuspended in FACS buffer. Cells were then stained with a cocktail of lineage markers to allow negative selection of BM progenitor cells (Sca1, CD127, CD45R, CD19, CD11b, CD3e, TER-119, CD2, CD8, CD4, and Ly-6C/G; all FITC; eBioscience) and progenitor cell markers, ckit, CD16/CD32 (FcγRII/III), CD34, CD41 and c-MPL or isotype control and allowed to stain on ice for 30 mins. Cells were then washed and stained with a fluorescently conjugated secondary anti-rabbit antibody to detect the anti-c-MPL for a further 30 mins on ice. After this the cells were washed, resuspended in FACS buffer and run on the LSRII. MEPs were identified as $lin^- ckit^+CD16/CD32^{lo}CD34^{lo}CD41^-$, while MkPs were identified as $lin^-ckit^+CD16/CD32^{lo}CD34^{lo}CD41^+$.

Expression of c-MPL on late stage megakaryocyte was achieved by staining BM cells with a cocktail of lineage markers (Sca1, CD127, CD45R, CD19, CD3e, TER-119, CD2, CD8 and Ly-6C/G -all FITC), CD41 and c-Mpl or isotype control as above. After staining with the antibodies the BM cells were then fixed and permeabilized using BD cytofix/perm buffer for 20 mins on ice, followed by washing with BD cytofix/perm wash buffer. Cells were the resuspended in FACS buffer containing propidium iodide to detect megakaryocyte ploidy. Expression of c-MPL was measured on total and late stage megakaryocytes (defined at 32N and 64N).

Expression of c-MPL on platelets was carried out by obtaining PRP and staining with CD41 and c-MPL as outlined above. The expression of c-MPL was quantified in these respective populations by MFI, normalized to the isotype control.

c-Cbl Phosphorylation

BM progenitor cells were stimulated with TPO at the indicated concentration for the specified period of time at 37° C. and then immediately diluted with ice-cold buffer and placed on ice to prevent further changes in phosphorylation. Cells were then centrifuged and the pellet resuspended in BD fix buffer (BD Biosciences) for 10 mins on ice. The cells were washed with BD flow cytometry staining buffer, centrifuged and then resuspended in BD cytofix/perm buffer III for 20 mins. After this the cells were washed and resuspended in BD staining buffer and incubated with lineage (Sca1, CD127, CD45R, CD19, CD11b, CD3e, TER-119, CD2, CD8, CD4, and Ly-6G; all FITC; eBioscience) and progenitor cell markers, ckit, CD16/CD32 (FcγRII/III), CD34, CD41 and anti-phospho-c-Cbl (Y700human/Y698mouse; BD biosciences) or an isotype control for 30 mins on ice. The cells were then washed, resuspended in FACS buffer and run on an LSRII. Phosphorylated c-Cbl was normalized against isotype control staining.

Immunofluorescence Confocal Microscopy

MkPs collected by FACS from WT or $Abcg4^{-/-}$ BM cells were forced to attach to glass slides by a brief spin in Cytospin. The cells were then fixed with 2% paraformaldehyde, permeabilized with 1% Triton X-100 in PBS for 1 minute and incubated with 4% BSA in PBS plus 0.1% saponin to block the non-specific binding sites. The diluted primary antibodies against ABCG4 or cellular organelle markers (58K Golgi protein antibody, Novus Biologicals; TGN38 antibody, BD Biosciences; c-MPL antibody, Sigma-Aldrich; Lamp2 antibody, Novus Biologicals) were then added to incubate with the cells. After washing, the fluorescent secondary antibodies were added. Where indicated, the washed cells were counterstained with or without DAPI and examined with fluorescence confocal microscope.

Statistics

For aortic morphometric atherosclerotic lesion quantification and analysis, two-way ANOVA was used. For comparison of one group with another, for instance the c-Cbl phosphorylation time course as shown in FIG. 4A, t test was used. For comparison of various treatments on different genotypes, one-way ANOVA was used.

Example 1

Figure 1B:
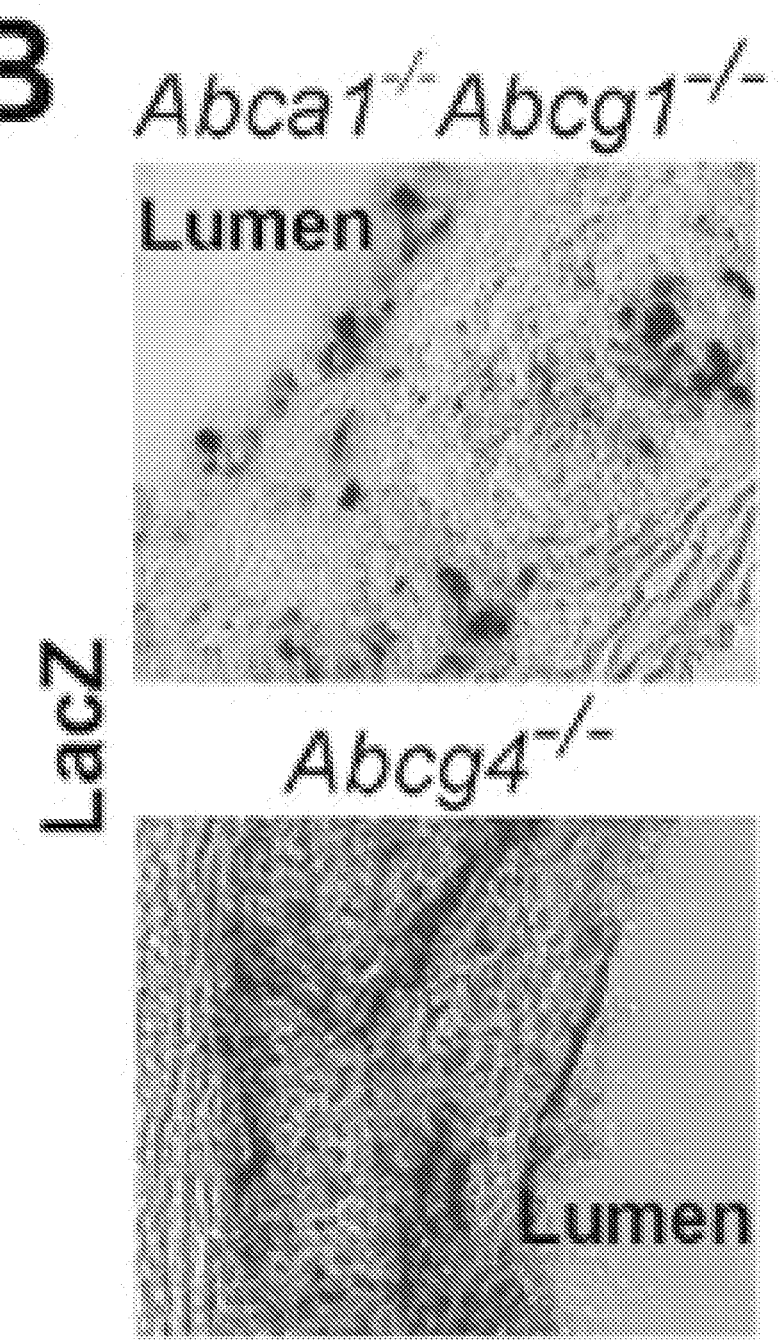
Figure 1C:
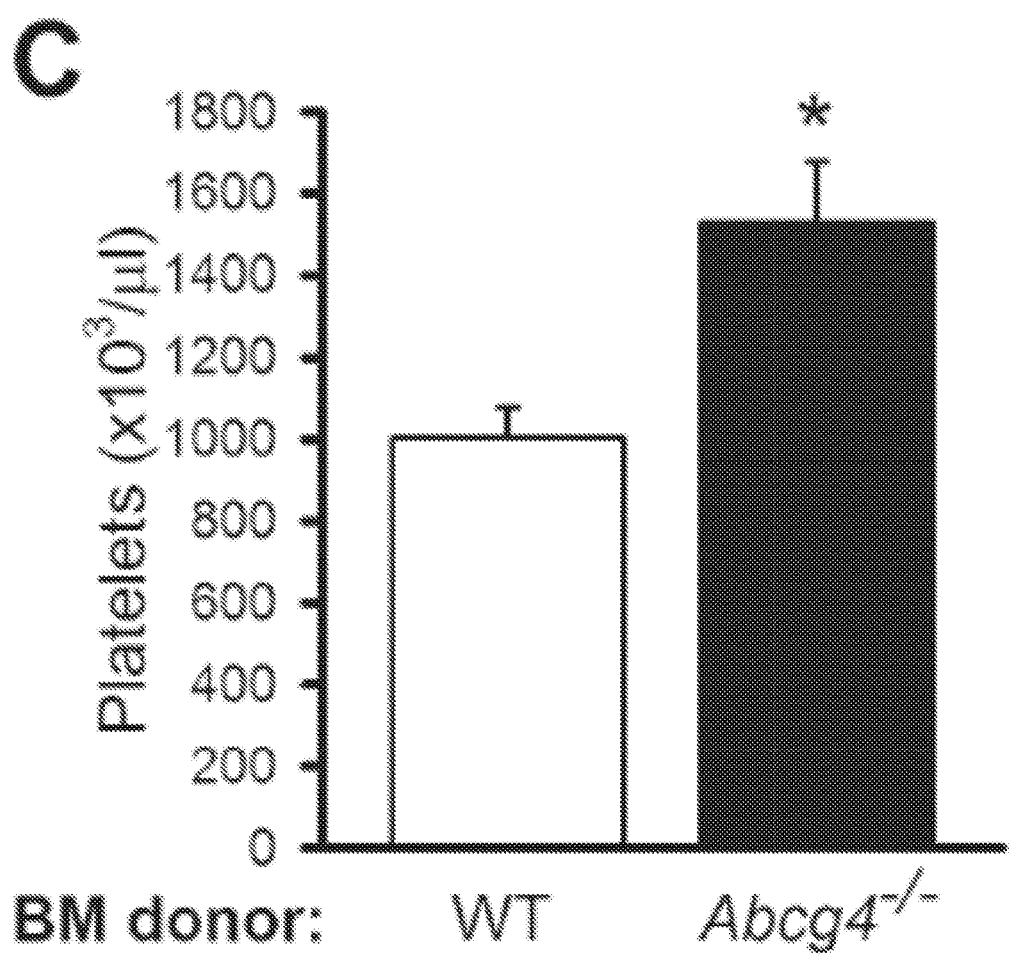

Bone Marrow (BM) ABCG4 Deficiency Increases Platelet Count and Accelerates Atherosclerosis and Thrombosis The atherogenic process involves the arterial deposition of cholesterol-rich lipoproteins, which are taken up by macrophages leading to foam cell formation and chronic inflammation (Libby, P. et al. 2011; Ross, R. 1993). This process may be reversed by HDL, in part reflecting its ability to maintain cholesterol efflux from macrophages via the ATP binding cassette transporters (ABC), ABCA1 and ABCG1 (Tall, A. R. et al. 2008). In addition, both transporters are expressed in hematopoietic stem and multi-potent progenitor cells (HSPCs), and the absence of ABCA1 and ABCG1 leads to hyper-proliferation of HSPCs, monocytosis, neutrophilia and accelerated atherosclerosis in mice (Yvan-Charvet, L. et al. 2010). The transporter ABCG4, which is highly homologous to ABCG1 promotes cholesterol efflux to HDL when overexpressed in cultured cells (Wang, N. et al. 2004). However, ABCG4 is not expressed in macrophage foam cells (Wang, N. et al. 2006) and its in vivo functions have remained enigmatic. Abcg4 expression has been detected in the brain and in hematopoietic tissues such as fetal liver and BM (Annilo, T. et al. 2001; Bojanic, D. D. et al. 2010). In order to uncover a potential function of hematopoietic ABCG4, hematopoietic functions and atherogenesis were assessed in a hypercholesterolemic mouse model of atherosclerosis, in which irradiated $Ldlr^{-/-}$ mice were reconstituted with BM from WT or $Abcg4^{-/-}$ mice. After feeding a high fat high cholesterol diet (WTD) for 12 weeks, atherosclerotic lesions were significantly increased in the aorta of $Ldlr^{-/-}$ recipient mice reconstituted with the ABCG4-deficient BM cells (FIG. 1A). In contrast, the single deficiency of ABCG1 in the BM did not increase advanced atherosclerosis, consistent with previous studies (Ranalletta, M. et al. 2006; Meurs, I. et al. 2012). Histological analysis of lesions showed typical, macrophage foam cell-rich atherosclerotic lesions, with no differences in morphology between lesions from the WT or $Abcg4^{-/-}$ BM recipients (FIG. 5A). The Abcg4 knockout mice were created using a lacZ knock-in[14]. However, no lacZ-positive cells were detected in lesions of $Abcg4^{-/-}$ BM recipient mice (FIG. 1B). As a positive control, lacZ-positive cells indicating Abcg1 expression in lesions were readily detected in the $Ldlr^{-/-}$ recipients reconstituted with $Abca1^{-/-}Abcg1^{-/-}$ BM. Levels of plasma HDL cholesterol, non-HDL cholesterol and triglyceride were similar in WT or $Abcg4^{-/-}$ BM recipients (FIG. 5B-D). The leukocyte, monocyte (FIGS. 5E-F), total lymphocyte, B- and T-cell counts were also similar. Unexpectedly, the platelet count was 52% greater in $Abcg4^{-/-}$ BM recipient compared with WT recipients (FIG. 1C). Mild anemia and reticulocytosis were observed in the $Abcg4^{-/-}$ BM→$Ldlr^{-/-}$ recipient mice (FIG. 5G-H). In chow-fed $Abcg4^{-/-}$ mice, the platelet count was greater than in WT mice (11% increase, p=0.018, n=40/group), whereas all other blood cell parameters were similar.

Activated platelets contribute directly to atherogenesis (Huo, Y. et al. 2003), in part by promoting activation and adhesion of monocytes to arterial endothelium (Huo, Y. et al. 2003; Koenen, R. R. et al. 2009). Platelet-neutrophil and platelet-Ly6-$C^{hi}$ monocyte aggregates, were increased in hypercholesterolemic $Abcg4^{-/-}$ mice compared to WT (FIG. 5I), and expression of CD11b, a marker of neutrophil and monocyte activation that mediates their adhesion to endothelium (Mazzone, A. et al. 1993), was greater in these aggregates (FIG. 1D). Depletion of platelets by injection of CD41 antibodies, which markedly reduced platelet count in the WT and $Abcg4^{-/-}$ BM→$Ldlr^{-/-}$ mice, reduced aggregate numbers and leukocyte CD11b expression (FIG. 1D and FIG. 5I). Platelet activation increases platelet microparticle generation (Flaumenhaft, R. 2010) and microparticles may promote atherogenesis by facilitating chemokine deposition onto arterial endothelium and recruitment of monocytes to lesions (Mause, S. F. et al. 2005). The levels of platelet-derived microparticles were 3-fold higher in hypercholesterolemic $Abcg4^{-/-}$ BMT mice than in WT BMT mice (FIG. 1E). Circulating reticulated platelets levels correlate directly with platelet reactivity (Guthikonda, S. et al. 2008) and are strongly associated with increased risk of myocardial infarction in humans (Lakkis, N. et al. 2004). There was also a significant increase in the percentage of reticulated platelets (FIG. 1F), consistent with increased platelet production and turnover (Stohlawetz, P. et al. 1998). These findings are consistent with previous studies in which infusions of activated platelets or platelet depletion with antibody respectively increased or decreased atherosclerotic lesion formation (Huo, Y. et al. 2003; Massberg, S. et al. 2002), and importantly also suggest that increased endogenous platelet production can promote atherogenesis.

Figure 1H:
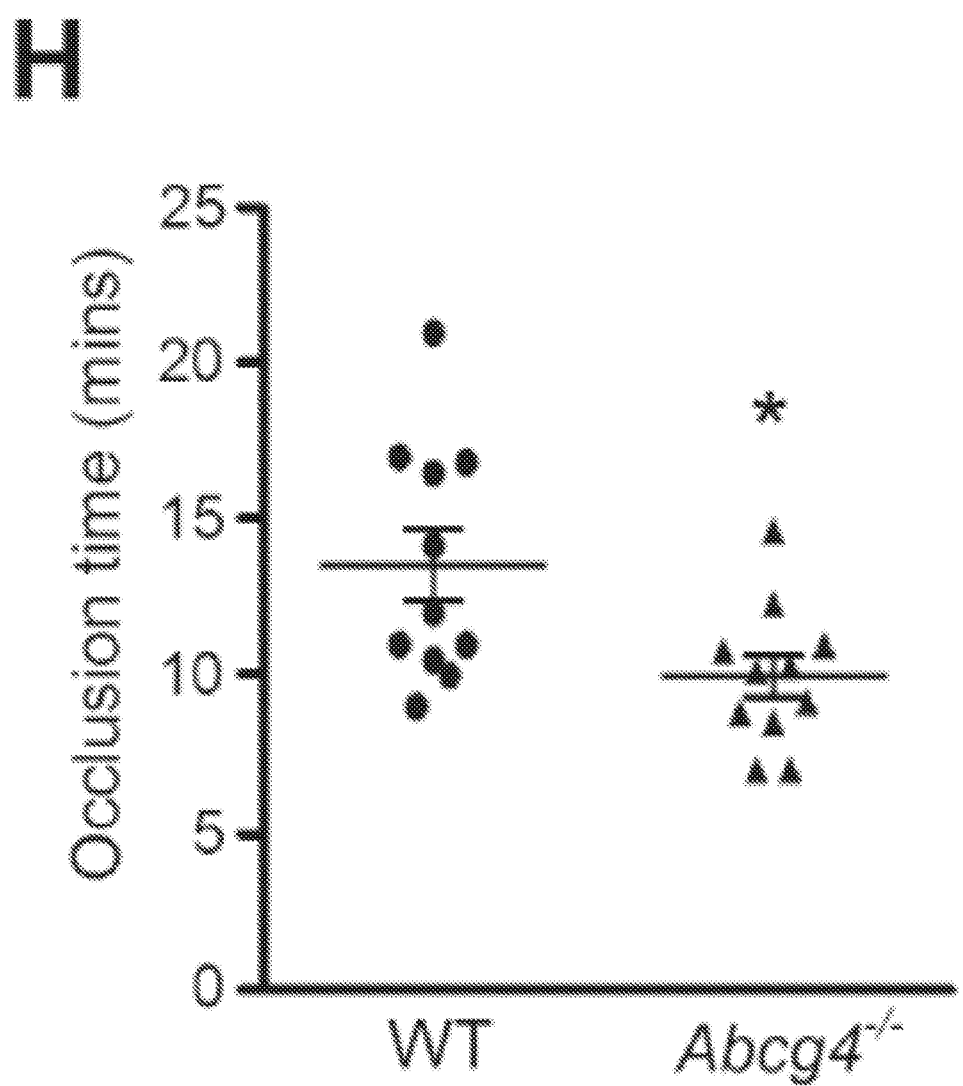

Thrombocytosis and increased levels of reticulated platelets would also be expected to promote thrombosis. Mice are resistant to spontaneous thrombosis on atherosclerotic plaques. Thus, to assess increased thrombogenicity, thrombus formation in whole blood was evaluated using an ex vivo perfusion chamber model and showed a marked increase in Abcg4$^{-/-}$ platelet adhesion and aggregation to a collagen-coated surface under shear-flow conditions (FIG. 1G). Arterial thrombosis was also examined in vivo using a carotid artery thrombosis model. Carotid artery occlusion by thrombus following FeCl$_3$ injury was significantly accelerated in Abcg4$^{-/-}$ BMT mice (FIG. 1H). Together, these findings indicate an increased propensity to thrombus formation in hypercholesterolemic mice with BM ABCG4 deficiency.

Example 2

Defective Cholesterol Efflux from ABCG4-deficient Megakaryocyte Progenitor Cells (MkPs) is Associated with Increased MkP Thromopoietin Receptor (c-MPL) and Megakaryopoiesis To understand the mechanisms responsible for thrombocytosis, it was considered that ABCG4 might be acting directly in platelets to promote cholesterol efflux. Abcg4 mRNA was not detected in WT platelets, or LacZ staining in platelets of Abcg4$^{-/-}$ mice, and moreover, there was no alteration in platelet cholesterol efflux to HDL, or platelet cholesterol levels in Abcg4$^{-/-}$ mice. This indicated that ABCG4 is not acting directly in platelets to promote cholesterol efflux. However, human platelets do express ABCG4 mRNA.

Figure 6C:
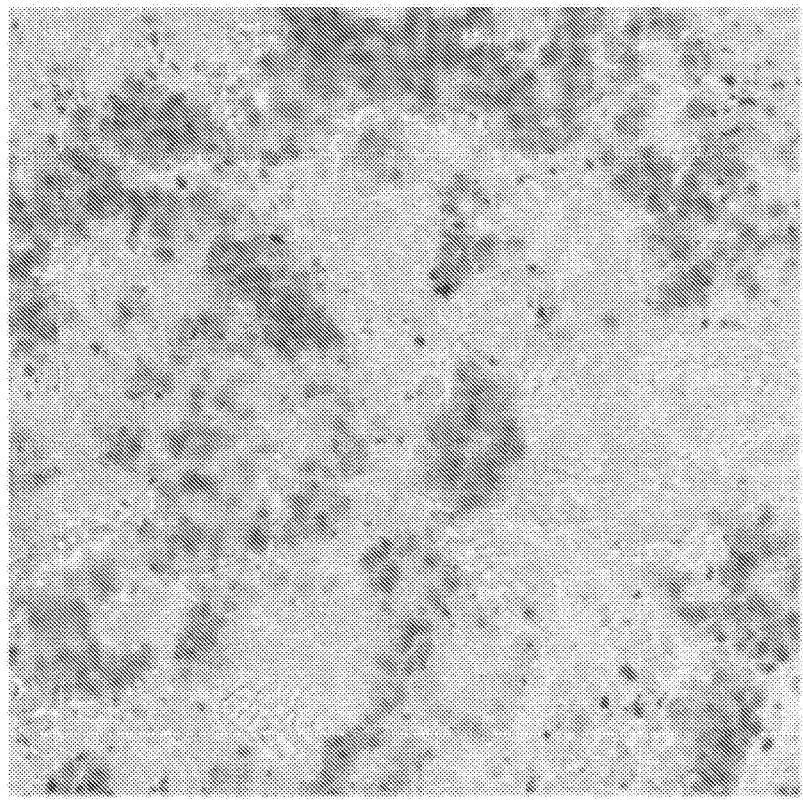
FIG. 6. (A) Representative of LacZ staining of BM sections of WT or Abcg4$^{-/-}$ mice fed chow diet. Megakaryocytes are indicated by black arrows while LacZ-positive cells are indicated by white arrows Original magnification 20×. (B) Lac-Z staining of spleen of WT and Abcg4$^{-/-}$ mice fed the chow diet and (C) from Abcg4$^{-/-}$ BM Ldlr$^{-/-}$ recipient mice fed WTD for 12 weeks. (D) Representative LacZ staining of spleen sections and quantification of LacZ-positive splenic cells of Abcg4$^{-/-}$ mice fed the chow diet 3 days after either vehicle or phenylhydrazine injections. Error bars are S.D (n=5). * P<0.05.
Figure 6D:
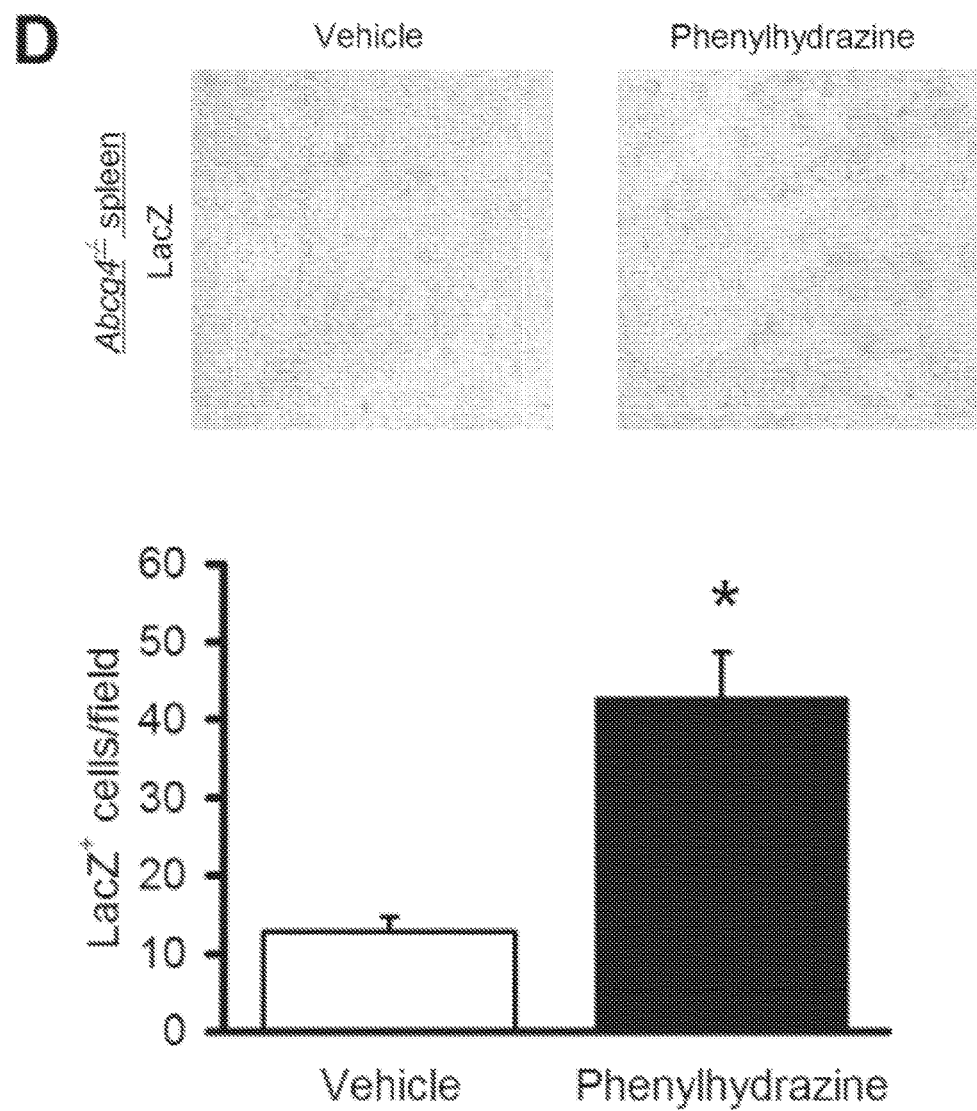

The phenotype of ABCG4 deficiency, with prominent thrombocytosis, increased reticulated platelets, mild anemia, increased platelet/leukocyte aggregates and increased platelet microparticles, resembles that of essential thrombocytosis (Villmow, T. et al. 2002), a myeloproliferative neoplasm associated with prominent athero-thrombosis (Tefferi, A. et al. 2011). In many patients with this disorder, mutations in the thrombopoietin receptor c-MPL or downstream signaling molecules (JAK-2) in BM progenitors, lead to increased platelet production (Tefferi, A. et al. 2011; Pikman, Y. et al. 2006). Platelets are produced by megakaryocytes in the BM and spleen, and megakaryocytes are derived from megakaryocyte/erythrocyte progenitors (MEP) (Nakorn, T. N. 2003). LacZ-positive cells were found in BM (FIG. 6A, white arrows) and in the red pulp of the spleen in Abcg4$^{-/-}$ mice (FIG. 6B), especially following BMT in hypercholesterolemic Ldlr$^{-/-}$ mice (FIG. 6C). Using a standard method for induction of hemolysis and expansion of MEPs (phenylhydrazine) (Sanchez, M. et al. 2006), a marked expansion of LacZ positive cells was observed in the spleen following treatment with phenylhydrazine (FIG. 6D).

LacZ positive cells were distinct from large multinucleate megakaryocytes (FIG. 6A, black arrows). Moreover, Abcg4 mRNA was not detected in WT platelets, or LacZ staining in platelets of Abcg4$^{-/-}$ mice (not shown). There was no alteration in platelet cholesterol efflux to HDL, or platelet cholesterol levels in Abcg4$^{-/-}$ mice (FIG. 7A-B), indicating that ABCG4 is not acting in platelets to regulate circulating platelet levels and a mechanism completely different to those previously reported (Nofer, J. R. et al. 2011).

Figure 2C:
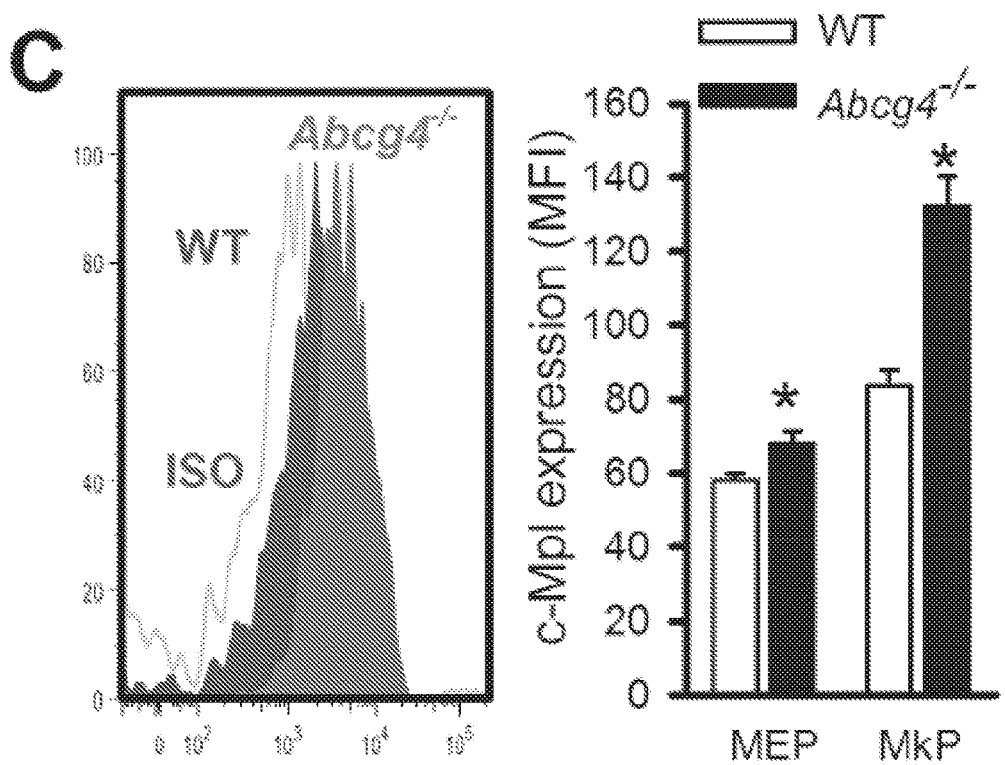
FIG. 2. (A) Abcg4 mRNA expression in various types of BM and peripheral white blood cells in WT mice determined by q-PCR. (n=5). (B) Quantification of BM cell populations and (C) cell surface c-MPL levels of Ldlr$^{-/-}$ recipient mice fed WTD for 12 weeks (n=5). (D) MK-CFU assay using HPCs harvested by FACS from WT or Abcg4$^{-/-}$ mice. (E) Platelet count in the WT and Abcg4$^{-/-}$ mice (n=5) receiving a single dose of TPO (50 μg/kg BW) or the vehicle control. The representative of two studies with similar results is shown. (F) Bodipy-cholesterol efflux from WT or Abcg4$^{-/-}$ MkPs to CD (2 mM) or rHDL (20 μg/ml) for 2 hours (n=4). (G) Bodipy-cholesterol levels in WT or Abcg4$^{-/-}$ MkPs following CD/Bodipy-cholesterol loading (n=4). (H) EdU incorporation into and (I) cell surface c-MPL of WT or Abcg4$^{-/-}$ MkPs were determined by flow cytometry (n=4). Error bars are S.E.M. *P<0.05 WT versus Abcg4$^{-/-}$ groups and ^P<0.05 for treatment effect.
Figure 9C:
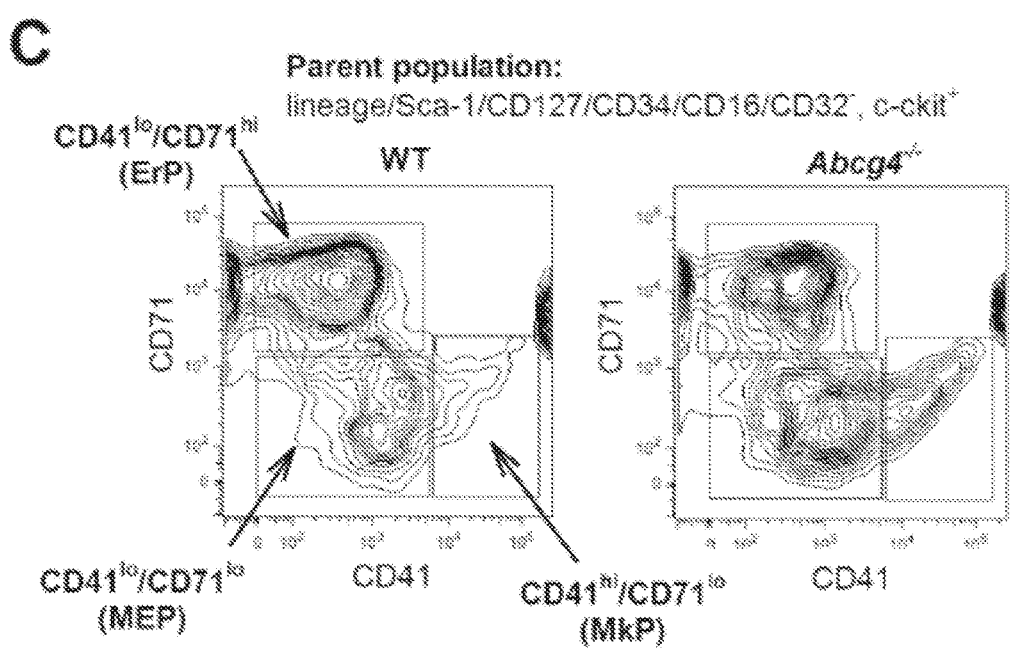
FIG. 9. (A) Abca1 and Abcg1 mRNA expression in WT BM LSK, CMP, GMP and MEP cells. Error bars are S.E.M (n=10). * P<0.05. (B) Abcg4, Abcg1 and Abca1 mRNA expression in MEPs isolated from WT mice treated with or without the LXR agonist T0901317. Error bars are S.D (n=4). * P<0.05. (C) Flow cytometry analysis of CD41$^{lo}$/CD71$^{+}$, CD41$^{+}$/CD71$^{lo}$ and CD41$^{lo}$/CD71$^{lo}$ cells from the defined MEP population of FIG. S4. (D) Abcg4 expression in CD41$^{lo}$/CD71$^{lo}$ MEPs and CD41$^{+}$/CD71$^{lo}$ MkPs as assessed by quantitative RT-PCR.
Figure 9D:
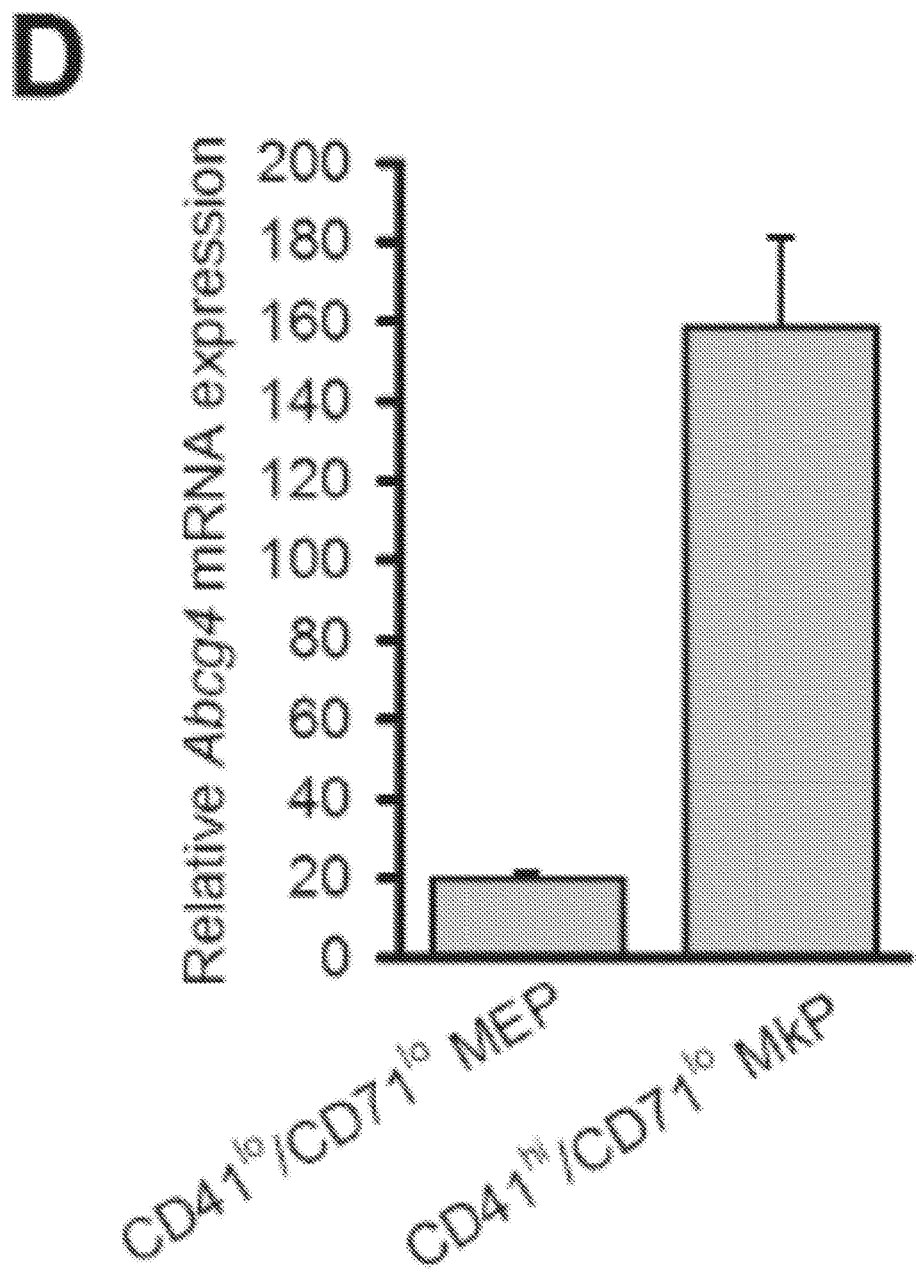
Figure 10B:
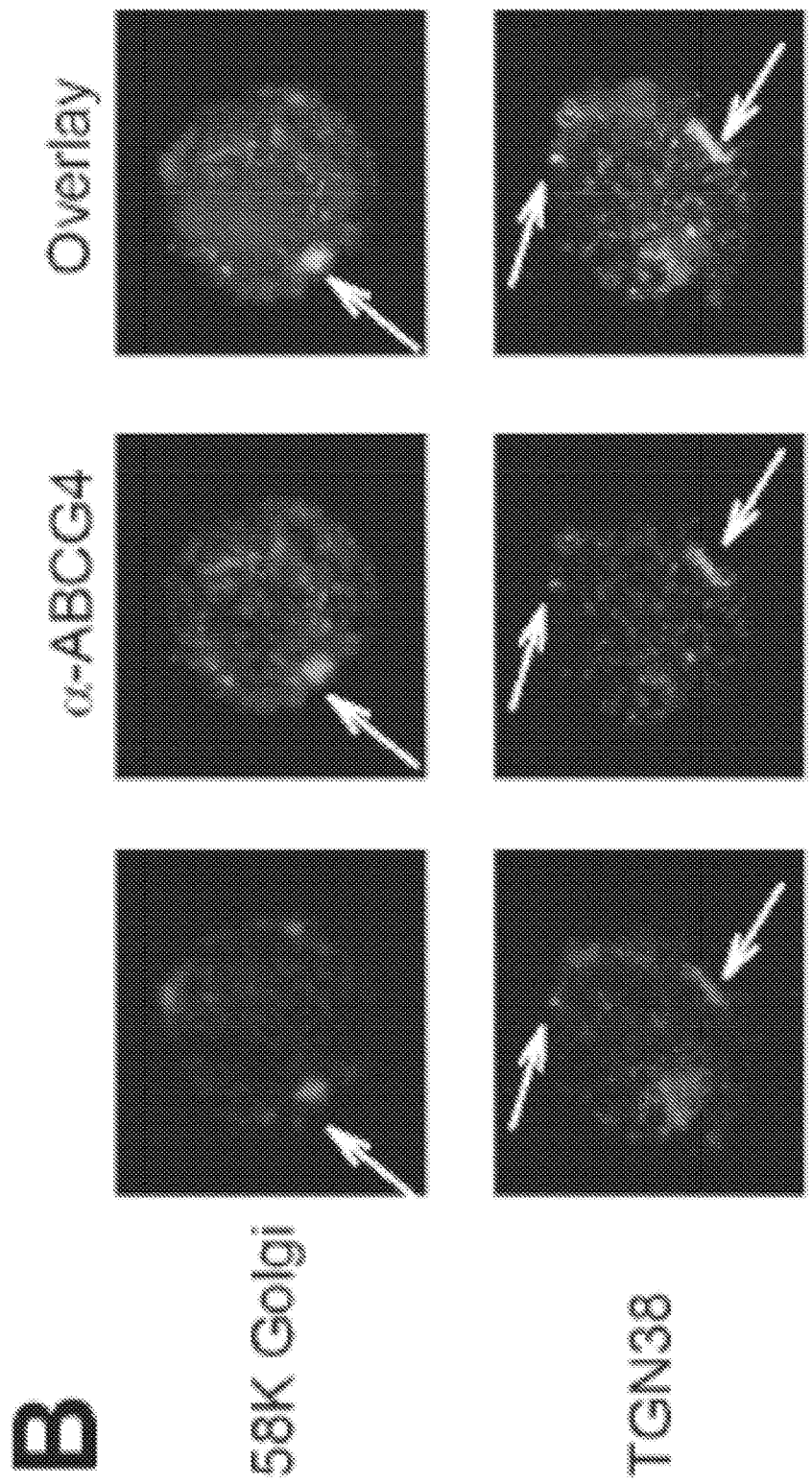
FIG. 10. (A) ABCG4 protein expression in MkPs assessed by immunofluorescence confocal microscopy. The cells were stained with isotype control or anti-ABCG4 antibody and Alexa-488 secondary antibody. (B) Confocal microscopy of WT MkPs immunostained with anti-ABCG4, anti-58K Golgi or anti-TGN38. (C) Immunofluorescence confocal microscopy of WT MkPs stained with anti-ABCG4 and anti-Rab5, anti-Rab 11 or anti-c-MPL antibodies.
Figure 10C:
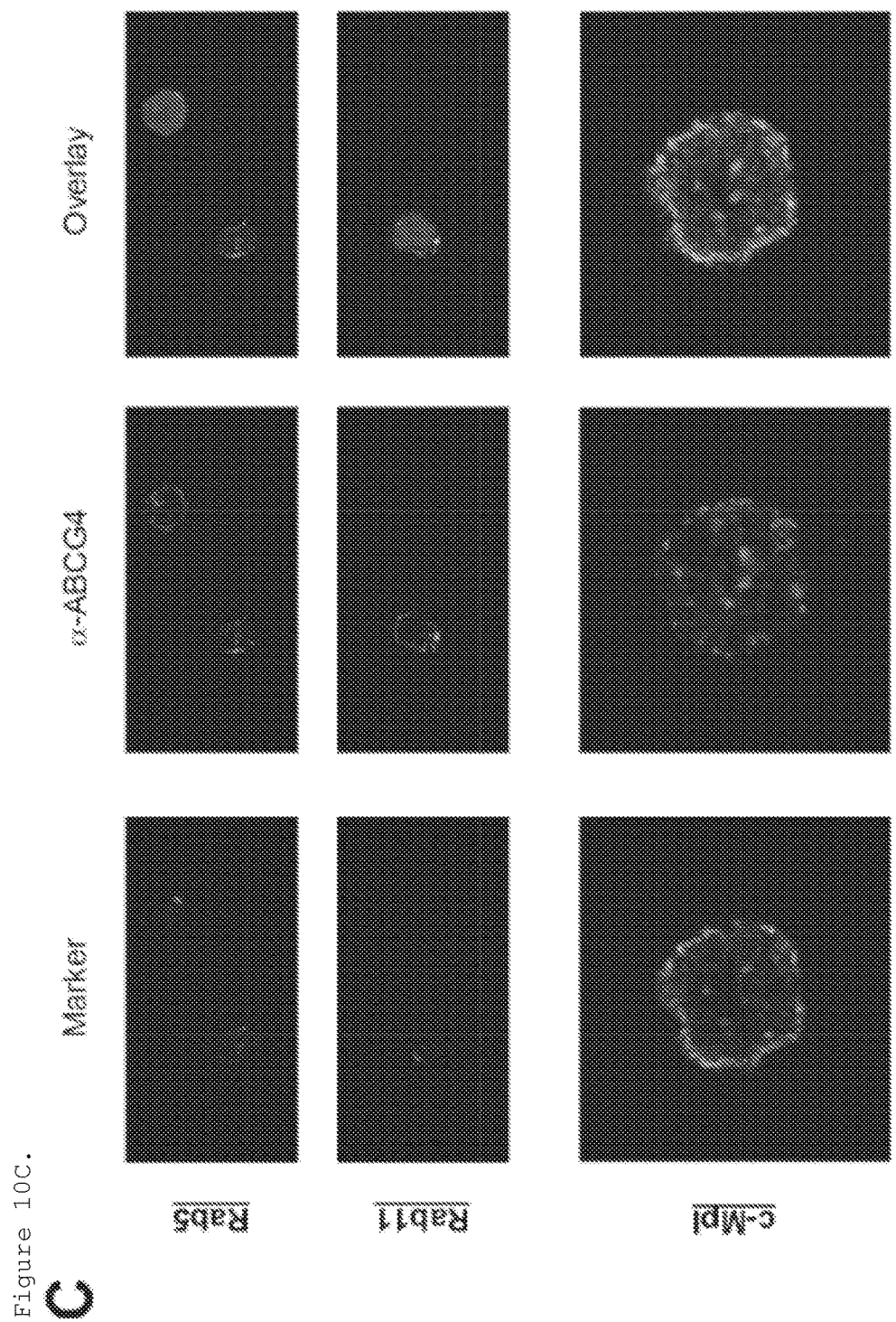

Following separation of hematopoietic cell populations by FACS (FIG. 8), Abcg4 mRNA was primarily detected in MEPs (FIG. 2A), with lower expression in the common myeloid progenitor (CMP) population. Very low or no Abcg4 expression was observed in the other cell types (FIG. 2A). The restricted expression of Abcg4 in MEPs contrasts with Abca1 and Abcg1 which are highly expressed in HSPCs but not in MEPs, even following induction with LXR activator treatment (FIG. 9A-B). Recent studies have shown that the MEP population contains CD41$^+$ cells with megakaryocyte progenitor potential as well as CD71$^+$ cells with erythrocyte progenitor potential (Nakorn, T. N. et al. 2003; Frontelo, P. et al. 2007). The MEP population were sorted into CD41$^+$/CD71$^{lo}$, CD41$^{lo}$/CD71$^+$ or CD41$^{lo}$ CD71$^{lo}$ cell populations (FIG. 9C) and CD41$^+$/CD71$^{lo}$ cells are referred to as megakaryocyte progenitors (MkP). High Abcg4 expression was detected in MkP (FIG. 9D) and CD41$^{lo}$/CD71$^+$ cells (not shown) with lower expression in CD41$^{lo}$/CD71$^{lo}$ MEPs (FIG. 9D). To assess ABCG4 protein expression and localization in MkPs, immunofluorescence confocal microscopy was used. Specific ABCG4 staining was detected in wild type MkPs with anti-ABCG4 antibody but not in Abcg4$^{-/-}$ MkPs or WT MkPs stained with isotype-matched control antibody (FIG. 10A). Interestingly, ABCG4 staining co-localized with Golgi and, particularly trans-Golgi markers (FIG. 10B), while no co-localization with Rab5 (early endosome), Rabbi (endosomal recycling compartment), c-MPL (plasma membrane), Lamp2 (lysosome) or calnexin (endoplasmic reticulum) was detected (FIG. 10C, and not shown). Thus, Abcg4 is selectively expressed in the MEP and MkP populations, and ABCG4 appears to localize primarily to the trans-Golgi.

The percentage in BM of MkPs and CD41$^{lo}$ CD71$^{lo}$ MEPs, but not HSPCs or CMPs, was significantly increased in hypercholesterolemic Abcg4$^{-/-}$ BM recipient compared to WT BM recipients (FIG. 2B). CD41$^{lo}$/CD71$^+$ erythrocyte progenitors in the MEP population were also significantly increased. The mRNA levels of GATA1, PU.1, EKLF and Fli1, transcription factors known to have critical roles in regulation of MEP, MkP and erythrocyte progenitor cell proliferation and differentiation, were similar in Abcg4$^{-/-}$ CD41$^{lo}$/CD71$^{lo}$ MEP, CD41$^+$/CD71$^{lo}$ MkP and CD41$^{lo}$ CD71$^+$ erythrocyte progenitors (not shown), suggesting that there was no marked alteration in lineage choice of Abcg4$^{-/-}$ hematopoietic cells.

Figure 2D:
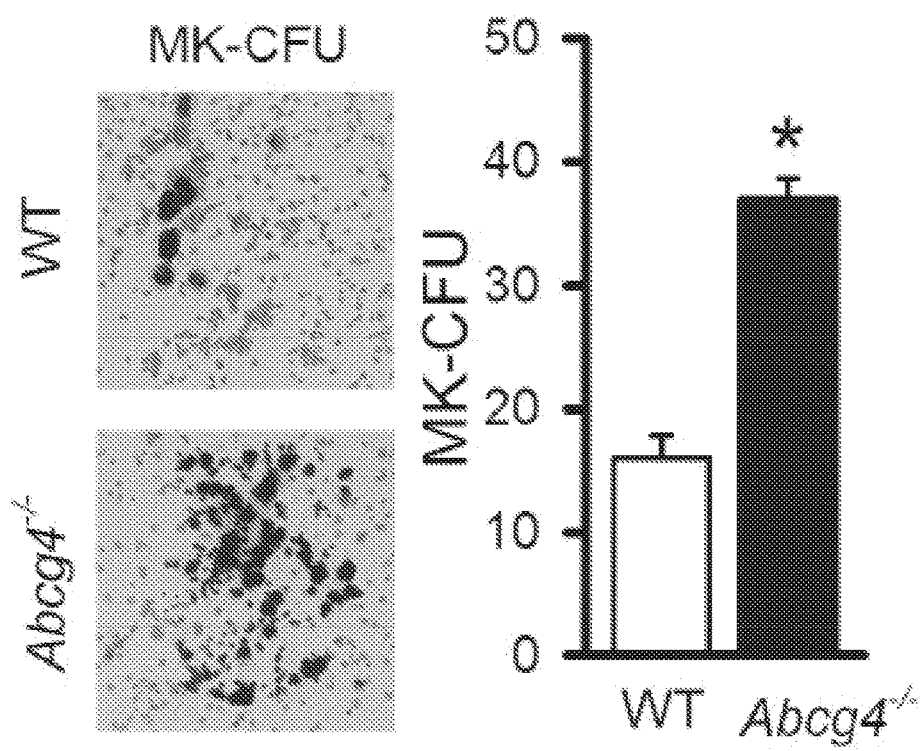
Figure 2E:
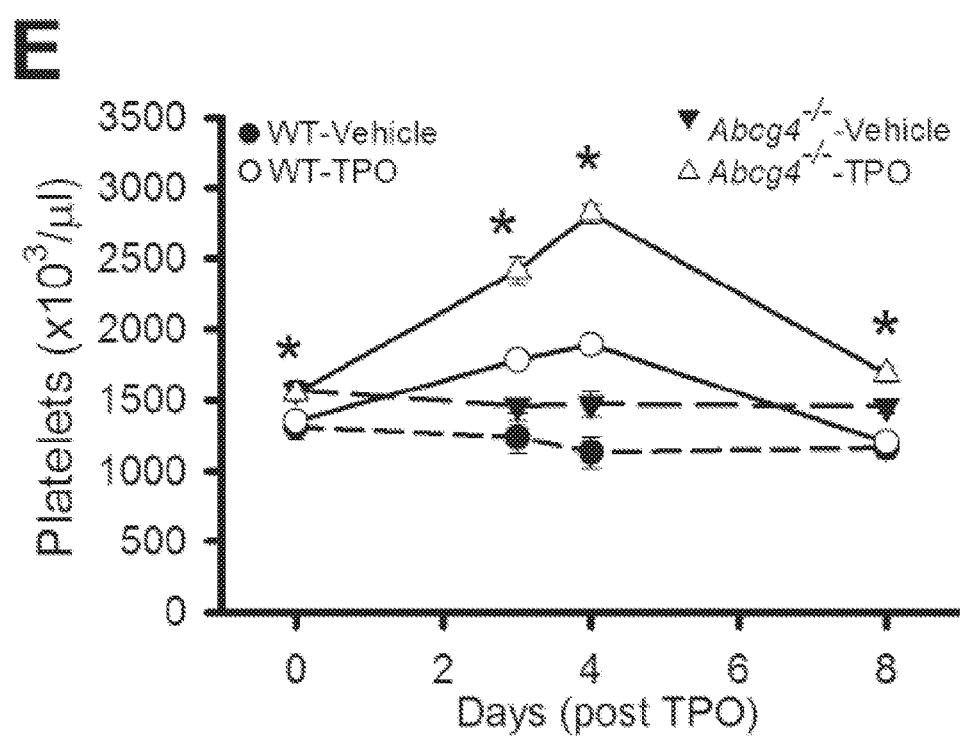
Figure 12A:
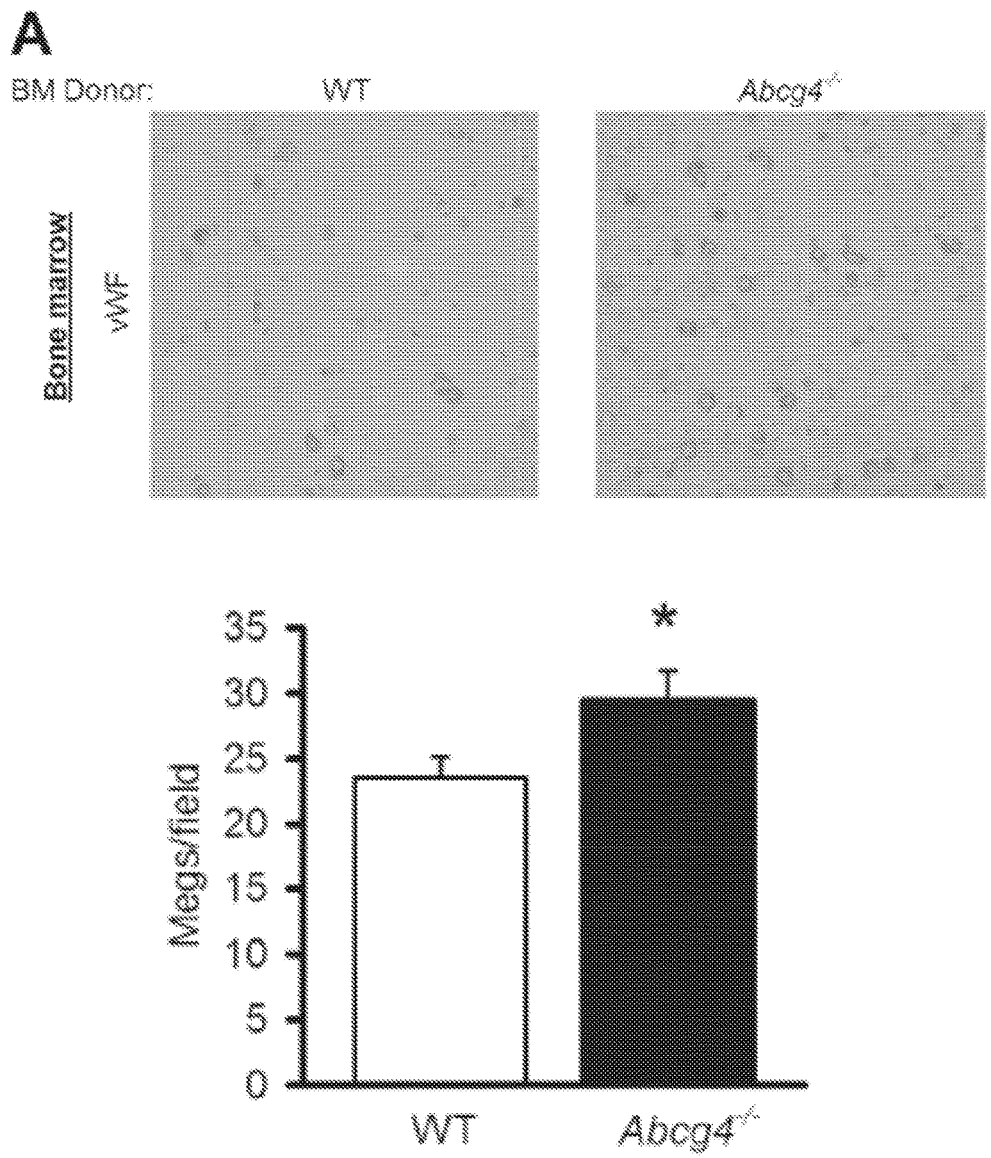
FIG. 12. Representative and quantification of megakaryocyte staining of (A) BM and (B) spleen sections from the WT or Abcg4$^{-/-}$ BM Ldlr$^{-/-}$ recipient mice fed WTD for 12 weeks. Error bars are S.E.M. * P<0.05.
Figure 12B:
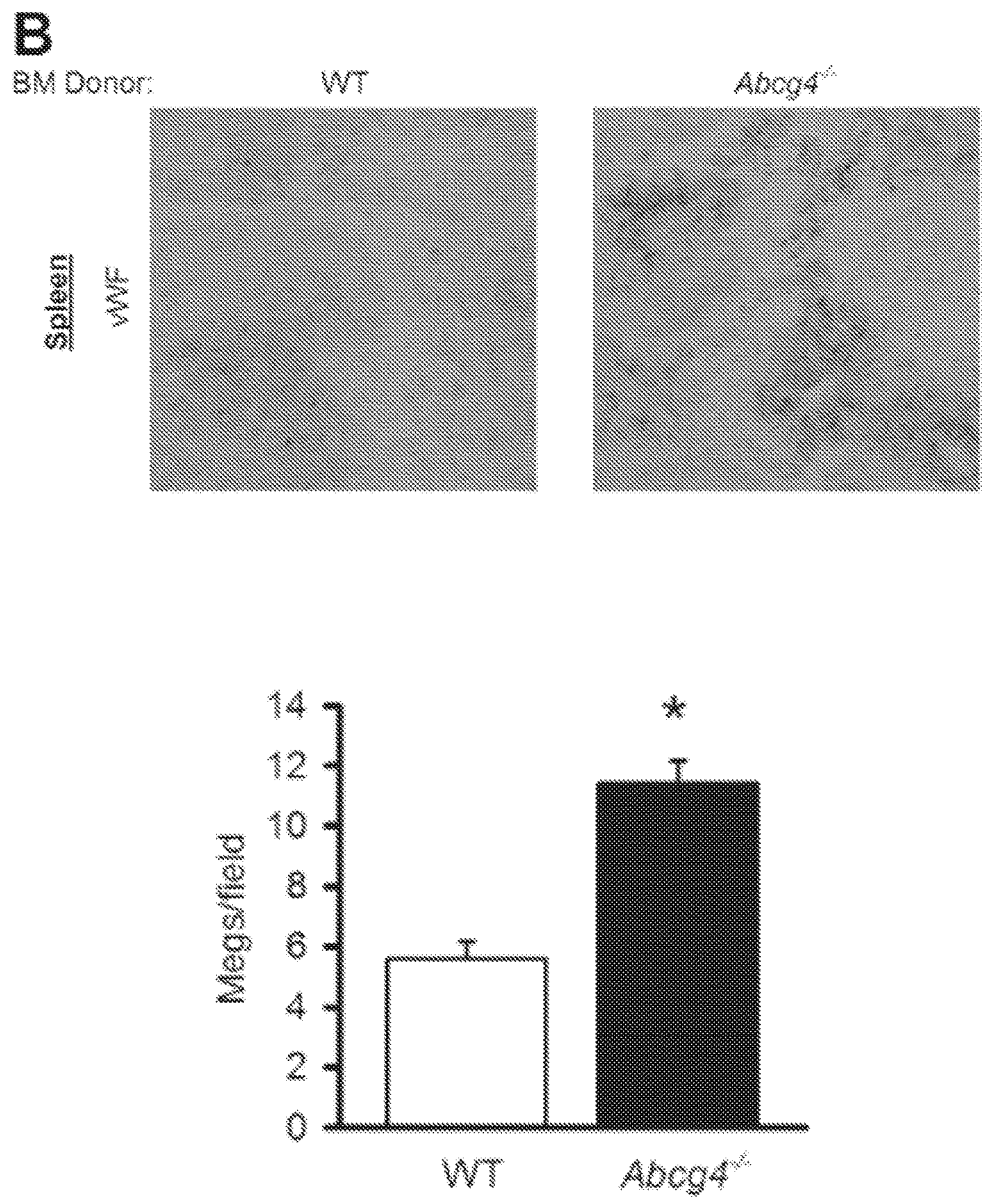

TPO is the most important growth factor regulating megakaryocyte/platelet lineage development in vivo (Kaushansky, K. 2008). Platelet counts are tightly regulated by a negative feedback regulatory mechanism involving c-MPL at the surface of megakaryocytes and platelets which serves as a clearance sink for TPO, and thus limits the increase in platelet count that results from increased TPO/ c-MPL signaling in BM cells (Kaushansky, K. 2008; Tiedt, R. et al. 2009). No changes were observed in plasma TPO levels of Abcg4$^{-/-}$ BMT mice (FIG. 11A). Increased levels of c-MPL on the surface of Abcg4$^{-/-}$ MkPs and CD41$^{lo}$/ CD71$^{lo}$ MEPs were discovered (FIG. 2C), but not megakaryocytes or platelets (FIG. 11B-C) This is consistent with Abcg4 expression profiles and the hypothesis that increased MkP proliferation is the underlying mechanism of thrombocytosis. Indeed, there was increased EdU incorporation into DNA in MEPs from Abcg4$^{-/-}$ mice (FIG. 11D). Colony formation assays showed a 2.5-fold increase in the number of megakaryocyte colonies developing in ABCG4 deficient BM compared to WT in response to TPO (FIG. 2D). Moreover, the number of megakaryocytes was increased in the BM and spleen of Abcg4$^{-/-}$ BM Ldlr$^{-/-}$ recipient mice (FIG. 12A-B). These findings suggested that ABCG4 deficiency in MEPs and MkPs results in increased cell surface levels of c-MPL, increasing sensitivity of cells to TPO and enhancing platelet production. To test this hypothesis in vivo, TPO was administered to WT and Abcg4$^{-/-}$ mice. Giving exogenous TPO to animals may overwhelm the negative feedback regulatory mechanism, uncovering effects of increased c-MPL activity (Kelemen, E. et al. 1999). When injecting recombinant TPO into chow-fed WT or Abcg4$^{-/-}$ mice, the increase in platelets was much more pronounced in Abcg4$^{-/-}$ mice (2.1-fold) compared to WT mice (1.4 fold) (FIG. 2E). These results indicate that ABCG4 deficiency renders the mice more responsive to TPO in vivo, consistent with increased MkP c-MPL levels as the mechanism underlying increased platelet production and levels in Abcg4$^{-/-}$ mice. Interestingly, Abca1-/-Abcg1-/- mice show increased expansion of LSK, GMP and leukocytes but not MEP and platelet count (Yvan-Charvet, L. et al. 2010). The distinct gene expression patterns and BM and blood cell phenotypes displayed in these transporter deficient mice indicate no overlapping functions of ABCG4 with ABCA1 and ABCG1 in hematopoiesis.

Figure 2F:
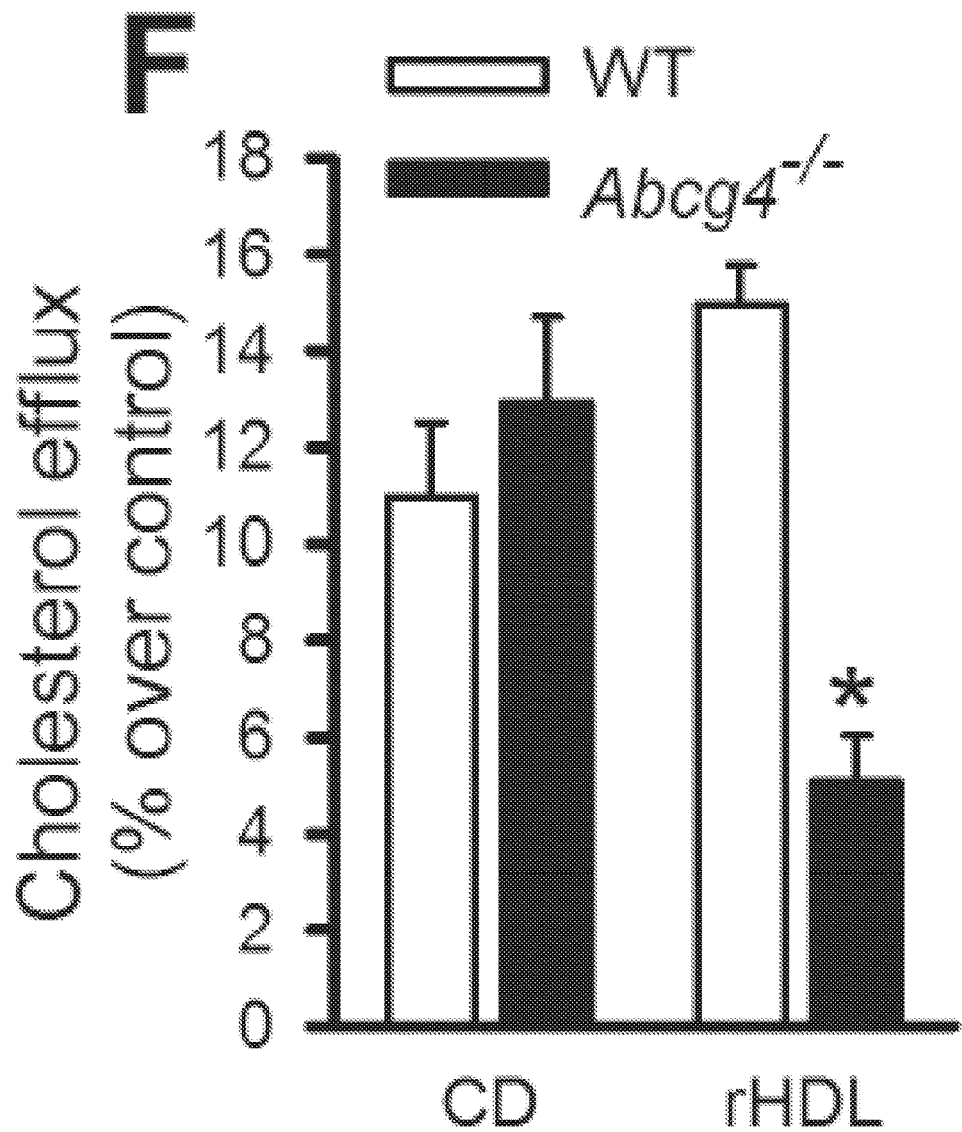

To elucidate potential mechanisms linking ABCG4 deficiency to increased c-MPL and proliferation and expansion of MkPscellular cholesterol efflux from the WT or Abcg4$^{-/-}$ MkPs was examined using a novel fluorescent cholesterol analog (BODIPY-cholesterol) based flow cytometry assay. ABCG4 deficiency markedly reduced cholesterol efflux to rHDL in Abcg4$^{-/-}$ MkPs (FIG. 2F). As a result, BODIPY-cholesterol levels in Abcg4$^{-/-}$ MkPs were significantly increased (FIG. 2G). A significant portion of the BODIPY-cholesterol that accumulated in Abcg4$^{-/-}$ MkPs appeared to be in plasma membrane (FIG. 2G). Free cholesterol content as assessed by filipin staining was also substantially increased in the plasma membrane of Abcg4$^{-/-}$ MkPs (FIG. 13A). Cholesterol accumulation is known to suppress the expression of cholesterol-responsive genes (Brown, M. S. et al. 2009). Accordingly, expression of Ldlr and Hmgcs1 was significantly decreased in Abcg4$^{-/-}$ relative to the WT MEPs but not in GMPs which do not express Abcg4 (FIG. 13C-D), again suppressing sterol accumulation in Abcg4$^{-/-}$ MEPs. Thus, even though localized to the Golgi (FIG. 10C), ABCG4 deficiency resulted in defective cholesterol efflux to HDL and an increase in cell cholesterol content including in the plasma membrane, consistent with studies suggesting segregation of sterol-rich plasma membrane domains in the trans-Golgi (Lingwood, D. et al. 2010).

To see if increases in cellular cholesterol content could recapitulate the effects of ABCG4 deficiency, cells were loaded with cholesterol/cyclodextrin complexes (CD/Chol). This led to increased WT MkP proliferation paralleling increases in cell surface c-MPL levels (FIG. 2H-I) These effects of CD/Chol were more pronounced in Abcg4$^{-/-}$ MkPs. When cells were treated with cyclodextrin (CD) to remove cellular cholesterol (Kilsdonk, E. P. et al. 1995), proliferation and cell surface levels of c-MPL were significantly reduced to a similar level in both WT and Abcg4$^{-/-}$ MkPs (FIG. 2H-I) While rHDL significantly reduced WT MkP proliferation and cell surface c-MPL, it had no effect in Abcg4$^{-/-}$ MkPs, consistent with cholesterol efflux data (FIG. 2F). In addition, removal of cellular cholesterol by CD reversed the increase in megakaryocyte colonies associated with ABCG4 deficiency (FIG. 13E). These findings suggest that ABCG4 acts to modulate MkP cell surface c-MPL levels and cell proliferation by regulation of membrane cholesterol content.

Example 3

Figure 14:
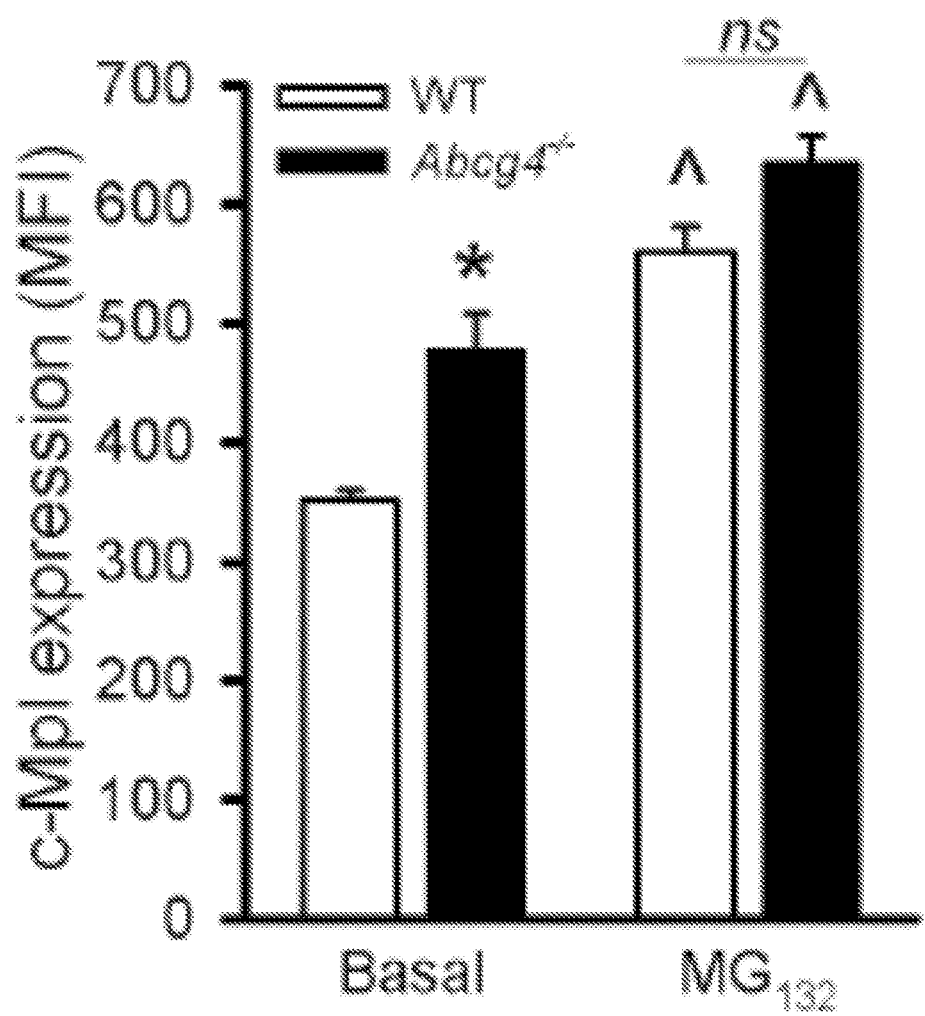
FIG. 14. Cell surface c-MPL levels with or without MG132 treatment (10 μM) for 2 h in the presence of TPO. Data is presented as mean±SEM, *P<0.05 indicates genotype effect, ˆP<0.05 indicates treatment effect.

Increased MkP cMPL and Proliferation in ABCG4 Deficiency Involves Altered Activity of c-CBL and LYN Mechanisms linking changes in cellular cholesterol levels to altered c-MPL expression in MkPs were explored. Previous studies have shown that ligand binding to various growth factor receptors, such as c-MPL or the EGFR, results in activation of a negative feedback loop involving c-CBL-mediated ubiquitinylation leading to internalization and/or degradation of the receptor (Saur, S. J. et al. 2010; Waterman, H. et al. 1999). It was assessed whether such negative feedback regulation is defective in Abcg4$^{-/-}$ MkPs. Indeed, there was dramatic blunting of c-CBL tyrosine phosphorylation in response to TPO treatment in Abcg4$^{-/-}$ MkPs compared to WT cells (FIG. 3A) while total c-CBL was unchanged (not shown). Treatment of WT MkPs with a proteasome inhibitor MG$_{132}$ increased c-MPL to a similar level in WT and Abcg4$^{-/-}$ cells (FIG. 14). Cholesterol loading by CD/Chol reduced c-CBL phosphorylation, while removal of cellular cholesterol by CD increased c-CBL phosphorylation in WT and Abcg4$^{-/-}$ MkPs (FIG. 3B). Whereas phosphorylated c-CBL was increased in WT MkPs by rHDL, rHDL failed to alter c-CBL phosphorylation in Abcg4$^{-/-}$ MkPs (FIG. 3B), consistent with failure of rHDL to modulate c-MPL levels and cell proliferation of Abcg4$^{-/-}$ MkPs. These findings suggest that impaired cholesterol efflux in Abcg4$^{-/-}$ MkPs results in defective c-CBL-mediated feedback down-regulation of c-MPL by TPO. An independent approach to manipulating cholesterol levels, involving treatment with U18666A, a compound that blocks cholesterol trafficking from late endosome or lysosomes to plasma membrane (Underwood, K. W. et al. 1998), also reversed decreased c-Cbl phosphorylation and increased cell surface c-MPL levels of Abcg4-/- MkPs.

The tyrosine kinase catalyzing c-CBL tyrosine phosphorylation in response to TPO is not known. SRC family kinases (SFK) such as LYN, FYN and c-SRC are known to phosphorylate tyrosine residues of c-CBL (Hunter, S. et al. 1999) leading to its activation and SFK inhibitors were shown to increase cell surface c-MPL levels via undefined mechanisms (Hitchcock, I. S. et al. 2008). It was hypothesized that the activity of SFK is decreased in Abcg4$^{-/-}$ MkPs, leading to decreased c-CBL phosphorylation. Indeed, treatment with SU6656, an inhibitor of LYN, FYN and c-SRC (Blake, R. A. et al. 2000), markedly decreased c-CBL phosphorylation, increased cell surface c-MPL and abolished the difference in response to TPO in WT and Abcg4$^{-/-}$ MkPs (FIG. 3C-D). Amon, SFK members, TPO activation of c-MPL increased the kinase activity of LYN and FYN but not other members of SFK (Lannutti, B. J. et al. 2003). LYN kinase is palmitoylated, membrane-associated and its activity is increased by decreased membrane cholesterol content (Oneyama, C. et al. 2009). Interestingly, Lyn$^{-/-}$ mice displayed increased megakaryocytopoiesis with mild thrombocytosis (Lannutti, B. J. et al. 2006) and mild anemia with reticulocytosis (Ingley, E. et al. 2005), phenotypes that bear a striking resemblance to that of Abcg4$^{-/-}$ mice.

Figure 4C:
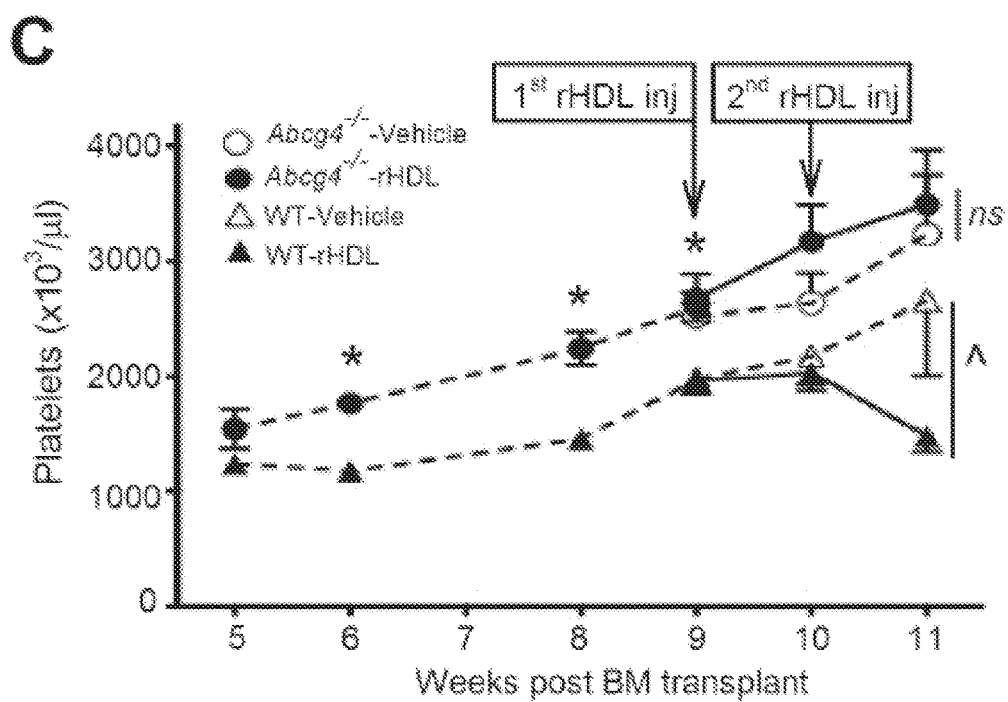
FIG. 4. WTD-fed Ldlr$^{-/-}$ recipient mice (n=5) received a single infusion of vehicle or rHDL (100 mg apoA-I/kg BW) and (A) platelet count or (B) BM MEP population was determined 5 days after infusion. (C) WT mice were transplanted with donor BM cells from WT (n=10) or Abcg4$^{-/-}$ mice (n=10), both transduced with Mpl$^{W515L}$. Mice were injected twice with vehicle or rHDL (100 mg apoA-I/kg BW) as indicated (n=5 per subgroup). Absolute mean platelet counts are shown. Following the 2$^{nd}$ rHDL injection, platelet count was significantly decreased in the WT BM but not Abcg4$^{-/-}$ BM recipient mice. Data is presented as mean±SEM, *P<0.05 WT versus Abcg4$^{-/-}$ and ^P<0.05 for treatment effect. (D) Schematic model showing ABCG4 deficiency decreases cholesterol efflux to HDL and increases cell membrane cholesterol accumulation, leading to decreased LYN kinase activation in response to TPO, decreased c-CBL tyrosine phosphorylation, decreased c-MPL ubiquitination and degradation, increased cell surface c-MPL levels, increased proliferative response of MkP to TPO, increased MkP population, increased megakaryopoiesis, increased platelet production, thrombocytosis, increased activation of leukocytes and accelerated atherogenesis and arterial thrombosis.
Figure 4D:
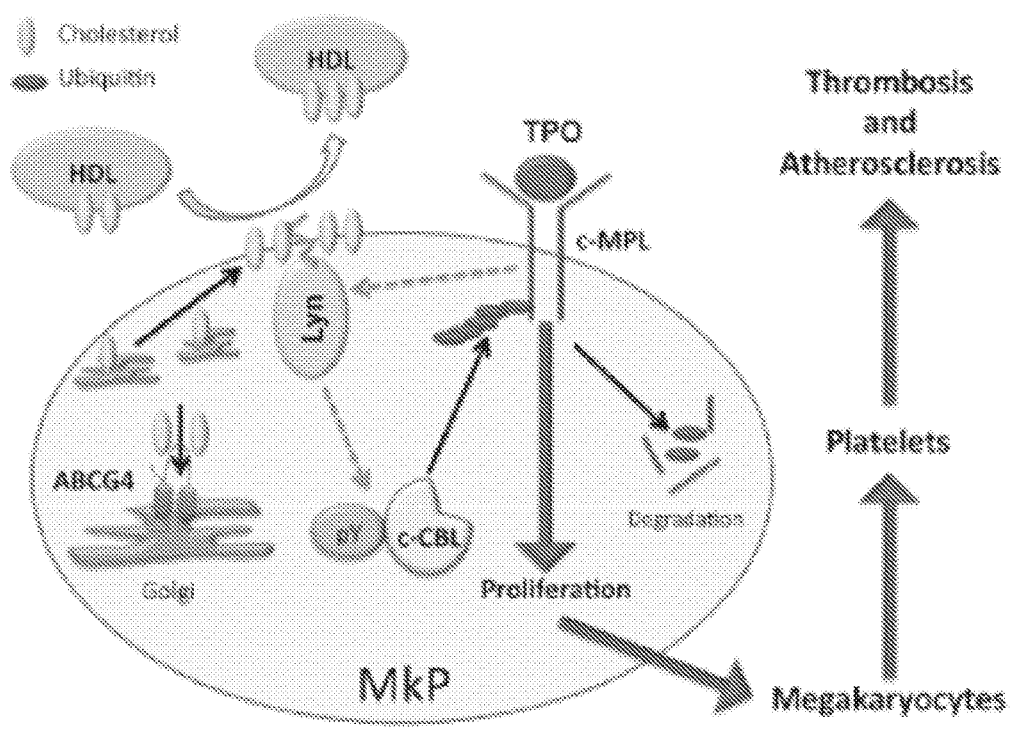

Thus, it was hypothesized that LYN might be the dominant tyrosine kinase catalyzing c-CBL tyrosine phosphorylation in response to TPO. TPO-treated Lyn$^{-/-}$ MkPs showed decreased c-CBL phosphorylation and increased cell surface c-MPL (FIGS. 3E-F) and cell proliferation (FIG. 3G), demonstrating a key role of LYN in regulation of tyrosine phosphorylation of c-CBL and MkP proliferation in response to TPO. Cholesterol loading by CD/Chol decreased c-CBL phosphorylation, increased c-MPL levels and enhanced cell proliferation in WT MkPs but had no effect in Lyn$^{-/-}$ MkPs (FIGS. 3E-G). Treatments with either CD or rHDL to induce cholesterol efflux decreased proliferation of WT MkPs. In contrast, Lyn$^{-/-}$ MkPs showed increased proliferation that was completely unresponsive to either cholesterol loading or depletion conditions (FIG. 3G). Known TPO-mediated signaling pathways were assessed that could be potentially activated in Abcg4$^{-/-}$ MkPs as a result of increased cell surface c-MPL. p-STAT5 levels were similar in WT and Abcg4$^{-/-}$ MkPs while p-ERK1/2 levels were significantly higher in Abcg4$^{-/-}$ MkPs in the basal state (FIG. 3I). TPO stimulation increased p-STAT5 and p-ERK1/2 levels in both WT and Abcg4$^{-/-}$ MkPs. Furthermore, the increase in p-ERK1/2 but not p-STAT5 levels was more pronounced in Abcg4$^{-/-}$ than in WT MkPs. This differential phosphorylation pattern mimics that seen with LYN deficiency (Lannutti, B. J. et al. 2006) and again suggests decreased LYN activity in response to TPO in ABCG4 deficiency. These findings suggest that effects of cholesterol loading and unloading on the feedback regulation of MPL by c-CBL phosphorylation may be mediated through LYN (FIG. 4D). These findings further uncover a novel role of hematopoietic ABCG4 in the regulation of plasma membrane sterol content, cell surface c-MPL levels and TPO-mediated proliferation of the MkP population, megakaryocytopoiesis and platelet levels, likely involving HDL-mediated cholesterol efflux and Lyn/c-Cbl facilitated negative regulation of c-MPL signaling.

Example 4

HDL Suppresses Platelet Production in ABCG-4 Dependent Fashion

Figure 15:
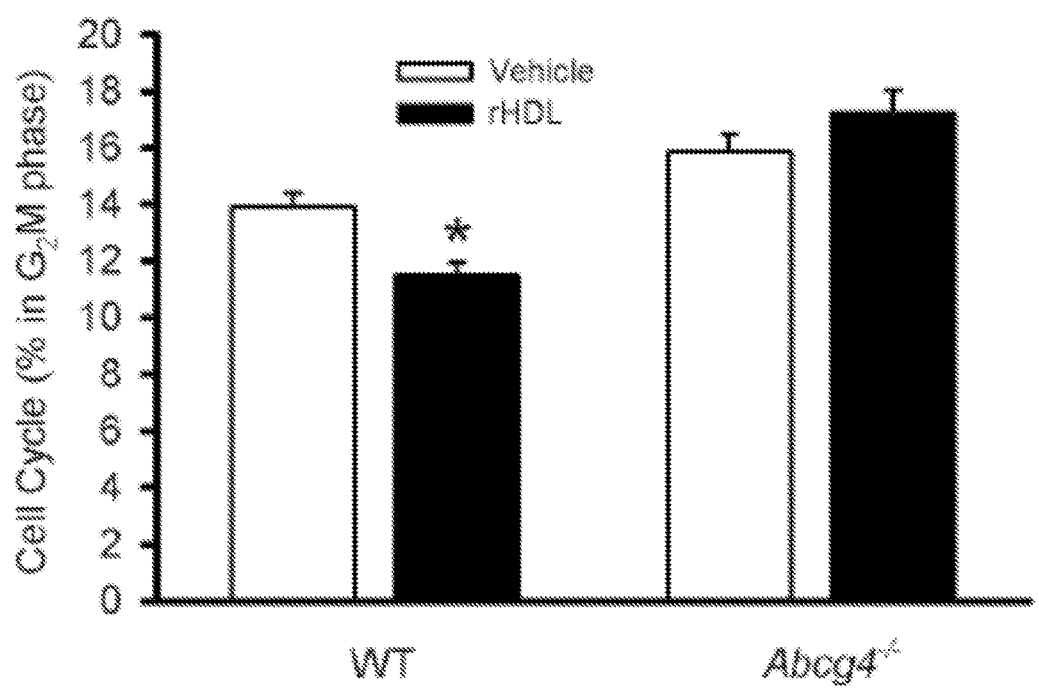
FIG. 15. WTD-fed Ldlr$^{-/-}$ recipient mice (n=5) received a single infusion of vehicle or rHDL (100 mg apoA-I/kg BW) and cell cycling of MEP population was determined 5 days after infusion as described in Extended Experimental Procedures. Data is presented as mean±SEM, *P<0.05.

Studies to assess the potential therapeutic importance of the ABCG4 pathway were carried out by determining if HDL infusion could reduce MkP proliferation and platelet counts. To test if HDL reduces MEP proliferation and platelet counts in vivo, we infused a preparation of reconstituted HDL (rHDL) that has been previously shown to reduce coronary atheroma volume in humans (Tardif, J. C. et al. 2007), into WTD-fed Ldlr$^{-/-}$ mice that had been transplanted with WT or Abcg4$^{-/-}$ BM. rHDL but not saline infusion significantly decreased platelet counts by ~30% in the WT BM→Ldlr$^{-/-}$ recipients (FIG. 4A). Remarkably, rHDL had no significant effect on the platelet count in Abcg4$^{-/-}$ BM→Ldlr$^{-/-}$ recipients. Effects on blood platelets paralleled decreased numbers and proliferation of MEPs in rHDL-infused mice that had received WT BM, while mice that had received Abcg4$^{-/-}$ BM showed no effect (FIG. 4B and FIG. 15). These findings demonstrate an essential role of ABCG4 in mediating the ability of rHDL to reduce MEP proliferation and the platelet count. We further explored the therapeutic potential for rHDL to reduce platelet counts in a mouse model of MF and ET, involving retroviral transduction of BM cells with an activating mutant form of MPL (W515L) found in human MPNs and active in mice (Pikman, Y. et al. 2006; Koppikar, P. et al. 2010). Such MPL mutations are found in a subset of patients with MF (~10%) and ET (~4-5%), and cause growth factor independent proliferation of MEPs, megakaryocyte expansion and thrombocytosis (Tefferi, A. et al. 2011; Pikman, Y. et al. 2006). The activity of this mutant form of MPL requires cell surface localization (Marty, C. et al. 2009), and since cell surface c-MPL level was increased in Abcg4$^{-/-}$ mice (FIG. 2C), this suggested that its activity might be enhanced by ABCG4 deficiency. Indeed, compared to WT mice, thrombocytosis developed more rapidly and was more pronounced in Abcg4$^{-/-}$ mice transduced with Mpl$^{W515L}$ (FIG. 4C). While rHDL infusions effectively reversed thrombocytosis in WT mice expressing MPL(W515L), similar treatments had no effect on the platelet count in Abcg4$^{-/-}$ mice expressing MPL(W515L).

Example 5 c-MPL Levels with Tolimidone

Figure 16:
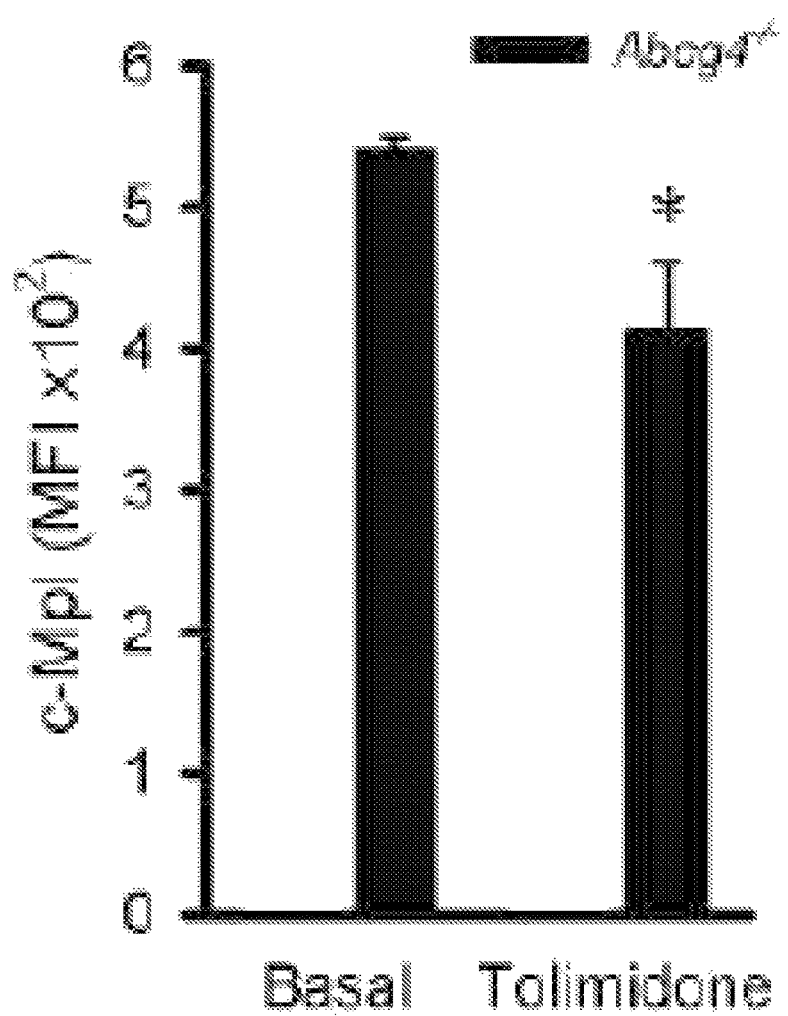
FIG. 16. c-MPL levels with or without tolimidone (10 μM) and TPO for 2 h. Error bars are S.E.M. *P<0.05 WT vs Abcg4$^{-/-}$ TPO and ˆP<0.05 for treatment effect.
Figure 20:
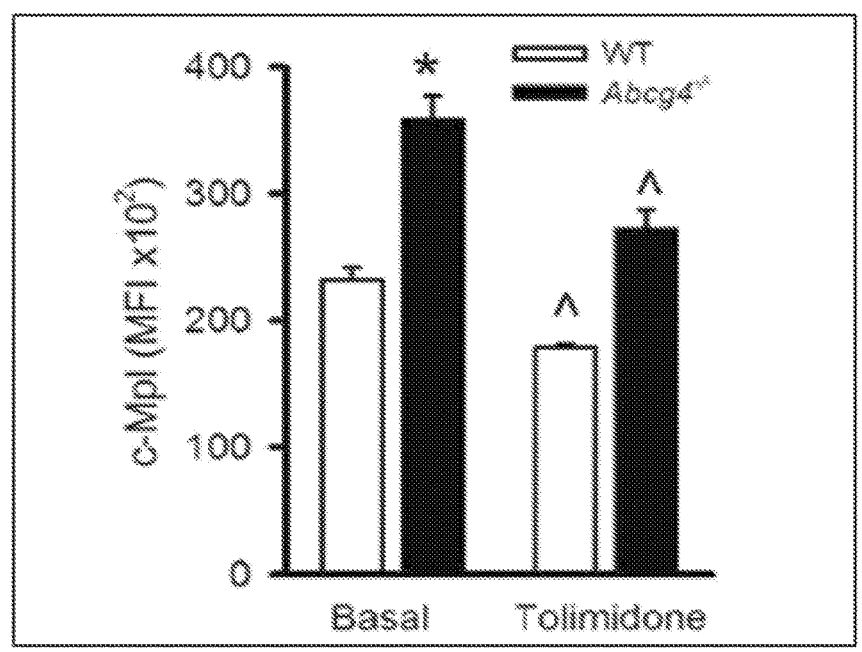
FIG. 20. Bone marrow cells isolated from Ldlr$^{-/-}$ or Ldlr$^{-/-}$/Abcg4$^{-/-}$ mice fed on a high fat high cholesterol diet for 8 weeks were treated with or without Tolimidone (10 μM) in the presence of 30 ng/ml TPO for 2 hours. Cell surface c-Mpl levels in MkPs were determined by flow cytometry. *p<0.05 between genotypes and ˆp<0.05 between Tolimidone treatment.

Treatment of Abcg4$^{-/-}$ MkPs with Tolimidone, a compound which selectively increases LYN kinase activity and exerts its in vivo effects in a LYN-dependent fashion, significantly reduced cell surface c-MPL levels (FIG. 16). Treatment of bone marrow cells from hypercholesterolemic Ldlr$^{-/-}$ mice with Tolimidone significantly reduced cell surface c-MPL levels in WT and Abcg4$^{-/-}$ MkPs (FIG. 20).

Example 6

Lyn Kinase Activators

Various analogues of Tolimidone, which are also Lyn kinase activators, are expected to have analogous activity to Tolimidone. Other Lyn kinase activators, which are structurally different from Tolimidone, are expected to have analogous activity to Tolimidone. Such analogues are expected to reduce cell surface c-MPL levels in WT and Abcg4$^{-/-}$ MkPs. Such analogues are expected to reduce cell surface c-MPL levels in WT and Abcg4$^{-/-}$ MkPs from hypercholesterolemic mice.

Example 7

Delineate the Mechanisms Linking Defective Cholesterol Efflux to HDL from MkPs to Accelerated Atherosclerosis Defective cholesterol efflux from MkPs to HDL due to ABCG4 deficiency causes increased plasma membrane cholesterol levels, decreased Lyn kinase activity and reduced tyrosine-phosphorylation and E3 ligase activity of c-Cbl in response to TPO. This causes an increase in cell surface c-MPL levels, leading to enhanced MkP proliferation, megakaryopoiesis and thrombocytopoiesis. The resulting thrombocytosis associated with increased platelet activity and leukocyte activation accelerates atherogenesis.

Figure 17A:
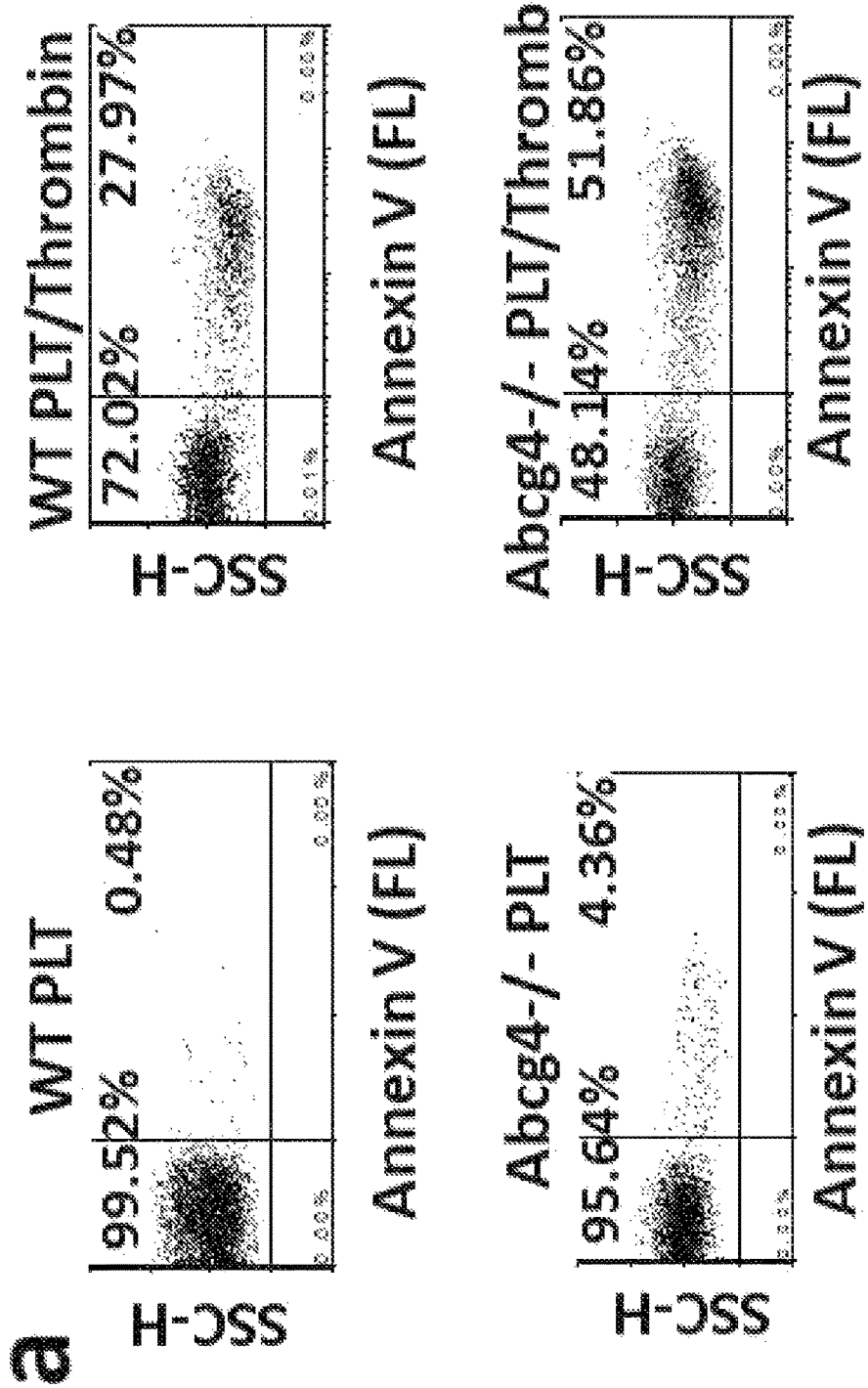
FIG. 17. Increased platelet annexin V binding and accelerated thrombin formation associated with ABCG4 deficiency. Purified platelets (PLT) from WTD-fed Ldlr$^{-/-}$ recipient mice were simulated with or without thrombin, fixed and incubated with annexin V and analyzed by flow cytometry (a,b). (c) Thrombelastography analysis of blood samples from the recipient mice. (d) R time: latency for initial fibrin formation. (e) SEMS: shear elastic modulus strength, an estimate of the formed thrombus strength.
Figure 17B:
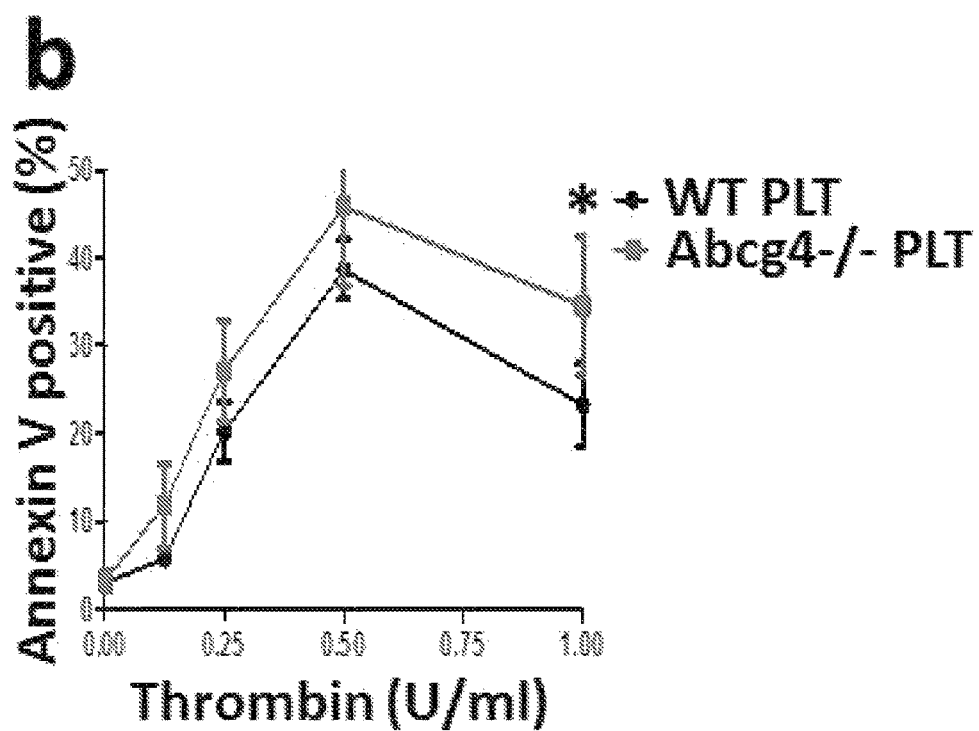
Figure 17C:
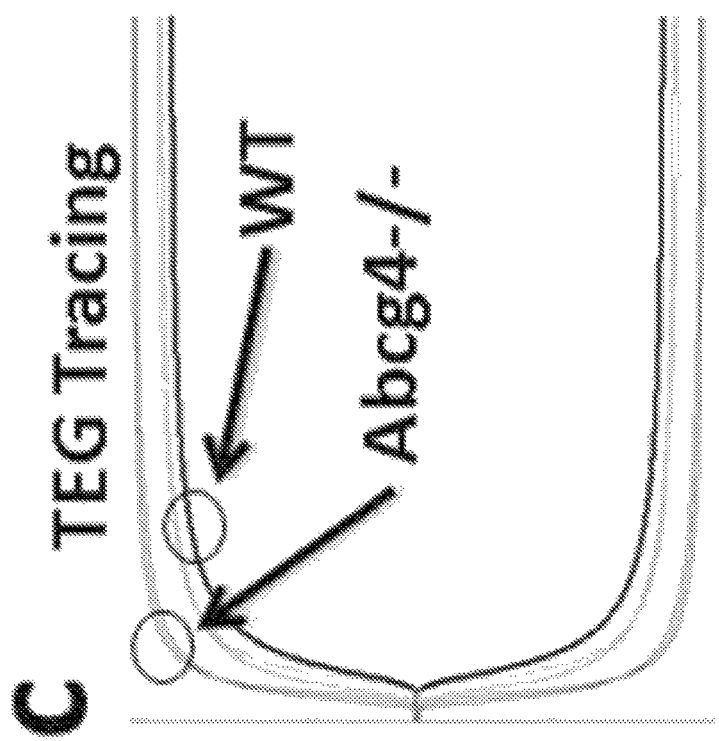

There is increased platelet microparticle generation and increased activation of leukocytes in platelet/leukocyte aggregates in Abcg4$^{-/-}$ BMT mice. These findings may indicate increased platelet production and an increased population of young, more active platelets (Karpatkin, S. & Garg, S. K. 1974; Weintraub, A. H. et al. 1974). Increased platelet microparticle generation has been shown in platelets stimulated by potent platelet activators or under high shear stress, in association with increased membrane externalization of phosphatidylserine (PS) (Barry, O. P. et al. 1997; Schoenwaelder, S. M. et al. 2009; Reininger, A. J. et al. 2006)). To determine PS levels at platelet surface, annexin V binding was used. Platelets from the WTD-fed Ldlr$^{-/-}$ recipient reconstituted with Abcg4$^{-/-}$ BM showed increased annexin V binding, with or without thrombin stimulation (FIG. 17A-B). It has been well documented that increased platelet membrane PS externalization enhances thrombin generation, leading to increased thrombosis (Kaplan, Z. S. & Jackson, S. P. 2011). The PS-rich platelet-derived microparticles were first identified as an activity supporting thrombin generation in platelet poor plasma (Wolf, P. 1967). It was hypothesized that thrombocytosis, increased platelet microparticles and increased PS externalization associated with BM ABCG4 deficiency would increase atherothrombosis. As an initial test, thrombelastography (TEG) was sused. Thrombus formation was initiated by mixing 340 µl citrated whole blood taken from the WTD-fed $Ldlr^{-/-}$ recipient mice with 20 µl 2M $CaCl_2$ in the TEG device and real-time monitored for 2 hours (FIG. 17C). Indeed, these studies showed an accelerated thrombus formation (FIG. 17D), with increased shear elastic modulus strength (FIG. 17E), an estimate of the formed thrombus strength, associated with ABCG4 deficiency. These data, while preliminary, suggest a mechanism that would lead to increased arterial thrombus formation in hypercholesterolemic mice with BM ABCG4 deficiency.

These studies are repeated with a larger number of samples to confirm these initial findings. If confirmed, we will further evaluate thrombin formation/activation by quantifying thrombin-antithrombin III complex generated in vivo in the recipient mice with ELISA assays. For evaluation of arterial thrombosis in vivo, the $FeCl_3$ carotid injury model is considered state of the art (Eckly, A. et al. 2011). $FeCl_3$-induced carotid artery thrombosis in the mouse models will be examined (Gui, T. et al. 2007). Briefly, a filter paper soaked with 10% $FeCl_3$ solution is be placed around the exposed carotid artery adjacent to the probe (Transonic Systems Inc.) to initiate oxidative injury to the artery and induce thrombosis. The blood flow is real-time and ultrasonically monitored. In addition, although mice are resistant to spontaneous athero-thrombosis, this possibility is assessed by careful examination of atherosclerotic plaques in H&E sections of proximal aorta, coronary and brachiocephalic arteries.

Example 8

Assess the Causal Relationship Between Aberrant Platelet Production and Accelerated Atherosclerosis Associated with BM ABCG4 Deficiency It is hypothesized that increased platelet production induced by BM ABCG4 deficiency is the major cause of increased atherosclerosis in hypercholesterolemic mice. Thrombocytosis or thrombocytopenia in WTD-fed $Ldlr^{-/-}$ mice transplanted with WT or $Abcg4^{-/-}$ BM is induced and examined for the impact on atherogenesis. Romiplostim is a prescription TPO mimetic drug with a long half-life (Imbach, P. et al. 2011). Romiplostim specifically interacts with c-MPL, stimulating c-MPL-mediated signaling and increasing platelet counts in mice and other species (Broudy, V. C. & Lin, N. L. 2004). Since BM ABCG4 deficiency induces thrombocytosis likely by enhancing c-MPL signaling, romiplostim recapitulates the effect of ABCG4 deficiency on atherogenesis in hypercholesterolemic mice. Vehicle or romiplostim is given intraperitoneally to the WTD-fed $Ldlr^{-/-}$ recipients transplanted with BM from WT or $Abcg4^{-/-}$ mice. Thrombocytosis induced by romiplostim moderately accelerated atherosclerosis in the WT BM recipients relative to the WT BM recipients treated with the vehicle (Table 2). It is expected that much more pronounced thrombocytosis in the $Abcg4^{-/-}$ BM recipients treated with romiplostim, as TPO infusion and ABCG4 deficiency have a synergistic effect to increase platelet production (FIG. 2E). This could lead to more pronounced atherogenesis in the $Abcg4^{-/-}$ BM recipient mice. The sample size of all proposed studies in this application is estimated by power calculation based on the preliminary studies using the program from www.biomath.info/power. For instance, in our atherosclerosis studies, the sample size to have 80% probability of detecting a 30% change in lesion area at a $p<0.05$ level of significance is 12 mice per group. Due to natural loss of mice in the course of the studies, 15 female 7-8 week old mice per group are used.

TABLE 2

| BM Donor | BM Recipient | Treatment | Predicted atherolesion |
| --- | --- | --- | --- |
| WT | $Ldlr^{-/-}$ | Vehicle | 2+ |
| | | Romiplostim | 3+ |
| $Abcg4^{-/-}$ | $Ldlr^{-/-}$ | Vehicle | 3+ |
| | | Romiplostim | 4+ |
| WT | $Ldlr^{-/-}$ | Isotype Control | 2+ |
| | | Anti-platelet | 1+ |
| $Abcg4^{-/-}$ | $Ldlr^{-/-}$ | Isotype Control | 3+ |
| | | Anti-platelet | 1+ |

Since it is hypothesized that there is a causal relationship between thrombocytosis associated with increased leukocyte activation and accelerated atherosclerosis in ABCG4 deficiency, it is anticipated that a reversal of the enhanced atherogenesis by depletion of platelets. Anti-mouse CD41 antibodies are used to deplete platelets, as reported (Katsman, Y. et al. 2010). Indeed, preliminary studies indicate ~80% depletion of platelets and reversal of leukocyte activation by administration of the anti-CD41 antibodies but not the isotype matched IgG1κ control. The isotype control or anti-CD41 are injected intraperitoneally twice a week for 8 weeks at 600 µg/kg body weight into the WTD-fed $Ldlr^{-/-}$ recipients reconstituted with BM from WT or $Abcg4^{-/-}$ mice. The anti-CD41 markedly reduces the platelet count and decrease overall atherogenesis in WT and $Abcg4^{-/-}$ groups relative to the control IgG1κ groups and reverse the increased atherogenesis associated with BM ABCG4 deficiency (Table 2). A reversal of the increased leukocyte activation and elevated levels of platelet microparticles is anticipated. An 8 week treatment is selected in order to 1) examine the effects on early atherogenesis and 2) minimize adverse effects caused by repeated injection of antibodies. In addition to the atherogenesis studies, thrombus formation is examined using TEG as described in Aim1-A in these animal models as well. It is expected that the accelerated thrombus formation associated with BM ABCG4 deficiency is reversed by platelet depletion but exacerbated by the TPO mimetics. A leading hypothesis to account for the role of platelets in atherogenesis is that activated platelets interact with lesional endothelial cells, depositing platelet-derived chemokines (RANTES, PF4), triggering monocyte recruitment and arrest (Huo, Y. et al. 2003). To test this, the level of RANTES and PF4 associated with aortic lesional endothelium from these mice with or without BM ABCG4 deficiency and with or without anti-CD41 or romiplostim treatment is determined (Huo, Y. et al. 2003). Thrombocytosis associated with ABCG4 deficiency or romiplostim treatment may increase RANTES deposition, which should be reversed by anti-CD41 administration.

Alternative, genetic approaches to reversing thrombocytosis associated with ABCG4 deficiency and examining the effect on atherogenesis are also used. For instance, $Mpl^{h1b219}/Mpl^{h1b219}$ mice in B6 background from the Jackson Laboratory carry a point mutation in c-MPL and display a marked reduction of megakaryopoiesis and platelet count (Chan, E. R. et al. 2009). $Abcg4^{-/-}/Mpl^{h1b219}/Mpl^{h1b219}$ mice can be generated and WTD-fed $Ldlr^{-/-}$ recipients reconstituted with BM from WT, $Abcg4^{-/-}$, $Mpl^{h1b219}/Mpl^{h1b219}$ or $Abcg4^{-/-}/Mpl^{h1b219}/Mpl^{h1b219}$ mice are used to examine the effect of altered thrombocytopoiesis on atherogenesis.

Example 9

Assess the Role of Lyn and c-Cbl in ABCG4-mediated Modulation of c-MPL Signaling The studies herein as well as the published literature suggest sequential actions of Lyn and c-Cbl in the negative regulation of c-MPL signaling. ABCG4-dependent HDL-mediated cholesterol efflux may reduce c-MPL signaling by increasing Lyn and c-Cbl activity. This hypothesis is further investigated using chemical activators or inhibitors of Lyn or c-Cbl as well as genetic modulation of Lyn or c-Cbl activity.

Tolimidone is a potent and selective Lyn tyrosine kinase activator (Saporito, M. S. et al. 2012) that is being tested as a therapy for diabetes in human. The drug is available from Activate Scientific, Germany (Catalog No. AS9568). Tolimidone decreased cell surface c-MPL levels and proliferation of WT MkPs in association with increased c-Cbl phosphorylation in response to TPO. Tolimidone also reverses increased cell surface c-MPL, and increases c-Cbl phosphorylation and decreases cell proliferation of $Abcg4^{-/-}$ MkPs in response to TPO.

In contrast, tolimidone should have no effects in $Lyn^{-/-}$ MkPs. Importantly, it is expected that the effects of the Lyn kinase activator are c-Cbl-dependent. A novel inhibitor of c-Cbl that is specific and does not inhibit the E3 ligase activity of Cbl-b, a Cbl family member highly homologous to c-Cbl, has been obtained. It is expected that the effects of tolimidone are reversed by the c-Cbl inhibitor, in both WT and $Abcg4^{-/-}$ MkPs. c-Cbl inhibitor alone should increase MkP surface c-MPL levels and proliferation in response to TPO and these effects should not be affected by the Lyn activator. In addition, c-Cbl deficient mice are obtained from Taconic Farms. Increased MkP surface c-MPL and proliferation in response to TPO and increased megakaryopoiesis in these mice is expected. Importantly, tolimidone treatment or manipulation of cellular cholesterol content by CD, CD-chol or rHDL will has no effect on c-Cbl$^{-/-}$ MkP surface c-MPL levels and proliferation in response to TPO. These studies place c-Cbl downstream of Lyn in the negative feedback regulation and confirm the dominant role of Lyn and c-Cbl in HDL-mediated modulation of MkP c-MPL signaling. These studies are performed ex vivo using BM cells from the relevant mouse models, cultured in the presence or absence of the indicated inhibitors or activators from one hour up to hours, a time frame sufficient to induce the changes of the parameters we plan to examine, as suggested in our preliminary studies.

The ability of tolimidone 1) to reverse thrombocytosis and accelerated atherosclerosis associated with ABCG4 deficiency and 2) as a therapy for atherosclerosis, is assessed. Lyn activation limits thrombocytopoiesis and thrombocytosis associated with ABCG4 deficiency and hypercholesterolemia, leading to reduced atherosclerosis. Tolimidone is incorporated into the WTD at a dose of 10 mg/kg BW to 50 mg/kg BW. 10 mg/kg has shown an oral-active anti-ulcer activity in rats (Lipinski, C. A. et al. 1980), an indication for which this agent was originally developed. The efficacy of tolimidone to limit thrombocytosis in the WTD-fed $Ldlr^{-/-}$ recipient reconstituted with $Abcg4^{-/-}$ BM is evaluated. Tolimidone or vehicle is given for 12 weeks to the WTD-fed female $Ldlr^{-/-}$ recipient reconstituted with WT or $Abcg4^{-/-}$ BM.

The smallest change in lesion area between the test groups is 30%. The sample size to have 80% probability of detecting a 30% change at a p<0.05 level of significance is 12 mice per group. Thus, 15 mice/group are used for the study, in anticipation of some natural loss. BM and splenic MkP and Mk count, platelet count and aortic atherosclerotic lesions are determined. Tolimidone reduces all of these parameters in both WT and $Abcg4^{-/-}$ BM recipient and reverses the increased atherosclerosis associated with ABCG4 deficiency.

Lyn activation could reduce atherosclerosis in hypercholesterolemic mouse models through multiple mechanisms, such as increasing insulin sensitivity (Ochman, A. R. et al. 2012) or decreasing TLR2/4 induced macrophage activation (Keck, S. et al. 2010). However, Lyn activation specifically abolishes the increase in platelet counts in atherogenesis due to ABCG4 deficiency. Thus, the effect is to reduce atherosclerosis in both WT and $Abcg4^{-/-}$ BMT mice and to eliminate the difference between the genotypes. Insulin sensitivity, blood monocyte and neutrophil counts and inflammatory responses in mouse peritoneal macrophages are also monitored to aid in the interpretation of the studies.

Example 10

Assess the Impact of MPN on Atherogenesis and Atherothrombosis, and Potential for rHDL Infusions as a Treatment ET and MF substantially increase risk of atherothrombosis and its complications but this has not been modeled in animals (Campbell, P. J. & Green, A. R. 2006). rHDL-mediated suppression of thrombocytosis induced by a MPN-causing MPL mutant (FIG. 4C) suggests the potential of rHDL infusion as a therapy for MPN-induced atherothrombosis.

MPL(W515L) induced thrombocytosis and leukocytosis in hypercholesterolemic mice increases atherosclerosis, and possibly induces atherothrombosis, with reversal by elevation of plasma HDL levels. First, a mouse model for this is created to test the impact on atherothrombosis and atherogenesis. Second, elevation of HDL or pharmacological activation of Lyn kinase as means to limit or reverse the phenotypes associated with MPL(W515L) induced MPN in mouse models is assessed.

MPL(W515L) induced myeloproliferation increases atherogenesis and atherothrombosis. To test this, 15 irradiated female $Ldlr^{-/-}$ mice/group (Table 3) are reconstituted with the c-MPL or c-MPL(W515L) transduced WT or $Abcg4^{-/-}$ BM cells. The mice are fed a chow diet for three weeks to allow the reconstitution to take place, then fed the WTD for 10 weeks. The atherosclerotic lesion area, leukocyte and platelet counts, platelet microparticle levels, BM and splenic MkP and Mk count, CD11b expression in platelet-associated neutrophils and monocytes, annexin V binding to platelets, thrombin activation will be determined as detailed above. BM and spleen reticulin staining are examined as an estimate for meylofibrosis. Thrombelastography is used to estimate thrombosis ex vivo by looking for evidence of spontaneous atherothromobosis. In addition, induced carotid artery thrombosis is carried out as a way to evaluate arterial thrombotic outcomes. BM ABCG4 deficiency increases atherosclerosis. MPL(W515L) expression induces myeloproliferation and thrombocytosis. Thrombocytosis induced by MPL(W515L) is more pronounced than that induced by ABCG4 deficiency, as evidenced by the marked MPL(W515L)-induced thrombocytosis in the chow-fed WT mice (FIG. 4C) relative to the 10% increase in platelet count in the chow-fed Abcg4$^{-/-}$ mice. Thus, MPL(W515L) leads to more prominent atherosclerosis (Table 3). ABCG4 deficiency in combination with BM MPL(W515L) expression further increases platelet count to a level above that induced by MPL(W515L) expression alone (FIG. 4C). Therefore, giving the most pronounced atherosclerosis in the Abcg4$^{-/-}$/MPL(W515L) group among the four groups tested. The induced carotid artery thrombosis studies are performed in a separate set of mice when positive results are obtained with the atherosclerosis studies. The induced carotid artery thrombosis in these models parallels the effects on platelet counts and functions and lesion area.

TABLE 3

| BM Donor | MPL | BM Recipient | Predicted atherogenesis |
|---|---|---|---|
| WT | WT | Ldlr$^{-/-}$ | 1+ |
| Abcg4$^{-/-}$ | WT | Ldlr$^{-/-}$ | 2+ |
| WT | W515L | Ldlr$^{-/-}$ | 3+ |
| Abcg4$^{-/-}$ | W515L | Ldlr$^{-/-}$ | 4+ |

Example 11

Assess Elevation of HDL as a Potential Therapy for MPNs

Raising plasma HDL levels suppress MPL(W515L) induced thrombocytosis and reduce atherogenesis and atherothrombosis associated with the induced thrombocytosis. To test this, we have designed a study as shown in Table 4. MPL(W515L) transduced WT or Abcg4$^{-/-}$ BM are transplanted into Ldlr$^{-/-}$ recipient mice. After 3 weeks to allow for BM reconstitution, the mice are fed the WTD for 10 weeks. During the last 4 weeks, the four groups of mice are infused with vehicle or rHDL (80 mg/kg body weight) via the tail vein, once every four days for total of seven injections. Then, aortic atherosclerosis, platelet count and other phenotypes are examined. 20 female recipient mice per group are used for the study. There is a more pronounced thrombocytosis and atherosclerosis in the Abcg4$^{-/-}$ BM recipient relative to the WT BM recipient receiving vehicle treatment. Also, there is reduced thrombocytosis, atherosclerosis in the WT BM recipient receiving rHDL relative to the WT BM recipient receiving the vehicle. This expected result would indicate a potential therapeutic effect of rHDL infusion for MPNs. In contrast, the rHDL infusion failed to reduce thrombocytosis in the Abcg4$^{-/-}$ BM recipient, as evidenced in the studies shown in FIG. 4C, but reduce atherosclerosis albeit less potently than in the WT BM recipient, since rHDL could still work by other mechanisms to favorably impact atherogenesis, such as promoting cholesterol efflux from macrophage foam cells or reducing monocytosis (Campbell, P. J. & Green, A. R. 2006). These studies provide important insights into evaluation of raising HDL as a therapy for MPNs as well as the underlying mechanism, such as whether suppression of MPL(W515L) induced MEP and/or MkP proliferation constitutes a major mechanism responsible for rHDL-mediated suppression of thrombocytosis in our models. Similarly, Lyn activators limit c-MPL and c-MPL(W515L) signaling and reduce c-MPL(W515L) induced thrombocytosis and, possibly, other MPN phenotypes in mice, including increased atherosclerosis. Similar experiment as detailed in Table 3 are carried out replacing rHDL with tolimidone. Unlike rHDL, tolimidone reduces thrombocytosis in the Abcg4$^{-/-}$ BM recipient, as tolimidone reverses the effects of ABCG4 deficiency on MEP/MkP cell surface c-MPL levels and the receptor-mediated proliferative signaling. These studies are extended to examine the effects of rHDL or tolimidone administration on atherothrombosis.

TABLE 4

| BM Donor | MPL | BM Recipient | Infusion | Predicted atherogenesis |
|---|---|---|---|---|
| WT | W515L | Ldlr$^{-/-}$ | Vehicle | 3+ |
| WT | W515L | Ldlr$^{-/-}$ | rHDL | 1+ |
| Abcg4$^{-/-}$ | W515L | Ldlr$^{-/-}$ | Vehicle | 4+ |
| Abcg4$^{-/-}$ | W515L | Ldlr$^{-/-}$ | rHDL | 2+ |

While rHDL infusions represent a reasonable approach to test the impact of increased HDL on MPL(W515L) induced MPN development, multiple injections over long period of time in animals could have unwanted effects, such as generation of anti-human apoA-I antibodies (Shah, P. K. et al. 1998). If this arises, transgenic apoA-I expression are used in future studies with a design similar to that of Table 3 but Ldlr$^{-/-}$ and Ldlr$^{-/-}$apoA-I$^{tg}$ mice are used as recipients to replace rHDL infusion.

Example 12

Delineate the Mechanisms and Consequences of HDL-mediated Cholesterol Efflux from Human MkP, Mk and Platelets ABCG4 expression has been detected in human erythroid progenitor cells (http://biogps.org/#goto=genereport&id=64137) and Mks, suggesting a direct role of ABCG4 in megakaryopoiesis as in the mouse. However, unlike mouse, human platelets express high levels of ABCG4 mRNA. Gene expression atlases show a substantially higher ABCG4 mRNA level in human platelets than in white blood cells (http://www.ebi.ac.uk/gxa/experiment/E-GEOD-2006/ENSG00000172350).

Figure 18C:
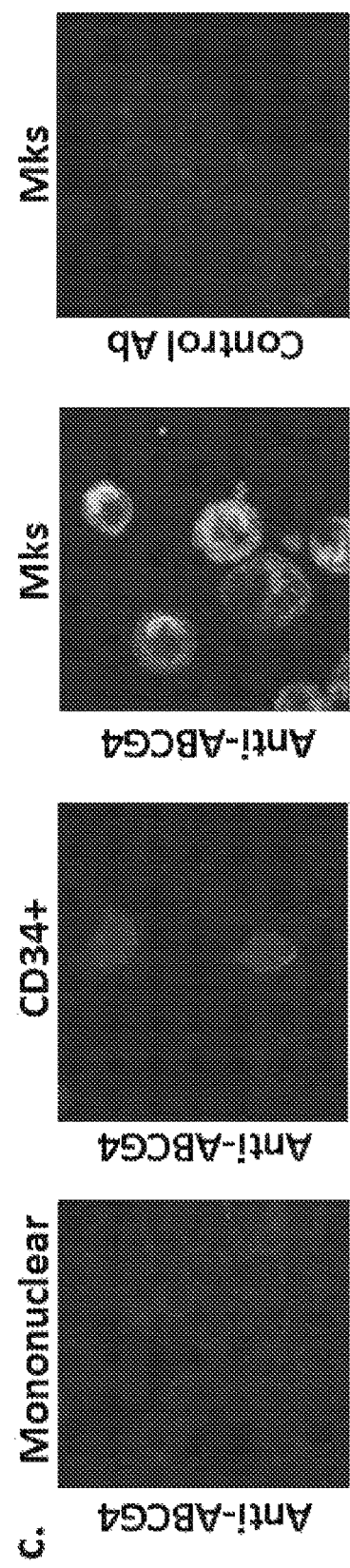
FIG. 18. ABCG4 exoressin in human megakaryocytes. The relative mRNA expression in human platelet or peripheral blood mononuclear cells (a). Human cord blood mononuclear cells, CD34+ cells or CD34+ cells derived megakaryocytes (b) determined by q-PCR. (c) Immunofluorescence confocal microscopy of human cells derived from the cord blood.

Also, ABCG4 mRNA in human peripheral blood platelets and mononuclear cells have been quantified. Indeed, ABCG4 mRNA levels were high and comparable to that of SCARB1 in human platelets (FIG. 18A). SCARB1 is known to be highly expressed in human platelets (Calkin, A. C. et al. 2009) and plays a significant role in regulation of platelet activity (Brodde, M. F. et al. 2011). Consistent with the mouse data, ABCG4 mRNA levels in human mononuclear cells were very low. In contrast, ABCA1 and ABCG1 mRNA levels were low in human platelets and high in mononuclear cells. To further test this, Mononuclear cells from human cord blood were isolated and CD34$^+$ cells from the mononuclear cells were harvested by FACS. The CD34$^+$ cells were cultured in a defined medium with TPO and other growth factors for 2 weeks to promote Mk differentiation, according to an established protocol used to produce large quantity of platelets ex vivo (Cortin, V. et al. 2009). >90% of the cells are CD41$^+$, Mk-like cells after 2 weeks of culture (Cortin, V. et al. 2009). ABCG4 mRNA levels were markedly increased while ABCA1 and ABCG1 mRNA levels were down-regulated during differentiation from the CD34$^+$ cells to Mk (FIG. 18B). The relative expression of ABCG4 was low while the expression of ABCA1 and ABCG1 was high in cord blood derived mononuclear cells (FIG. 18B). To examine ABCG4 protein expression in human Mk, immunofluorescence microscopy was performed in human cord blood derived mononuclear cells, CD34$^+$ cells and CD34$^+$ cell derived Mks, using mono-specific anti-ABCG4 and control antibodies (FIG. 18C). This showed high ABCG4 expression in Mks but low expression in the mononuclear cells and CD34$^+$ cells. The control antibody showed low background non-specific staining of human Mks. Together these findings suggest that differentiation of human HSPCs toward the megakaryocyte lineage in response to TPO markedly increases ABCG4 expression, and suggest that ABCG4 may have a direct role in regulation of cellular cholesterol efflux/distribution in human Mks and platelets.

Example 13

Determine the Role of ABCG4 in Cholesterol Efflux to HDL from Human MkP, Mk and Platelets siRNA- or shRNA-mediated suppression of mRNA expression are used to examine the specific role of ABCG4 in human MkP, Mk and platelet cholesterol efflux, a strategy that has been successfully adopted in a similar setting using human CD34$^+$ cell derived megakaryocytes and platelets to determine the function of specific genes (Gilles, L. et al. 2009). Human cord blood are obtained from New York Blood Center. ABC transporter-dependent BODIPY-cholesterol efflux to apoA-I or HDL from cultured macrophages has been reported (Sankaranarayanan, S. et al. 2011). The method was successfully adopted to study cholesterol efflux from BM hematopoietic cells by flow cytometry (FIG. 2F). Lentiviral shRNA-IRES-GFP constructs are created to transduce the CD34$^+$ cell-derived megakaryocytes, as described (Gilles, L. et al. 2009). Alternatively, Amaxa's Nucleofector has been shown to efficiently introduce siRNAs into suspension primary cell cultures (Maurisse, R. et al. 2010). Efficiency of down-regulation is determined by q-PCR and confocal immunofluorescence microscopy with our anti-ABCG4 antibody. When shRNA-IRES-GFP constructs are used, GFP-positive Mks or platelets will be analyzed for down-regulation of ABCG4 expression or cholesterol efflux by qPCR, immunofluorescence confocal microscopy and flow cytometry as described in our preliminary studies. For efflux assays, Mks or platelets will be briefly incubated with CD/BODIPY-cholesterol, washed, and then incubated with or without various amounts of ApoA-I, HDL or rHDL for 3 hours. The fluorescence intensity of cells without incubation with the cholesterol acceptors will be considered as the basal state. Any decrease in fluorescence intensity caused by incubation with the acceptors indicates efflux of the tracer. Cell-specific markers helps to define the specific cell populations. If positive, these studies are extended to cholesterol mass efflux as determined by gas-liquid chromatography. While particular attention is given to the potential role of ABCG4, it is equally important to assess the roles of other potential players. There are seemingly conflicting data regarding the role of platelet SR-BI in regulation of platelet cholesterol efflux and activity. An earlier study indicated that rHDL but not native HDL inhibited platelet activation by promoting cholesterol efflux in a platelet SR-BI independent fashion (Calkin, A. C. et al. 2009). In contrast, another study showed that inhibition of mouse and human platelet activation by HDL was SR-BI dependent (Brodde, M. F. et al. 2011). To add to the complexity, this study also suggested that SR-BI-mediated signaling but not cholesterol efflux was responsible for the inhibitory effects of HDL (Brodde, M. F. et al. 2011).

In order to dissect the specific role of ABCG4 and SR-BI in human MkP, Mk and platelet cholesterol efflux, BODIPY-cholesterol efflux to apoA-I, spherical plasma HDL or cholesterol-poor rHDL is assessed with or without single or combined inhibition of ABCG4 or SR-BI, by down-regulation of ABCG4 expression and/or SR-BI blocking antibodies (NB400-113, Novus Biologicals) or SR-BI inhibitors (BLT-1 from Millipore).

Based on our earlier work suggesting that SR-BI promotes cholesterol efflux to a cholesterol-poor acceptor such as rHDL, but not to a cholesterol enriched acceptor such as plasma HDL (Ji, Y. et al. 1997; Yvan-Charvet, L. et al. 2008, SR-BI promotes efflux to rHDL but not plasma HDL, while ABCG4, an ATPase, promotes cholesterol efflux to both. Based on its high levels of expression also it is also anticipated that ABCG4 may be the predominant player in cholesterol efflux from Mks and platelets. If ABCG4 expression is not sufficiently downregulated using the strategy proposed, the long-term goal is to develop an ABCG4 specific antagonist, aiming to test it as a novel approach to raising platelet counts in human idiopathic thrombocytopenic purpura. BODIPY-cholesterol efflux from 293 cells overexpressing ABCG4 are used as the assay for high throughput screening of chemical libraries. An ABCG4 specific antagonist could be used as an alternative to explore the role of ABCG4 in cholesterol efflux to HDL from human MkPs, Mks and platelets.

The role of ABCG4 in human MkP proliferation and megakaryopoiesis is also assessed. Human CD34$^+$ cells are harvested from the cord blood and transduced with the mock or ABCG4 specific lentiviral shRNA-IRES-GFP constructs. The cells are cultured in the defined medium with TPO to promote Mk/platelet lineage development. 48 hours after transduction, GFP-positive human MEPs and MkPs, defined as Lin$^-$CD34$^+$CD38$^+$IL3Ra$^-$CD45RA$^-$ and Lin$^-$CD34$^+$CD38$^+$IL3Ra$^-$CD45RA$^-$CD41$^+$CD71$^{lo}$ cells, are harvested. ABCG4 mRNA levels, cholesterol efflux to HDL, rHDL or CD, cellular and membrane cholesterol content, cell surface c-MPL levels, c-CBL phosphorylation and cell proliferation in response to TPO is determined as described herein. Human Mk colony formation assays are performed using the harvested GFP-positive cells to assess the role of ABCG4 in human megakaryopoiesis, and are extended to studies of thrombocytopoiesis by assessing the quantity of platelets produced from these cells ex vivo. Again, these studies could be complemented using human BM derived cells and ABCG4 specific antagonist, when available.

Example 14

Effects of Altered Human Platelet Cholesterol Efflux on Platelet Activity ex vivo Once a positive role of ABCG4 in promotion of cholesterol efflux from human platelets is identified, the effects of ABCG4 deficiency on platelet reactivity to various agonists ex vivo, particularly after cholesterol-loading of the platelets with CD-chol, are determined. Enrichment of platelets with cholesterol is known to increase platelet reactivity (Korporaal, S. J. et al. 2010; Shattil, S. J. et al. 1975). Platelets harvested from ex vivo production as with or without ABCG4 knock-down are used for these studies. Platelet P-selectin expression, β3 integrin activation levels and annexin V binding are detected by flow cytometry as described (Reheman, A. et al. 2009) on resting or activated platelets in response to thrombin or ADP treatment, with or without cholesterol loading and native HDL-, rHDL- or CD-promoted cholesterol efflux.

While some of the tested biological activities of platelets produced ex vivo appear to be normal (Cortin, V. et al. 2009), the functional properties of these platelets have not been rigorously examined. The insights obtained from studies of these platelets may not fully represent the properties of mature platelets in human blood. Thus, the role of ABCG4 in the experimental settings described in Example 11 as well as cholesterol efflux to HDL is be explored in platelets from adult human blood, once ABCG4 specific antagonist are available.

Example 15

Figure 19:
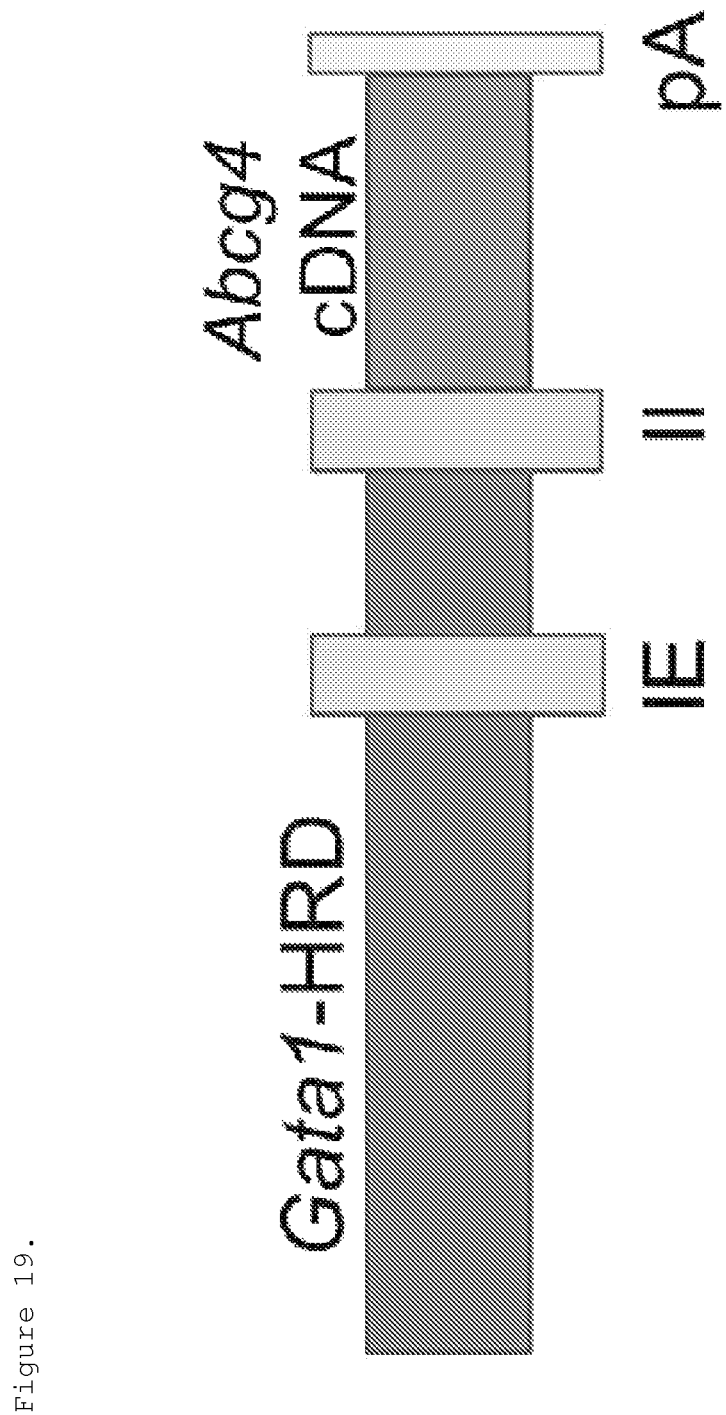
FIG. 19. Gata1-HRD-Abcg4 transgene. Gata1-HRD minigene containing exons IE and II of mouse Gata1 gene is ligated to ABcg4 cDNA. pA represents the polyadenylation signal.

Create a Mouse Model Similar to Humans by Transgenic Expression of ABCG4 in Mks and Platelets The Gata1-hematopoietic regulatory domain (Gata1-HRD) is used as the promoter for Abcg4 transgene expression, which is likely to promote expression of ABCG4 in Mks and platelets, as occurs in humans (Suzuki, N. et al. 2002). GATA1 is a transcription factor essential for normal development of Mks in vivo (Shivdasani, R. A. et al. 1997). A minigene construct including the Gata1-HRD region has been shown to direct specific megakaryocyte lineage expression[126], including high expression in Mks and platelets. cDNAs have been used with this minigene construct for successful transgene expression (Suzuki, N. et al. 2002). Thus, mouse Abcg4 cDNA is used to create the construct (Wang, N. et al. 1998) (FIG. 19). Five transgenic lines are created with varying expression levels of Abcg4 in order to 1) replace endogenous Abcg4 expression in Abcg4$^{-/-}$ mice, and 2) to examine effects of overexpression at different levels, in a Mk lineage-specific fashion. After initial breeding to expand the colonies, the level of Abcg4 mRNA and protein in MEPs, MkPs, LSK, CMP as well as in Mks, platelets and white blood cells, are characterized. Lines with replacement levels of Abcg4 mRNA are selected as well as two additional lines with moderate or high levels of overexpression of Abcg4 mRNA. The transgenic mice are crossbred with Abcg4$^{-/-}$ mice to generate Abcg4$^{-/-}$Abcg4$^{Tg}$ mice.

Defects associated with general Abcg4 deficiency such as increased MEP/MkP proliferation and expansion, enhanced megakaryopoiesis and increased thrombocytopoietic response to TPO infusion are reversed by Abcg4 transgenic expression at replacement levels are confirmed. Next, similar studies are carried out using two transgenic lines that overexpress Abcg4. It is possible that the transgenic Abcg4 overexpression result in reduced MEP/MkP proliferation and reduced platelet levels. If a robust ABCG4 expression is detected in Mk and platelets, as occurs in humans, cholesterol efflux and platelet reactivity assays as detailed above will be performed, with or without SR-BI antibodies or inhibitors to assess the relative role of ABCG4 and SR-BI on cholesterol efflux and platelet activation.

This set of experiments serves as a proof that replacement of ABCG4 in MkPs and Mks reverses the effects of BM ABCG4 deficiency on platelet counts and activity. The overexpression experiment also has the potential to determine a potential therapeutic benefit of reducing MkP proliferation and platelet counts, that could in the future be tested in models of MPNs such as the MPL variant.

Example 16

Tolimidone Suppressed c-MPL(W515L)-induced Megakaryopoiesis

Figure 21D:
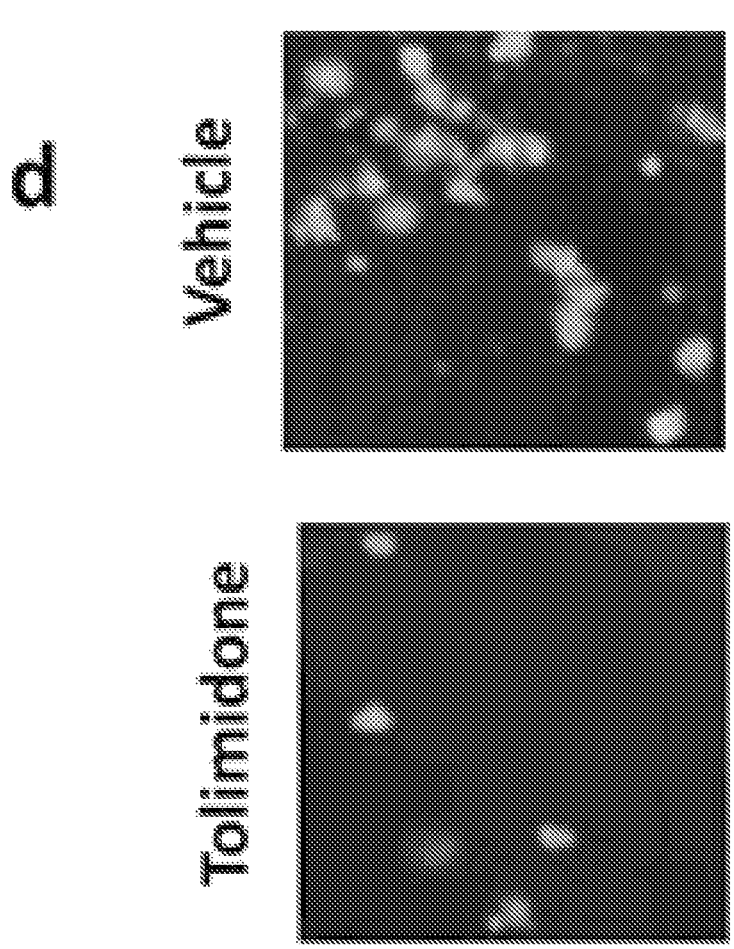
FIG. 21. BM cells of the recipient transplanted with BM cells expressing c-MPL(W515) were cultured for 10 days in the presence of IL-3 (10 mg/mL) and TPO (1 ng/mL) with or without tolimidone (10 μM). Megakaryocyte (Mk) colonies expressing c-MPL (W515) were identified by cell morphology and GFP expression. Identity of MK was also confirmed by staining for acetylcholinesterase activity. Count of Mk colonies (a); Mk count per colony (b); total colony per plate (c); fluorescence microscopy of a single colony (d). *p<0.05 between vehicle and tolimidone treatment.

Long-term, repeated rHDL infusions are less desirable relative to orally bioavailable small molecule compounds in treatment of chronic diseases such as MPNs. Tolimidone reduces surface MPL levels of Abcg4$^{-/-}$ MkPs and platelet count in Abcg4$^{-/-}$ mice, suggesting the that tolimidone recapitulates the impact of rHDL and reduces thrombocytosis in mice with hematopoietic expression of MPL (W515L). To assess the possibility that tolimidone limits megakaryopoiesis and thrombocytosis induced by c-MPL (W515), megakaryocyte colony formation assays with BM cells derived from mice with retroviral co-expression of c-MPL(W515L) and GFP in BM cells were used. Tolimidone significantly reduced the number of GFP-positive megakaryocyte colonies and GFP-positive megakaryocytes in each colony (FIG. 21A-B). Under the conditions of low TPO (1 ng/ml), the majority of cell colonies were non-megakaryocyte colonies. Importantly, tolimidone treatment did not significantly affect the total number of colonies (FIG. 21C), indicating that tolimidone at 10 µM did not have a general cytotoxic effect but selectively inhibited proliferation of c-MPL(W515L) positive megakaryocyte progenitor cells.

Example 17

Tolimidone Suppressed JACK2(V671F)-induced Megakaryopoiesis

Activating JAK2 mutations, such as JAK2(V617F), are the most prevalent mutations identified in patients with MPNs. Recent studies indicate that the mutant JAK2 requires expression of homo- or heterodimeric receptors for full activation of cell proliferation signaling. It has been proposed that the dimeric cytokine receptors participate in the activation of JAK2-V617F, presumably by providing a scaffolding function where two JAK2(V617F) molecules could properly be juxtaposed to allow for transphosphorylation and subsequent full activation of the tyrosine kinase. Since activation of LYN is expected to down-regulate cell surface c-MPL levels, pharmacological activation of LYN may reduce JAK2(V617F) activation in MkPs by limiting the levels of the receptor and, thereby, ameliorate the MPN phenotypes.

Figure 22C:
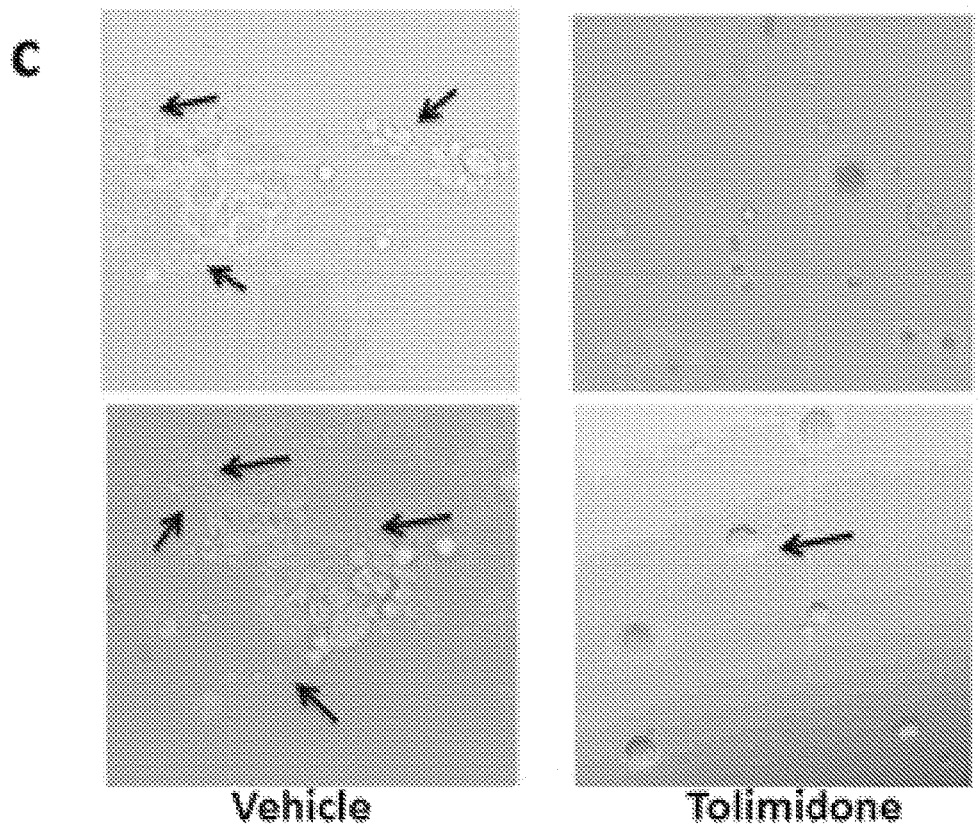
FIG. 22. BM cells from Jak$^{2+/VF}$/Vav$^{cre}$ mice were plated and cultured for 14 days in the presence of IL-3 (10 mg/mL) and TPO (1 ng/mL) with or without tolimidone (10 μM). Megakaryocyte (Mk) colony was identified by cell morphology. Colony number/plate (a); Mk count/colony (b); and representative Mk colonies (c). Arrows indicate the projected proplatelet like structures from mature megakaryocytes. *p<0.05 between vehicle and tolimidone (10 μM).

In order to assess this possibility, megakaryocyte colony formation assay with BM cells derived from Jak2+/VF/Vavcre mice were performed. Tolimidone treatment decreased the number of megakaryocyte colonies and the number of megakaryocytes in each colony (FIG. 22A-B). Moreover, many of the mature megakaryocytes in the vehicle group started to form long-projected cell structures resembling proplatelets. In contrast, tolimidone treatment reduced the proportion of megakaryocytes that generated proplatelets (FIG. 22C). These results indicated that tolimidone inhibits megakaryopoiesis induced by JAK2(V617F) and are useful for treatment of MPNs resulting from somatic activating mutations of JAK2.

Discussion

The idea that cellular sterol metabolism is intimately connected to proliferative responses is longstanding (Brown, M. S. & Goldstein J. L. 1974; Chen, H. W. et al. 1974). However, specific molecular mechanisms that link control of cell proliferation to cholesterol efflux pathways have only recently been defined. These studies elucidate a novel signaling pathway linking membrane cholesterol levels to growth factor receptor levels and cell proliferation, specifically in MkPs, but with the potential to be more widely applicable to the understanding of control of cell proliferation by cell cholesterol content.

The role of ABCG4 in regulation of human Mk and platelet production and activity is also studied. This work is likely to generate widespread interest on the relationship between HDL-mediated cholesterol efflux pathways, proliferation of MkPs, megakaryocytopoiesis, platelet production, platelet activation and atherogenesis, and the novel role of ABCG4 in regulating these processes. On a clinical level, this work is relevant to ongoing phase 3 trials in patients at risk for athero-thrombosis, involving rHDL infusions and other HDL raising treatments. Moreover, our work reveals a potential therapeutic niche for rHDL infusions in the treatment of thrombocytosis associated with ET and MF. Other potential applications include assessing pharmacological activation of Lyn kinase as a therapy for ACD and MPNs, and potential new therapeutic approaches to the treatment of idiopathic thrombocytopenic purpura.

Platelet Production

A major challenge to understanding the causal relationship between aberrant platelet production or reactivity and atherogenesis has been a relative paucity of appropriate animal models. In contrast to the extensive literature relating leukocytosis and macrophage functions to atherogenesis (Libby, P. et al. 2011; Moore, K. J. & Tabas, I. 2011), studies on the role of platelets in atherogenesis are few, in part due to this limitation. Previous studies have involved infusing purified platelets into animals to examine effects on atherogenesis with apparent limitations such as activation of platelets ex vivo (Huo, Y. et al. 2003), or multiple injections of platelet antibodies (Massberg, S. et al. 2002). Based on the lack of literature reports, animal studies modeling the relationship between MPNs, thrombocytosis and atherosclerosis appear to be unique. Studies are based on an innovative use of flow cytometry and BODIPY-cholesterol to monitor signaling pathways and sterol efflux pathways in BM cells. Studies in human MkPs and Mks use a novel method for differentiating these cells from cord blood. Uncovering Lyn kinase as a potential sensor of membrane cholesterol content in c-Cbl-mediated negative feedback regulation of c-MPL signaling provides novel opportunities for understanding the interactions between cholesterol metabolism and cell proliferation or cell inflammatory responses, as c-Cbl is commonly involved in negative regulation of many growth factor- or cytokine-mediated signaling pathways (Schmidt, M. H. & Dikic, I. 2005). Importantly, rHDL infusion and apoA-I transgene expression in a mouse model of human MPNs with or without BM ABCG4 deficiency are novel pre-clinical approaches to evaluating elevation of rHDL infusions as a potential therapy for MPNs and to exploring the underlying mechanism.

Platelets play a key role in atherogenesis and its thrombotic complications. Although hypercholesterolemia is central to atherogenesis, a role of altered cholesterol homeostasis in promoting platelet production and thrombosis has not been explored. Transplantation of bone marrow (BM) deficient in ABCG4, a transporter of unknown function, into Ldlr$^{-/-}$ mice resulted in thrombocytosis, accelerated thrombosis and atherosclerosis. ABCG4 was selectively expressed in BM megakaryocyte progenitors (MkP) and Abcg4$^{-/-}$ MkPs displayed defective cholesterol efflux to HDL, increased cell surface levels of thrombopoietin (TPO) receptor (c-MPL) and enhanced proliferation. This reflected disruption of the negative feedback regulation of c-MPL levels by E3 ligase c-CBL and cholesterol-sensing LYN kinase. HDL infusions reduced platelet counts in hypercholesterolemic WT mice and in a mouse model of myeloproliferative neoplasm in an ABCG4-dependent fashion. HDL treatment may offer a novel approach to reducing atherothrombotic events associated with increased platelet production. HDL suppresses megakaryocyte progenitor cell proliferation and thrombocytosis by promoting cholesterol efflux via ABCG4 and may represent a novel approach to reducing atherothrombosis in myeloproliferative neoplasms.

These findings uncover a novel role of hematopoietic ABCG4 in the regulation of plasma membrane sterol content, cell surface c-MPL levels and TPO-mediated proliferation of the MkP population, megakaryocytopoiesis and platelet levels. These studies also reveal a novel mechanism in which LYN may act as a membrane cholesterol sensor, leading to decreased growth factor-mediated c-CBL phosphorylation, increased c-MPL and increased growth factor-mediated MkP proliferation. Since c-CBL-mediated feedback regulation is commonly involved in limitation of growth factor receptor-mediated proliferative responses (Kales, S. C. et al. 2010), this could also potentially represent a general mechanism linking membrane cholesterol levels to cellular proliferative responses. To our knowledge, this is the first report that directly links increased platelet production to atherogenesis and thrombosis.

Furthermore these findings suggest that suppression of MEP and MkP proliferation and thrombocytosis may represent a novel benefit of rHDL infusions. The ability of rHDL to suppress MEP/MkP proliferation and platelet counts in vivo was completely dependent on ABCG4, likely reflecting the cell type restricted pattern of expression of cholesterol efflux promoting ABC transporters (FIGS. 2 and 9), with ABCG4 predominating in MEP/MkPs. Currently, thrombocytosis in ET and MF is treated with low dose aspirin, and high risk ET patients (age>60, or prior thrombotic event) are treated with genotoxic agents such as hydroxyurea (Verstovek, S. et al. 2010). There remains a need for novel therapies for MF patients given their poor overall outcome and limited therapeutic options. The current treatments of myeloproliferative neoplasmas (MPNs) are mainly symptomatic. For ET patients, asprin is given to patients at low risk and genotoxic agents such as hydroxyurea are Interferon alpha-2B, a drug less convenient, less efficient and more expensive than hydroxyurea, is sometimes given as an alternative and it has its own side effects. For PM, the only known cure is allogeneic stem cell transplantation, but this approach involves significant risks. Other treatments include irradiation and chemotherapy as well as other supportive therapies which do not alter the course. Recently, JAK2 inhibitors have been developed as a treatment of PM. The efficacy and long-term effect of this approach is not known.

The present findings suggest that rHDL infusions may specifically reverse MPL-dependent MEP proliferation and aberrant megakaryopoiesis underlying thrombocytosis in ET and MF. rHDL infusions may also reduce athero-thrombotic events associated with increased platelet production in other pathological states.

Lyn Kinase

The phenotypes of hematopoietic ABCG4 deficient mice and the underlying mechanism responsible for the phenotypes were determined (FIG. 4D). Hypercholesterolemic bone marrow (BM) ABCG4 deficient mice showed thrombocytosis and accelerated atherosclerosis and arterial thrombosis (FIGS. 1 and 2). Thrombocytosis detected in Abcg4$^{-/-}$ mice was associated with increased leukocyte/platelet aggregate formation, increased leukocyte activation, increased levels of platelet-derived microparticles and increased percentage of reticulated platelets, a young, more reactive platelet sub-population. All these contribute to atherogenesis and athero-thrombosis and likely explain for the increased atherosclerosis and induced arterial thrombosis in vivo.

Further studies identified a high and selective expression of Abcg4 in BM megakaryocyte progenitor cells (MkPs) but low or no expression in other bone marrow or peripheral blood cells and ABCG4 deficiency caused decreased cholesterol efflux from MkPs to HDL and increased cholesterol accumulation in these cells. MkPs are cells that give rise to megakaryocyte and mature megakaryocytes produce platelets. The increased cellular and membrane cholesterol accumulation in MkPs due to ABCG4 deficiency led to elevated levels of cell surface thrombopoietin (TPO) receptor, c-MPL, and increased proliferative response of MkPs to TPO, in association with increased BM and spleen megakaryocyte population.

ABCG4-deficient mice also showed more pronounced increase in platelet count in response to infusion of exogenous TPO. Together, these studies strongly suggested that increased cell surface c-MPL levels as well as enhanced response of MkPs to TPO underpinned thrombocytosis and accelerated atherogenesis and atherothrombosis associated with BM ABCG4 deficiency in vivo. Megakaryopoiesis is tightly controlled by a negative feedback regulation. It has been shown that binding of TPO to c-MPL not only initiates the proliferation signaling in the target cells, but also activates c-CBL by tyrosine phosphorylation. c-CBL is an E3 ligase and activated c-CBL promotes ubiquitination and degradation of c-MPL, thus limiting cell surface levels of c-MPL and cell proliferation signaling mediated by TPO and c-MPL (Saur, S. J et al. 2010). Additional mechanistic studies suggested that increased cell surface levels of c-MPL in Abcg4$^{-/-}$ MkPs were likely due to disruption of this negative feedback regulation of c-MPL by c-CBL and c-CBL phosphorylation in response to TPO, a readout of c-CBL activation, was markedly reduced in Abcg4$^{-/-}$ MkPs (FIG. 3A). Cholesterol loading by CD/Chol reduced c-CBL phosphorylation, while removal of cellular cholesterol by CD increased c-CBL phosphorylation in WT and Abcg4$^{-/-}$ MkPs (FIG. 3B). Whereas phosphorylated c-CBL was increased in WT MkPs by rHDL, rHDL failed to alter c-CBL phosphorylation in Abcg4$^{-/-}$ MkPs (FIG. 3B), consistent with failure of rHDL to modulate c-MPL levels and cell proliferation of Abcg4$^{-/-}$ MkPs. These findings suggest that impaired cholesterol efflux in Abcg4$^{-/-}$ MkPs results in defective c-CBL-mediated feedback down-regulation of c-MPL by TPO.

The kinase catalyzing c-CBL tyrosine phosphorylation in response to TPO is not known. TPO activation of c-MPL increased the kinase activity of LYN and FYN but not other members of SFK (Lannutti, B. J. et al. 2003). LYN kinase is palmitoylated, membrane-associated and its activity is increased by decreased membrane cholesterol content (Oneyama, C. et al. 2009). Interestingly, Lyn$^{-/-}$ mice displayed increased megakaryocytopoiesis with mild thrombocytosis (Lannutti, B. J. et al. 2006) and mild anemia with reticulocytosis (Ingley, E. et al. 2005), phenotypes that bear a striking resemblance to that of Abcg4$^{-/-}$ mice. Thus, we hypothesized that LYN might be the dominant tyrosine kinase catalyzing c-CBL tyrosine phosphorylation in response to TPO. TPO treated Lyn$^{-/-}$ MkPs showed decreased c-CBL phosphorylation and increased cell surface c-MPL (FIGS. 3E-G) and cell proliferation (FIG. 3G), demonstrating a key role of LYN in regulation of tyrosine phosphorylation of c-CBL and MkP proliferation in response to TPO. Cholesterol loading by CD/Chol decreased c-CBL phosphorylation, increased c-MPL levels and enhanced cell proliferation in WT MkPs but had no effect in Lyn$^{-/-}$ MkPs (FIG. 3E-G). Treatments with either CD or rHDL to induce cholesterol efflux decreased proliferation of WT MkPs. In contrast, Lyn$^{-/-}$ MkPs showed increased proliferation that was completely unresponsive to either cholesterol loading or depletion conditions (FIG. 16). These findings suggest that effects of cholesterol loading and unloading on c-CBL phosphorylation, MPL levels and MkP proliferation may be mediated through LYN.

Since it was hypothesized that LYN was a membrane cholesterol sensor and increased membrane cholesterol content in Abcg4$^{-/-}$ MkPs inhibited LYN activity in response to TPO, leading to disrupted negative feedback regulation and increased cell surface c-MPL, we expected that increased LYN activation, such as by LYN activators, would reverse the increased c-MPL. Indeed, treatment of Abcg4$^{-/-}$ MkPs with Tolimidone, a compound which selectively increases LYN kinase activity and exerts its in vivo effects in a LYN-dependent fashion (Saporito, M. S. et al. 2012), significantly reduced cell surface c-MPL levels (FIG. 16). A novel mechanism was identified in which Tolimidone, a specific LYN kinase activator, may reduce atherosclerosis and atherothrombotic risks associated with increased platelet productions including myoproliferative neoplasms.

Studies were carried out to assess the potential therapeutic importance of the ABCG4 pathway by determining if HDL infusion could reduce MkP proliferation and platelet counts. To test if HDL reduces MEP proliferation and platelet counts in vivo, we infused a preparation of reconstituted HDL (rHDL) into WTD-fed Ldlr$^{-/-}$ mice that had been transplanted with WT or Abcg4$^{-/-}$ BM. rHDL but not saline infusion significantly decreased platelet counts by ~30% in the WT BM→ Ldlr$^{-/-}$ recipients (FIG. 4A) but not on the platelet count in Abcg4$^{-/-}$ BM→Ldlr$^{-/-}$ recipients. Effects on blood platelets paralleled decreased numbers and proliferation of MEPs in rHDL infused mice that had received WT BM, while mice that had received Abcg4$^{-/-}$BM showed no effect (FIG. 4B).

The therapeutic potential for rHDL to reduce platelet counts in a mouse model of MF and ET was explored involving retroviral transduction of BM cells with an activating mutant form of MPL(W515L) found in human MPNs and active in mice (Pikman, Y. et al. 2006; Koppikar, P. et al. 2010). Such MPL mutations are found in a subset of patients with MF (~10%) and ET (~4-5%), and cause growth factor independent proliferation of MEPs, megakaryocyte expansion and thrombocytosis (Tefferi, A. et al. 2011; Pikman, Y. et al. 2006). The activity of this mutant form of MPL requires cell surface localization (Marty, C. et al. 2009), and since cell surface c-MPL level was increased in Abcg4-/- mice, suggesting that its activity might be enhanced by ABCG4 deficiency. Indeed, compared to WT mice, thrombocytosis developed more rapidly and was more pronounced in Abcg4$^{-/-}$ mice transduced with MplW515L (FIG. 4C). While rHDL infusions effectively reversed thrombocytosis in WT mice expressing MPL(W515L), similar treatments had no effect on the platelet count in Abcg4$^{-/-}$ mice expressing MPL(W515L).

While human c-MPL mutant (MPL(W515L)) were used in this study to show the specific effects of HDL to reduce platelet counts, more common mutations that results in MPNs occur to the down-stream signaling molecules such as JAK2 (Tefferi, A. et al. 2010). It is expected that Tolimidone acts to limit platelet production and reduce platelet count even in patients carrying JAK2 mutations, as it has been shown that the mutant JAK2, such as JAK2(V617F), requires complex formation with growth receptors to be active (Lu, X. et al. 2008). JAK2 inhibitors have been investigated in clinical trials for treatment of MPNs and resistance to JAK2 inhibitors in some patients has been reported (Koppikar, P. et al. 2012). Tolimidone may be used alone or in combination with JAK2 inhibitors to reduce the risks associated with MPNs.

There remains a need for novel therapies for MF patients given their poor overall outcome and limited therapeutic options. While these studies were focused on the LYN- and c-CBL-mediated negative feedback regulation of c-MPL in MEPs and MkPs, this mechanism likely exists in megakaryocytes as well, as reported previously (Saur, S. J. et al. 2010). Thus, Tolimidone specifically reverses MPL-dependent MEP, MkP or even Megakaryocyte proliferation and aberrant megakaryopoiesis underlying thrombocytosis in ET and MF.

Summary

Tolimidone and other Lyn Kinase activators are useful for the treatment of 1) atherosclerotic cardiovascular diseases, including coronary heart disease, stroke and deep venous thrombosis; and 2) myeloproliferative neoplasms including ET and MF, in which they may have a specific role in controlling excessive platelet production andthrombosis.

Tolimidone has been proposed and tested as a treatment of type 2 diabetes (Saporito, M. S. et al. 2012; Ochman, A. R. et al. 2012). However, the underlying mechanism(s) proposed for the anti-diabetic effects of Tolimidone are unrelated to the mechanism described herein. The anti-diabetic activity of Tolimidone has been attributed to increasing insulin receptor sensitivity to insulin, probably by promoting phosphorylation of IRS-1 (Saporito, M. S. et al. 2012; Ochman, A. R. et al. 2012).

A novel mechanism has been identified which links aberrant cholesterol homeostasis in MkPs to increased platelet production and accelerated atherosclerosis and arterial thrombosis, via modulation of the negative feedback regulation of cell surface c-MPL levels by c-CBL and LYN kinase. HDL infusion suppresses the proliferation of these megakaryocyte progenitor cells and decreases platelet count in an ABCG4-dependent fashion in vivo, likely by acting to promote LYN kinase activity and turnover of c-MPL.

The LYN activator, Tolimidone, reduced cell surface c-MPL levels in MkPs. Thus, Tolimidone acts to increase LYN activity, promote c-MPL turnover, limit TPO-mediated proliferation signaling and reduce MkP proliferation. As a result, Tolimidone reduces megakaryopoiesis, platelet production and levels of platelet count and activation, particularly in hypercholesterolemia, resulting in decrease of the atherosclerotic and atherothrombotic risks associated with platelet production, including in myeloproliferative neoplasms (MPNs).

REFERENCES

Annilo, T. et al. Human and mouse orthologs of a new ATP-binding cassette gene, ABCG4. Cytogenetics and cell genetics 94, 196-201 (2001).

Arellano-Rodrigo E. et al. Increased platelet and leukocyte activation as contributing mechanisms for thrombosis in essential thrombocythemia and correlation with the jak2 mutational status. Haematologica. 91, 169-175 (2006).

Barry O. P. et al. Transcellular activation of platelets and endothelial cells by bioactive lipids in platelet microparticles. The Journal of clinical investigation. 99, 2118-2127 (1997).

Barry O. P. et al. Modulation of monocyte-endothelial cell interactions by platelet microparticles. The Journal of clinical investigation. 102, 136-144 (1998).

Barter P. J. et al. Effects of torcetrapib in patients at high risk for coronary events. The New England journal of medicine. 357, 2109-2122 (2007).

Beer P. A. et al. Mpl mutations in myeloproliferative disorders: Analysis of the pt-1 cohort. Blood. 112, 141-149 (2008).

Bellucci S, Michiels J J. The role of jak2 v617f mutation, spontaneous erythropoiesis and megakaryocytopoiesis, hypersensitive platelets, activated leukocytes, and endothelial cells in the etiology of thrombotic manifestations in polycythemia vera and essential thrombocythemia. Semin Thromb Hemost. 32, 381-398 (2006).

Bensinger S. J. et al. Lxr signaling couples sterol metabolism to proliferation in the acquired immune response. Cell. 134, 97-111 (2008).

Bersenev, A. et al. Lnk controls mouse hematopoietic stem cell self-renewal and quiescence through direct interactions with JAK2. *The Journal of clinical investigation* 118, 2832-2844 (2008).

Betteridge D. J. et al. Platelet function in patients with hypercholesterolaemia. European journal of clinical investigation. 24, Suppl 1:30-33 (1994).

Blake, R. A. et al. SU6656, a selective src family kinase inhibitor, used to probe growth factor signaling. Mol Cell Biol 20, 9018-9027 (2000).

Bojanic, D. D., et al. Differential expression and function of ABCG1 and ABCG4 during development and aging. Journal of lipid research 51, 169-181 (2010).

Brandt E. et al. Platelet-derived cxc chemokines: Old players in new games. Immunol Rev. 177, 204-216 (2000).

Brodde M. F. et al. Native high-density lipoproteins inhibit platelet activation via scavenger receptor bi: Role of negatively charged phospholipids. Atherosclerosis. 215, 374-382 (2011).

Broudy V C, Lin N L. Amg531 stimulates megakaryopoiesis in vitro by binding to mpl. Cytokine. 25, 52-60 (2004).

Brown, M. S. & Goldstein, J. L. Cholesterol feedback: from Schoenheimer's bottle to Scap's MELADL. Journal of lipid research 50 Suppl, S15-27 (2009).

Brown M S, Goldstein J L. Suppression of 3-hydroxy-3-methylglutaryl coenzyme a reductase activity and inhibition of growth of human fibroblasts by 7-ketocholesterol. J Biol Chem. 249, 7306-7314 (1974).

Cai H. et al. Differential transformation capacity of src family kinases during the initiation of prostate cancer. Proc Natl Acad Sci USA. 108, 6579-6584 (2011).

Calkin A C. et al. Reconstituted high-density lipoprotein attenuates platelet function in individuals with type 2 diabetes mellitus by promoting cholesterol efflux. Circulation. 120, 2095-2104 (2009).

Campbell P J, Green A R. The myeloproliferative disorders. N Engl J Med. 355, 2452-2466 (2006).

Carvalho A. C. et al. Platelet function in hyperlipoproteinemia. The New England journal of medicine. 290, 434-438 (1974)

Castelli W. P. et al. Hdl cholesterol and other lipids in coronary heart disease. The cooperative lipoprotein phenotyping study. Circulation. 55, 767-772 (1977).

Chan, V. W. et al. Characterization of the B lymphocyte populations in Lyn-deficient mice and the role of Lyn in signal initiation and down-regulation. *Immunity* 7, 69-81 (1997).

Chan E. R. et al. An enu-induced recessive mutation in mpl leads to thrombocytopenia with overdominance. Exp Hematol. 37, 276-284 (2009).

Chen H. W. et al. Inhibition of cell growth by oxygenated derivatives of cholesterol. Nature. 251, 419-421 (1974).

Coller, B. S. Historical perspective and future directions in platelet research. J Thromb Haemost 9 Suppl 1, 374-395 (2011).

Corash L. et al. Platelet function and survival in patients with severe hypercholesterolemia. Arteriosclerosis (Dallas, Tex.) 1, 443-448 (1981).

Cortelazzo S. et al. Hydroxyurea for patients with essential thrombocythemia and a high risk of thrombosis. N Engl J Med. 332, 1132-1136 (1995).

Cortin V. et al. Ex vivo megakaryocyte expansion and platelet production from human cord blood stem cells. Methods Mol Biol. 482, 109-126 (2009).

Davi G, et al. Diabetes mellitus, hypercholesterolemia, and hypertension but not vascular disease per se are associated with persistent platelet activation in vivo. Evidence derived from the study of peripheral arterial disease. Circulation. 96, 69-75 (1997).

Duffy D, Rader D J. Update on strategies to increase hdl quantity and function. Nature reviews. 6, 455-463 (2009).

Dupont H. et al. Megakaryopoiesis disturbances in atherosclerotic rabbits. Atherosclerosis. 63, 15-26 (1987).

Eckly A. et al. Mechanisms underlying fecl3-induced arterial thrombosis. J Thromb Haemost. 9, 779-789 (2011).

Finn A. V. et al. Concept of vulnerable/unstable plaque. Arteriosclerosis, thrombosis, and vascular biology. 30, 1282-1292 (2010).

Flaumenhaft, R. et al. Platelet- and megakaryocyte-derived microparticles. Semin Thromb Hemost 36, 881-887 (2010).

Frontelo, P., et al. Novel role for EKLF in megakaryocyte lineage commitment. Blood 110, 3871-3880 (2007).

Gilles L, et al. Mal/srf complex is involved in platelet formation and megakaryocyte migration by regulating myl9 (mlc2) and mmp9. Blood. 114, 4221-4232 (2009).

Glomset J A. High-density lipoproteins in human health and disease. Advances in internal medicine. 25, 91-116 (1980).

Gomes A. L. et al. Hypercholesterolemia promotes bone marrow cell mobilization by perturbing the sdf-1:Cxcr4 axis. Blood. 115, 3886-3894 (2010).

Gordon T. et al. High density lipoprotein as a protective factor against coronary heart disease. The framingham study. The American journal of medicine. 62, 707-714 (1977).

Gui T. et al. In vivo response to vascular injury in the absence of factor ix: Examination in factor ix knockout mice. Thromb Res. 121, 225-234 (2007).

Guthikonda, S. et al. Role of reticulated platelets and platelet size heterogeneity on platelet activity after dual antiplatelet therapy with aspirin and clopidogrel in patients with stable coronary artery disease. J Am Coll Cardiol 52, 743-749 (2008).

Harker L A, Hazzard W. Platelet kinetic studies in patients with hyperlipoproteinemia: Effects of clofibrate therapy. Circulation. 60, 492-496 (1979).

Hasselbalch, H. C. Perspectives on chronic inflammation in essential thrombocythemia, polycythemia vera, and myelofibrosis: is chronic inflammation a trigger and driver of clonal evolution and development of accelerated atherosclerosis and second cancer? Blood 119, 3219-3225 (2012).

Hitchcock, I. S. et al. YRRL motifs in the cytoplasmic domain of the thrombopoietin receptor regulate receptor internalization and degradation. Blood 112, 2222-2231 (2008).

Hunter, S. et al. Fyn associates with Cbl and phosphorylates tyrosine 731 in Cbl, a binding site for phosphatidylinositol 3-kinase. The Journal of biological chemistry 274, 2097-2106 (1999).

Huo, Y., et al. Circulating activated platelets exacerbate atherosclerosis in mice deficient in apolipoprotein E. Nature medicine 9, 61-67 (2003).

Imbach P, Crowther M. Thrombopoietin-receptor agonists for primary immune thrombocytopenia. N Engl J Med. 365, 734-741 (2011).

Ingley, E., et al. Lyn deficiency reduces GATA-1, EKLF and STAT5, and induces extramedullary stress erythropoiesis. Oncogene 24, 336-343 (2005).

Investigators, Aim-High, Boden W E, Probstfield J L, Anderson T, Chaitman B R, Desvignes-Nickens P, Koprowicz K, McBride R, Teo K, Weintraub W. Niacin in patients with low hdl cholesterol levels receiving intensive statin therapy. The New England journal of medicine. 365, 2255-2267 (2011).

James C, et al. A unique clonal jak2 mutation leading to constitutive signalling causes polycythaemia vera. Nature. 434, 1144-1148 (2005).

Jamieson C H, et al. The jak2 v617f mutation occurs in hematopoietic stem cells in polycythemia vera and predisposes toward erythroid differentiation. Proc Natl Acad Sci USA. 103, 6224-6229 (2006).

Ji Y, et al. Scavenger receptor bi promotes high density lipoprotein-mediated cellular cholesterol efflux. The Journal of biological chemistry. 272, 20982-20985 (1997).

Kales, S. C. et al. Cbl and human myeloid neoplasms: the Cbl oncogene comes of age. *Cancer Res* 70, 4789-4794 (2010).

Kaplan K L, et al. Platelet alpha-granule proteins: Studies on release and subcellular localization. Blood. 53, 604-618 (1979).

Kaplan Z S, Jackson S P. The role of platelets in athero-thrombosis. Hematology Am Soc Hematol Educ Program. 51-61 (2011).

Karpatkin S, Garg S K. The megathrombocyte as an index of platelet production. Br J Haematol. 26, 307-311 (1974).

Kastelein J J, et al. Effect of torcetrapib on carotid atherosclerosis in familial hypercholesterolemia. The New England journal of medicine. 356, 1620-1630 (2007).

Katsman Y, et al. Improved mouse models for the study of treatment modalities for immune-mediated platelet destruction. Transfusion. 50, 1285-1294 (2010).

Kaushansky, K. Historical review: megakaryopoiesis and thrombopoiesis. Blood 111, 981-986 (2008).

Kaushansky K. The mpl ligand: Molecular and cellular biology of the critical regulator of megakaryocyte development. Stem cells (Dayton, Ohio). 12, Suppl 1:91-96, discussion 96-97 (1994).

Kearney P M, et al. Efficacy of cholesterol-lowering therapy in 18,686 people with diabetes in 14 randomised trials of statins: A meta-analysis. Lancet. 371, 117-125 (2008).

Keck S, et al. Activation of murine macrophages via tlr2 and tlr4 is negatively regulated by a lyn/pi3k module and promoted by ship1. J Immunol. 184, 5809-5818 (2010).

Kelemen, E. et al. Responses to single-dose thrombopoietin decrease with higher platelet counts in mice. Acta Haematol 101, 41-45 (1999).

Khera A V, et al. Cholesterol efflux capacity, high-density lipoprotein function, and atherosclerosis. The New England journal of medicine. 364, 127-135 (2011).

Kilsdonk, E. P. et al. Cellular cholesterol efflux mediated by cyclodextrins. J Biol Chem 270, 17250-17256 (1995).

Kirii H, et al. Lack of interleukin-1beta decreases the severity of atherosclerosis in apoe-deficient mice. Arteriosclerosis, thrombosis, and vascular biology. 23, 656-660 (2003).

Klovaite J, et al. High platelet volume and increased risk of myocardial infarction: 39,531 participants from the general population. J Thromb Haemost. 9, 49-56 (2011).

Koenen, R. R. et al. Disrupting functional interactions between platelet chemokines inhibits atherosclerosis in hyperlipidemic mice. Nature medicine 15, 97-103 (2009).

Koppikar, P. et al. Efficacy of the JAK2 inhibitor INCB16562 in a murine model of MPLW515L-induced thrombocytosis and myelofibrosis. Blood 115, 2919-2927 (2010).

Koppikar, P. et al. Heterodimeric JAK-STAT activation as a mechanism of persistence to JAK2 inhibitor therapy. Nature 489, 155-159 (2012).

Korporaal S J. et al. Deletion of the high-density lipoprotein receptor scavenger receptor bi in mice modulates thrombosis susceptibility and indirectly affects platelet function by elevation of plasma free cholesterol. Arteriosclerosis, thrombosis, and vascular biology. 31, 34-42 (2010).

Labarthe, D. R. & Dunbar, S. B. Global cardiovascular health promotion and disease prevention: 2011 and beyond. Circulation 125, 2667-2676 (2012).

Lakkis, N., et al. Reticulated platelets in acute coronary syndrome: a marker of platelet activity. J Am Coll Cardiol 44, 2091-2093 (2004).

Lannutti, B. J. et al. Identification and activation of Src family kinases in primary megakaryocytes. Exp Hematol 31, 1268-1274 (2003).

Lannutti, B. J. et al. Increased megakaryocytopoiesis in Lyn-deficient mice. Oncogene 25, 3316-3324 (2006).

Libby, P. et al. Progress and challenges in translating the biology of atherosclerosis. Nature 473, 317-325 (2011).

Lievens D. et al. Platelet cd40l mediates thrombotic and inflammatory processes in atherosclerosis. Blood. 116, 4317-4327 (2010).

Lingwood, D. & Simons, K. Lipid rafts as a membrane-organizing principle. Science (New York, N. Y 327, 46-50 (2010).

Lipinski C. A. et al. Bronchodilator and antiulcer phenoxypyrimidinones. J Med Chem. 23, 1026-1031 (1980).

Lu, X. et al. Dimerization by a cytokine receptor is necessary for constitutive activation of JAK2V617F. The Journal of biological chemistry 283, 5258-5266 (2008).

Ma Y, Ashraf M Z, Podrez E A. Scavenger receptor bi modulates platelet reactivity and thrombosis in dyslipidemia. Blood. 116, 1932-1941 (2010).

Martin, J. F. et al. The causal role of megakaryocyte-platelet hyperactivity in acute coronary syndromes. Nat Rev Cardiol (2012).

Marty, C., et al. Ligand-independent thrombopoietin mutant receptor requires cell surface localization for endogenous activity. The Journal of biological chemistry 284, 11781-11791 (2009).

Massberg, S., et al. A critical role of platelet adhesion in the initiation of atherosclerotic lesion formation. The Journal of experimental medicine 196, 887-896 (2002).

Mause, S. F. et al. Platelet microparticles: a transcellular delivery system for RANTES promoting monocyte recruitment on endothelium. Arteriosclerosis, thrombosis, and vascular biology 25, 1512-1518 (2005).

Maurisse R. et al. Comparative transfection of DNA into primary and transformed mammalian cells from different lineages. BMC Biotechnol. 10, 9 (2010).

Mazoyer E. et al. Morphological and kinetic abnormalities of platelets in hypercholesterolemic rabbits. Atherosclerosis. 74, 23-32 (1988).

Mazzone, A. et al. Increased expression of neutrophil and monocyte adhesion molecules in unstable coronary artery disease. Circulation 88, 358-363 (1993).

Meurs, I. et al. The effect of ABCG1 deficiency on atherosclerotic lesion development in LDL receptor knockout mice depends on the stage of atherogenesis. Atherosclerosis 221, 41-47 (2012).

Michiels J. J. et al. Platelet-mediated thrombotic complications in patients with et: Reversal by aspirin, platelet reduction, and not by coumadin. Blood Cells Mol Dis. 36, 199-205 (2006).

Michiels J. J. The use of aspirin and clinical implications in essential thrombocythemia. Semin Thromb Hemost. 32, 646-648 (2006).

Michiels J. J. & Bernaman, Z. et al. The paradox of platelet activation and impaired function: Platelet-von willebrand factor interactions, and the etiology of thrombotic and hemorrhagic manifestations in essential thrombocythemia and polycythemia vera. Semin Thromb Hemost. 32, 589-604 (2006).

Moore K. J, Tabas I. Macrophages in the pathogenesis of atherosclerosis. Cell. 145, 341-355 (2011).

Murphy, A. J., et al. ApoE regulates hematopoietic stem cell proliferation, monocytosis, and monocyte accumulation in atherosclerotic lesions in mice. *The Journal of clinical investigation* 121, 4138-4149 (2011).

Nakorn, T. N. et al. Characterization of mouse clonogenic megakaryocyte progenitors. Proceedings of the National Academy of Sciences of the United States of America 100, 205-210 (2003).

Nofer, J. R. & van Eck, M. HDL scavenger receptor class B type I and platelet function. Curr Opin Lipidol 22, 277-282 (2011).

Ochman, A. R. et al. The Lyn kinase activator MLR-1023 is a novel insulin receptor potentiator that elicits a rapid-onset and durable improvement in glucose homeostasis in animal models of type 2 diabetes. J Pharmacol Exp Ther 342, 23-32 (2012).

Oneyama, C., et al. Transforming potential of Src family kinases is limited by the cholesterol-enriched membrane microdomain. Mol Cell Biol 29, 6462-6472 (2009).

Oneyama, C., et al. Transforming potential of Src family kinases is limited by the cholesterol-enriched membrane microdomain. Mol Cell Biol 29, 6462-6472 (2009).

Pardanani A D et al. Mpl515 mutations in myeloproliferative and other myeloid disorders: A study of 1182 patients. Blood. 108, 3472-3476 (2006).

Pathansali R, Smith N, Bath P. Altered megakaryocyte-platelet haemostatic axis in hypercholesterolaemia. Platelets. 12, 292-297 (2001).

Paul A, et al. Reduced progression of atherosclerosis in apolipoprotein e-deficient mice with phenylhydrazine-induced anemia. Atherosclerosis. 147, 61-68 (1999).

Pikman, Y. et al. MPLW515L is a novel somatic activating mutation in myelofibrosis with myeloid metaplasia. PLoS Med 3, e270 (2006).

Ranalletta, M. et al. Decreased atherosclerosis in low-density lipoprotein receptor knockout mice transplanted with Abcg1-/- bone marrow. Arteriosclerosis, thrombosis, and vascular biology 26, 2308-2315 (2006).

Randi M. L. et al. Src tyrosine kinase preactivation is associated with platelet hypersensitivity in essential thrombocythemia and polycythemia vera. Blood. 115, 667-676 (2010).

Reheman A, Yang H, Zhu G, Jin W, He F, Spring C M, Bai X, Gross P L, Freedman J, Ni H. Plasma fibronectin depletion enhances platelet aggregation and thrombus formation in mice lacking fibrinogen and von willebrand factor. Blood. 113, 1809-1817 (2009).

Reininger A. J. Et al. Mechanism of platelet adhesion to von willebrand factor and microparticle formation under high shear stress. Blood. 107, 3537-3545 (2006).

Ross, R. The pathogenesis of atherosclerosis: a perspective for the 1990s. Nature 362, 801-809 (1993).

Sachais B. S. et al. Elimination of platelet factor 4 (pf4) from platelets reduces atherosclerosis in c57bl/6 and apoe-/- mice. Thromb Haemost. 98, 1108-1113 (2007).

Sanchez, M. et al. Differential amplification of murine bipotent megakaryocytic/erythroid progenitor and precursor cells during recovery from acute and chronic erythroid stress. Stem cells (Dayton, Ohio) 24, 337-348 (2006).

Sankaranarayanan S. et al. A sensitive assay for abca1-mediated cholesterol efflux using BODIPY-cholesterol. Journal of lipid research. 52, 2332-2340 (2011).

Saporito, M. S. et al. MLR-1023 is a potent and selective allosteric activator of Lyn kinase in vitro that improves glucose tolerance in vivo. *J Pharmacol Exp Ther* 342, 15-22 (2012).

Saur, S. J. et al. Ubiquitination and degradation of the thrombopoietin receptor c-Mpl. Blood 115, 1254-1263 (2010).

Schick B P, Schick P K. The effect of hypercholesterolemia on guinea pig platelets, erythrocytes and megakaryocytes. Biochim Biophys Acta. 833, 291-302 (1985).

Schmidt M H, Dikic I. The cbl interactome and its functions. Nat Rev Mol Cell Biol. 6, 907-918 (2005).

Schoenwaelder S. M. et al. Two distinct pathways regulate platelet phosphatidylserine exposure and procoagulant function. Blood. 114, 663-666 (2009).

Shah P. K. et al. Effects of recombinant apolipoprotein a-i(milano) on aortic atherosclerosis in apolipoprotein e-deficient mice. Circulation. 97, 780-785 (1998).

Shattil S. J. et al. Platelet hypersensitivity induced by cholesterol incorporation. The Journal of clinical investigation. 55, 636-643 (1975).

Shivdasani R. A. et al. A lineage-selective knockout establishes the critical role of transcription factor gata-1 in megakaryocyte growth and platelet development. EMBO J. 16, 3965-3973 (1997).

Steinberg, D. The statins in preventive cardiology. N Engl J Med 359, 1426-1427 (2008).

Stohlawetz, P. et al. Measurement of the levels of reticulated platelets after plateletpheresis to monitor activity of thrombopoiesis. Transfusion 38, 454-458 (1998).

Suzuki N. et al. Erythroid-specific expression of the erythropoietin receptor rescued its null mutant mice from lethality. Blood. 100, 2279-2288 (2002).

Tall, A. R., Yvan-Charvet, L., Terasaka, N., Pagler, T. & Wang, N. HDL, ABC transporters, and cholesterol efflux: implications for the treatment of atherosclerosis. Cell metabolism 7, 365-375 (2008).

Tanaka S. et al. Tyrosine phosphorylation and translocation of the c-cbl protein after activation of tyrosine kinase signaling pathways. The Journal of biological chemistry. 270, 14347-14351 (1995).

Tardif, J. C. et al. Effects of reconstituted high-density lipoprotein infusions on coronary atherosclerosis: a randomized controlled trial. JAMA: the journal of the American Medical Association 297, 1675-1682 (2007).

Tefferi, A. Myelofibrosis with myeloid metaplasia. N Engl J Med 342, 1255-1265 (2000).

Tefferi, A. & Vainchenker, W. Myeloproliferative neoplasms: molecular pathophysiology, essential clinical understanding, and treatment strategies. J Clin Oncol 29, 573-582 (2011).

Tefferi, A. Novel mutations and their functional and clinical relevance in myeloproliferative neoplasms: JAK2, MPL, TET2, ASXL1, CBL, IDH and IKZF1. Leukemia 24, 1128-1138 (2010).

Tiedt, R., et al. Pronounced thrombocytosis in transgenic mice expressing reduced levels of Mpl in platelets and terminally differentiated megakaryocytes. Blood 113, 1768-1777 (2009).

Tong, W. et al. Signals emanating from the membrane proximal region of the thrombopoietin receptor (mpl) support hematopoietic stem cell self-renewal. *Exp Hematol* 35, 1447-1455 (2007).

Trebus F. et al. H. Transient experimental anemia in cholesterol-fed rabbits induces systemic overexpression of the reticulocyte-type 15-lipoxygenase and protects from aortic lipid deposition. Prostaglandins Leukot Essent Fatty Acids. 67, 419-428 (2002).

Underwood K. W. et al. Evidence for a cholesterol transport pathway from lysosomes to endoplasmic reticulum that is independent of the plasma membrane. The Journal of biological chemistry. 273, 4266-4274 (1998).

Van der Loo B, Martin J F. A role for changes in platelet production in the cause of acute coronary syndromes. Arteriosclerosis, thrombosis, and vascular biology. 19, 672-679 (1999).

Verstovsek, S. et al. Safety and efficacy of INCB018424, a JAK1 and JAK2 inhibitor, in myelofibrosis. N Engl J Med 363, 1117-1127 (2010).

Villmow, T. et al. Markers of platelet activation and platelet-leukocyte interaction in patients with myeloproliferative syndromes. Thromb Res 108, 139-145 (2002).

Wagner, D. D. & Burger, P. C. Platelets in inflammation and thrombosis. Arteriosclerosis, thrombosis, and vascular biology 23, 2131-2137 (2003).

Wang N, Arai T, Ji Y, Rinninger F, Tall A R. Liver-specific overexpression of scavenger receptor bi decreases levels of very low density lipoprotein apob, low density lipoprotein apob, and high density lipoprotein in transgenic mice. J Biol Chem. 273, 32920-32926 (1998).

Wang, N., Lan, D., Chen, W., Matsuura, F. & Tall, A. R. ATP-binding cassette transporters G1 and G4 mediate cellular cholesterol efflux to high-density lipoproteins. Proc Natl Acad Sci USA 101, 9774-9779 (2004).

Wang, N., Ranalletta, M., Matsuura, F., Peng, F. & Tall, A. R. LXR-induced redistribution of ABCG1 to plasma membrane in macrophages enhances cholesterol mass efflux to HDL. Arteriosclerosis, thrombosis, and vascular biology 26, 1310-1316 (2006).

Wang N, Yvan-Charvet L, Lutjohann D, Mulder M, Vanmierlo T, Kim T W, Tall A R. Atp-binding cassette transporters g1 and g4 mediate cholesterol and desmosterol efflux to hdl and regulate sterol accumulation in the brain. Faseb J. 22, 1073-1082 (2008).
Waterman, H. et al. The RING finger of c-Cbl mediates desensitization of the epidermal growth factor receptor. J Biol Chem 274, 22151-22154 (1999).
Weintraub A H, Karpatkin S. Heterogeneity of rabbit platelets. Ii. Use of the megathrombocyte to demonstrate a thrombopoietic stimulus. J Lab Clin Med. 83, 896-901 (1974).
Wessels P. et al. Kinetics and in vivo distribution of in-111-labelled platelets and platelet function in familial hypercholesterolaemia. Thrombosis and haemostasis. 58, 811-816 (1987).
Wolf P. The nature and significance of platelet products in human plasma. Br J Haematol. 13, 269-288 (1967).
Yoshikawa M. et al. Molecular and cytogenetic characterization of the mouse atp-binding cassette transporter abcg4. Gene. 293, 67-75 (2002).
Yvan-Charvet L. et al. Sr-bi inhibits abcg1-stimulated net cholesterol efflux from cells to plasma hdl. Journal of lipid research. 49, 107-114 (2008).
Yvan-Charvet L. et al. Role of hdl, abca1, and abcg1 transporters in cholesterol efflux and immune responses. Arteriosclerosis, thrombosis, and vascular biology. 30, 139-143 (2009).
Yvan-Charvet, L. et al. ATP-binding cassette transporters and HDL suppress hematopoietic stem cell proliferation. Science 328, 1689-1693 (2010).

What is claimed:

1. A method of treating a subject suffering from a myeloproliferative neoplasm which comprises administering to the subject an amount of a Lyn kinase activator effective to activate Lyn kinase so as to thereby treat the subject.

2. The method of claim 1, wherein the myeloproliferative neoplasm is essential thrombocytosis (ET) or primary myelofibrosis (MF).

3. The method of claim 1, wherein the subject's chromosomes comprise a JAK2 mutation.

4. The method of claim 3, further comprising administering a JAK2 inhibitor to the subject.

5. The method of claim 1, wherein the Lyn kinase activator is a compound having the structure:

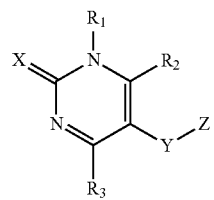

wherein
X is O, S or NH;
Y is O, S, CH$_2$ or NH;
Z is aryl or heteroaryl;
R$_1$ is —H or alkyl;
Each of R$_2$ and R$_3$ is independently —H, —CF$_3$, —CN, —NO$_2$, —OR$_4$, CO$_2$R$_4$, —CO$_2$R$_4$, —NHR$_4$, —NR$_4$R$_4$, alkyl, cycloalkyl, heterocycloalkyl, alkenyl, alkynyl, aryl, alkylaryl, heteroaryl, or halogen, and
wherein each R$_4$ is independently —H, alkyl, cycloalkyl, heterocycloalkyl, alkenyl, alkynyl, aryl, alkylaryl, or heteroaryl,
or a pharmaceutically acceptable salt or ester thereof.

6. The method of claim 5,
wherein Z is phenyl, pyridine, or pyrimidine, unsubstituted or substituted,
or a pharmaceutically acceptable salt or ester thereof.

7. The method of claim 6, wherein Z is a compound having the structure:

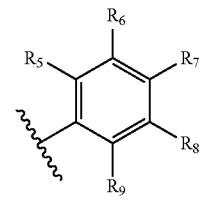

wherein each of R$_5$, R$_6$, R$_7$, R$_8$ and R$_9$ is independently —H, —CF$_3$, —CN, —NO$_2$, —OR$_{10}$, CO$_2$R$_{10}$, —CO$_2$R$_{10}$, —NHR$_{10}$, —NR$_{10}$R$_{10}$, alkyl, cycloalkyl, heterocycloalkyl, alkenyl, alkynyl, aryl, alkylaryl, heteroaryl, or halogen, and
wherein each R$_{10}$ is independently —H, alkyl, cycloalkyl, heterocycloalkyl, alkenyl, alkynyl, aryl, alkylaryl, or heteroaryl,
or a pharmaceutically acceptable salt or ester thereof.

8. The method of claim 7, wherein Z is a compound having the structure:

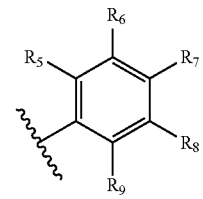

wherein each of R$_5$, R$_6$, R$_7$, R$_8$ and R$_9$ is —H, —CH$_3$,—Cl, —F, —OH, —CF$_3$, or —NH$_2$,
or a pharmaceutically acceptable salt or ester thereof.

9. The method of claim 8, wherein Z is

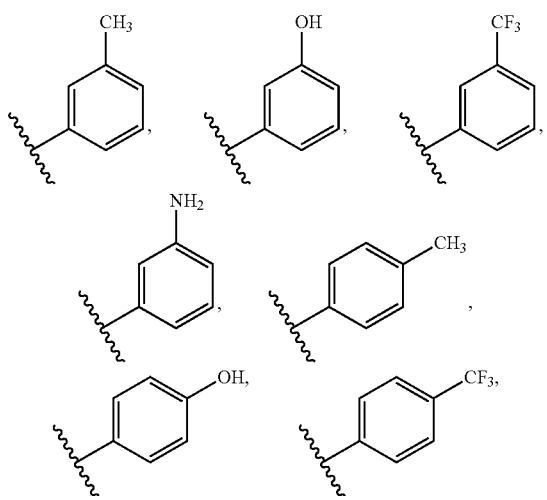

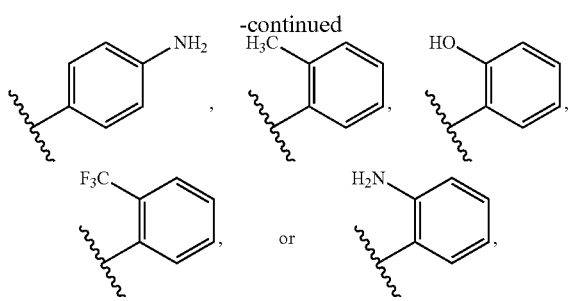

or a pharmaceutically acceptable salt or ester thereof.

10. The method of claim 5, wherein each of X and Y is O, or a pharmaceutically acceptable salt or ester thereof.

11. The method of claim 5, wherein each of $R_1$, $R_2$ and $R_3$ is —H, or a pharmaceutically acceptable salt or ester thereof.

12. The method of claim 5, wherein the Lyn kinase activator is a compound having the structure:

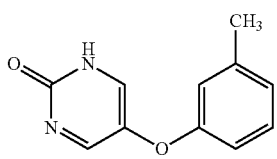

or a pharmaceutically acceptable salt or ester thereof.

13. The method of claim 5, wherein the Lyn kinase activator is a compound having the structure:

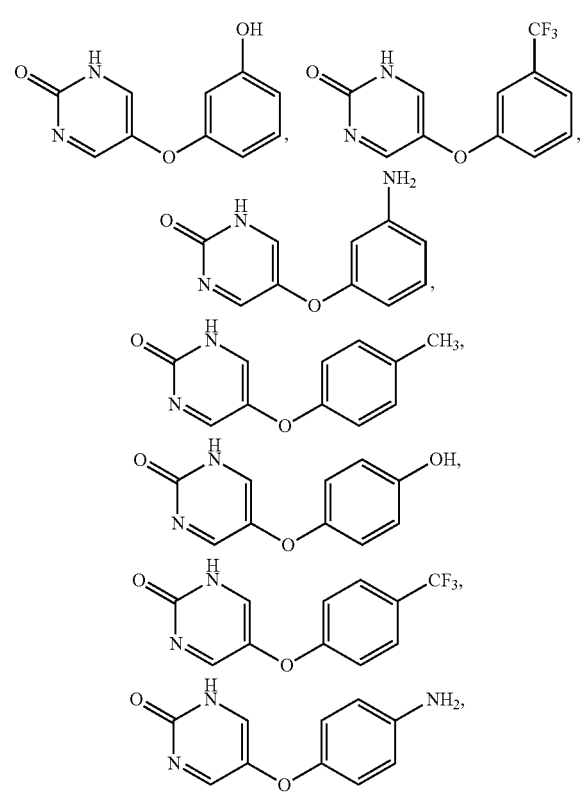

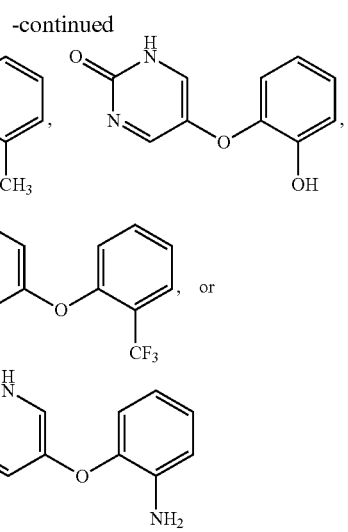

or a pharmaceutically acceptable salt or ester thereof.

14. A method of treating a subject suffering from a myeloproliferative neoplasm which comprises administering to the subject an effective amount of a composition comprising a compound having the structure:

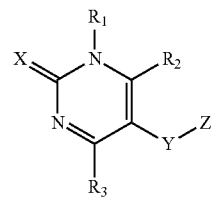

wherein
X is O, S or NH;
Y is O, S, $CH_2$ or NH;
Z is aryl or heteroaryl;
$R_1$ is —H or alkyl;
Each of $R_2$ and $R_3$ is independently —H, —$CF_3$, —CN, —$NO_2$, —$OR_4$, —$CO_2R_4$, —$CO_2R_4$, —$NHR_4$, —$NR_4R_4$, alkyl, cycloalkyl, heterocycloalkyl, alkenyl, alkynyl, aryl, alkylaryl, heteroaryl, or halogen, and
wherein each $R_4$ is independently —H, alkyl, cycloalkyl, heterocycloalkyl, alkenyl, alkynyl, aryl, alkylaryl, or heteroaryl,
or a pharmaceutically acceptable salt or ester thereof, in an amount effective to activate Lyn kinase.

15. The method of claim 14, wherein the compound has the structure:

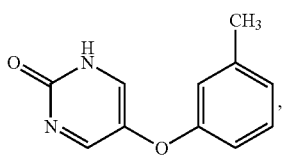

or a pharmaceutically acceptable salt or ester thereof.